(12) United States Patent
Ben-David et al.

(10) Patent No.: US 9,456,998 B2
(45) Date of Patent: Oct. 4, 2016

(54) SELECTIVE INHIBITORS OF UNDIFFERENTIATED CELLS

(71) Applicants: Yissum Research Development Company of the Hebrew University of Jerusalem Ltd., Jerusalem (IL); Hoffmann-La Roche Inc., Nutley, NJ (US)

(72) Inventors: Uri Ben-David, Jerusalem (IL); Nissim Benvenisty, Jerusalem (IL); Payal Arora, Bridgewater, NJ (US); Qing-Fen Gan, Palo Alto, CA (US); Ralph J. Garippa, Roseland, NJ (US)

(73) Assignees: Yissum Research Development Company of the Hebrew University of Jerusalem Ltd., Jerusalem (IL); Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/402,467

(22) PCT Filed: May 22, 2013

(86) PCT No.: PCT/IL2013/050441
§ 371 (c)(1),
(2) Date: Nov. 20, 2014

(87) PCT Pub. No.: WO2013/175474
PCT Pub. Date: Nov. 28, 2013

(65) Prior Publication Data
US 2015/0148359 A1    May 28, 2015

Related U.S. Application Data

(60) Provisional application No. 61/696,387, filed on Sep. 4, 2012, provisional application No. 61/650,049, filed on May 22, 2012.

(51) Int. Cl.
| | |
|---|---|
| *A61K 31/4409* | (2006.01) |
| *A61K 31/15* | (2006.01) |
| *A61K 31/34* | (2006.01) |
| *A61K 31/403* | (2006.01) |
| *A61K 31/407* | (2006.01) |
| *A61K 31/4453* | (2006.01) |
| *A61K 31/4545* | (2006.01) |
| *A61K 31/4985* | (2006.01) |
| *A61K 31/136* | (2006.01) |
| *A61K 31/155* | (2006.01) |
| *A61K 31/165* | (2006.01) |
| *A61K 31/166* | (2006.01) |
| *A61K 31/341* | (2006.01) |
| *A61K 31/343* | (2006.01) |
| *A61K 31/381* | (2006.01) |
| *A61K 31/4015* | (2006.01) |
| *A61K 31/404* | (2006.01) |
| *A61K 31/451* | (2006.01) |
| *A61K 31/513* | (2006.01) |
| *G01N 33/50* | (2006.01) |

(52) U.S. Cl.
CPC ............. *A61K 31/15* (2013.01); *A61K 31/136* (2013.01); *A61K 31/155* (2013.01); *A61K 31/165* (2013.01); *A61K 31/166* (2013.01); *A61K 31/34* (2013.01); *A61K 31/341* (2013.01); *A61K 31/343* (2013.01); *A61K 31/381* (2013.01); *A61K 31/403* (2013.01); *A61K 31/404* (2013.01); *A61K 31/407* (2013.01); *A61K 31/4015* (2013.01); *A61K 31/4409* (2013.01); *A61K 31/4453* (2013.01); *A61K 31/451* (2013.01); *A61K 31/4545* (2013.01); *A61K 31/4985* (2013.01); *A61K 31/513* (2013.01); *G01N 33/502* (2013.01); *G01N 33/5073* (2013.01); *G01N 2500/02* (2013.01); *G01N 2500/10* (2013.01)

(58) Field of Classification Search
CPC .................................................. A61K 31/4409
See application file for complete search history.

(56) References Cited

U.S. PATENT DOCUMENTS

2008/0182838 A1    7/2008  Leblanc et al.

FOREIGN PATENT DOCUMENTS

| | | |
|---|---|---|
| EP | 0663391 | 7/1995 |
| WO | WO 2005/011653 | 2/2005 |
| WO | WO 2005/011654 | 2/2005 |
| WO | WO 2005/011655 | 2/2005 |
| WO | WO 2005/011656 | 2/2005 |
| WO | WO 2005/011657 | 2/2005 |
| WO | WO 2006/014168 | 2/2006 |
| WO | WO 2006/034279 | 3/2006 |
| WO | WO 2006/034312 | 3/2006 |
| WO | WO 2006/034315 | 3/2006 |
| WO | WO 2006/034338 | 3/2006 |
| WO | WO 2006/034341 | 3/2006 |
| WO | WO 2006/034440 | 3/2006 |
| WO | WO 2006/034441 | 3/2006 |
| WO | WO 2006/034446 | 3/2006 |

(Continued)

OTHER PUBLICATIONS

Communication Relating to the Results of the Partial International Search Dated Aug. 7, 2013 From the International Searching Authority Re. Application No. PCT/IL2013/050441.

(Continued)

*Primary Examiner* — Robert Havlin

(57) ABSTRACT

Uses of a compound of any of Formulas I-VI as a cytotoxic inhibitor of undifferentiated cells are disclosed herein, as well as pharmaceutical compositions comprising a compound of any of Formulas I-VI, and methods for identifying a lead candidate for inhibiting undifferentiated cells. Further disclosed are uses of an SCD-1 inhibitor as a cytotoxic inhibitor of undifferentiated cells.

3 Claims, 51 Drawing Sheets
(48 of 51 Drawing Sheet(s) Filed in Color)

(56) References Cited

FOREIGN PATENT DOCUMENTS

| WO | WO 2006/086445 | 8/2006 |
|---|---|---|
| WO | WO 2006/086447 | 8/2006 |
| WO | WO 2006/101521 | 9/2006 |
| WO | WO 2006/114313 | 11/2006 |
| WO | WO 2006/125178 | 11/2006 |
| WO | WO 2006/125179 | 11/2006 |
| WO | WO 2006/125180 | 11/2006 |
| WO | WO 2006/125181 | 11/2006 |
| WO | WO 2006/125194 | 11/2006 |
| WO | WO 2006/130986 | 12/2006 |
| WO | WO 2007/009236 | 1/2007 |
| WO | WO 2007/044085 | 4/2007 |
| WO | WO 2007/046867 | 4/2007 |
| WO | WO 2007/046868 | 4/2007 |
| WO | WO 2007/050124 | 5/2007 |
| WO | WO 2007/130075 | 11/2007 |
| WO | WO 2007/136746 | 11/2007 |
| WO | WO 2007/143597 | 12/2007 |
| WO | WO 2007/143823 | 12/2007 |
| WO | WO 2007/143824 | 12/2007 |
| WO | WO 2008/003753 | 1/2008 |
| WO | WO 2008/017161 | 2/2008 |
| WO | WO 2008/024390 | 2/2008 |
| WO | WO 2008/029266 | 3/2008 |
| WO | WO 2008/036715 | 3/2008 |
| WO | WO 2008/044767 | 4/2008 |
| WO | WO 2008/046226 | 4/2008 |
| WO | WO 2008/056687 | 5/2008 |
| WO | WO 2008/062276 | 5/2008 |
| WO | WO 2008/064474 | 6/2008 |
| WO | WO 2008/074824 | 6/2008 |
| WO | WO 2008/074834 | 6/2008 |
| WO | WO 2008/074835 | 6/2008 |
| WO | WO 2008/096746 | 8/2008 |
| WO | WO 2008/127349 | 10/2008 |
| WO | WO 2009/070533 | 6/2009 |
| WO | WO 2010/144059 | 12/2010 |
| WO | WO 2011/030329 | 3/2011 |
| WO | WO 2013/175474 | 11/2013 |

OTHER PUBLICATIONS

Corrected International Search Report and the Written Opinion Dated Feb. 11, 2014 From the International Searching Authority Re. Application No. PCT/IL2013/050441.
International Preliminary Report on Patentability Dated Dec. 4, 2014 From the International Bureau of WIPO Re. Application No. PCT/IL2013/050441.
International Search Report and the Written Opinion Dated Nov. 15, 2013 From the International Searching Authority Re. Application No. PCT/IL2013/050441.
Al-Hajj et al. "Prospective Identifiaction of Tumorgenic Breast Cancer Cells", Proc. Natl. Acad. Sci. USA, PNAS, 100(7): 3983-3988, Apr. 1, 2003.
Assou et al. "A Meta-Analysis of Human Embryonic Stem Cells Transcriptome Integrated Into a Web-Based Expression Atlas", Stem Cells, 25: 961-973, 2007.
Attie et al. "Relationship Between Stearoyl-CoA Desaturase Activity and Plasma Triglycerides in Human and Mouse Hypertriglyceridemia", Journal of Lipid Research, 43: 1899-1907, 2002.
Behrouzian et al. "Mechanism of Fatty Acid Desaturation: A Bioorganic Perspective", Prostaglandins, Leukotrienes and Essential Fatty Acids, 68: 107-112, 2003.
Ben-David et al. "Selective Elimination of Human Pluripotent Stem Cells by an Oleate Synthesis Inhibitor Discovered in a High-Throuput Screen", Stem Cell Stein, XP055072276, 12(2): 167-179, Feb. 7, 2013.
Ben-David et al. "The Tumorigenicity of Human Embryonic and Induced Pluripotent Stem Cells", Nature Reviews Cancer, 11: 268-277, Apr. 2011.

Bieberich et al. "Selective Apoptosis of Pluripotent Mouse and Human Stem Cells by Novel Ceramide Analogues Prevents Teratoma Formation and Enriches for Neural Precursors in ES Cell-Derived Neural Transplants", The Journal of Cell Biology, XP002529566, 167(4): 723-734, Nov. 22, 2004. Abstract, p. 726, Fig.2.
Blum et al. "The Anti-Apoptotic Gene Survivin Contributes to Teratoma Formation by Human Embryonic Stem Cells", Nature Biotechnology, 27(3): 281-287, Mar. 2009.
Boiko et al. "Human Melanoma Initiating Cells Express Neural Crest Nerve Growth Factor Receptor CD271", Nature, 466(7302): 133-137, Jul. 1, 2010.
Bonnet et al. "Human Acute Myeloid Leukemia Is Organized as a Hierarchy That Originates From a Primitive Hematopoietic Cell", Nature Medicine, 3(7): 730-737, Jul. 1997.
Borradaile et al. "A Critical Role for Eukaryotic Elongation Factor 1A-1 in Lipotoxic Cell Death", Molecular Biology of the Cell 17: 770-778, Feb. 2006.
Borradaile et al. "Disruption of Endoplasmic Reticulum Structure and Integrity in Lipotoxic Cell Death", Journal of Lipid Research, 47: 2726-2737, 2006.
Buur et al. "Prodrugs of 5-Fluorouracil. III. Hydrolysis Kinetics in Aqueous Solution and Biological Media, Lipophilicity and Solubility of Various 1-Carbamoyl Derivatives of 5-Fluorouracil", International Journal of Pharmaceutics, 23: 209-222, 1985.
Campos et al. "Differentiation Therapy Exerts Antitumor Effects on Stem-Like Glioma Cells", Clinical Cancer Research, 16(10): 2715-2728, May 4, 2010.
Chippendale et al. "Condensed Thiophen Ring Systems. Part X. Synthesis and Reactions of 2-Aryl-1H-[1]Benzothieno[2,3-b]Pyrroles and 2-Aryl-1H-[1]Benzothieno[3,2-b]Pyrroles", Journal of the Chemical Society, Perkin Transactions I, XP009171444, 2: 125-129, Jan. 1, 1973. Abstract, p. 127, Compound 10.
Choo et al. "Selection Against Undifferentiated Human Embryonic Stem Cells by a Cytotoxic Antibody Recognhizing Podocalyxin-Like Protein-1", Stem Cells, 26: 1454-1463, 2008.
Chupina et al. "Indole Derivatives. 135. 5-[2-(4-Methoxyphenyl)Ethenyl]Indolines and Indoles", Datsahase CAPLUS [Online], XP002319001, AN 1990:35623, Accession No. DN 112:35623, Jan. 1, 1989. Abstract.
Civenni et al. "Human CD271-Positive Melanoma Stem Cells Associated With Metastasis Establish Tumor Heterogeneity and Long-Term Growth", Cancer Research, 71(8): 3098-3109, Apr. 15, 2011.
Fong et al. "Separation of SSEA-4 and TRA-1-60 Labelled Undifferentiated Human Embryonic Stem Cells From a Heterogeneous Cell Population Using Magnetic-Activated Cell Sorting (MACS) and Fluorescence-Activated Cell Sorting (FACS)", Stem Cells Reviews and Reports, 5(1): 72-80, Mar. 2009.
Fu et al. "Residual Undifferentiated Cells During Differentiation of Induced Pluripotent Stem Cells In Vitro and In Vivo", Stem Cells and Development, 21(4): 521-529, 2012.
Ghosh et al. "Dissecting the Oncogenic and Tumorigenic Potential of Differentiated Human Induced Pluripotent Stem Cells and Human Embryonic Stem Cells", Cancer Research, 71: 5030-5039, Jun. 6, 2011.
Gupta et al. "Identification of Selective Inhibitors of Cancer Stem Cells by High-Thoughput Screening", Cell, XP055001903, 138(4): 645-659, Aug. 1, 2009. Abstract, p. 648, r-h Col., Para 2, p. 651, Fig.4.
Hapala et al. "Is Fat so Bad? Modulation of Endoplasmic Reticulum Stress by Lipid Droplet Formation", Biology of the Cell, 103(6): 271-285, Jun. 2011.
Hara et al. "Neuron-Like Differentiation and Selective Ablation of Undifferentiated Embryonic Stem Cells Containing Suicide Gene With Oct-4 Promoter", Stem Cells and Development, 17: 619-628, 2008.
Hentze et al. "Teratoma Formation by Human Embryonic Stem Cells: Evaluation of Essential Parameters for Future Safety Studies", Stem Cell Research, 2: 198-210, 2009.

(56) References Cited

OTHER PUBLICATIONS

Hess et al. "Inhibition of StearoylCoA Desaturase Activity Blocks Cell Cycle Progression and Induces Programmed Cell Death in Lung Cancer Cells", PLoS ONE, XP002692272, 5(6): e11394-1-e11394-8, Jun. 30, 2010. Abstract.
Hoshi et al. "Antitumor Activity of Carbamoyl Derivatives of 5-Fluorouracil by Oral Administration", Gann, 66(6): 673-674, Dec. 1975.
Iigo et al. "Antitumor Activity of 1-Alkylcarbamoyl Derivatives of 5-Fluorouracil in a Variety of Mouse Tumors", Cancer Chemotherapy and Pharmacology, 1: 203-208, 1978.
Itskovitz-Eldor "A Panel of Glycan Cell Surface Markers Define Pluripotency State and Promote Safer Cell-Based Therapies", Stem Cell Stem, XP028310024, 9(4): 291-292, Oct. 7, 2011.
Lang et al. "Prostate Cancer Stem Cells", Journal of Pathology, 217: 299-306, Oct. 29, 2008.
Lee et al. "Effects of Cell Number on Teratoma Formation by Human Embryonic Stem Cells", Cell Cycle, 8(16): 2608-2612, Aug. 15, 2009.
Li et al. "Identification of Pancreatic Cancer Stem Cells", Cancer Research, 67(3): 1030-1037, Feb. 1, 2007.
Liu "Stearoyl-CoA Desaturase Inhibitors: Update on Patented Compounds", Expert Opinion on Therapeutic Patents, 19(9): 1169-1191, Sep. 2009.
Liu et al. "Discovery of Potent, Selective, Orally Bioavailable Stearoyl-CoA Desaturase 1 Inhibitors", Journal of Medicianl Chemistry, 50: 3086-3100, 2007.
Maitland et al. "Prostate Cancer Stem Cells: A New Target for Therapy", Journal of Clinical Oncology, 26(17): 2862-2870, Jun. 10, 2008.
Mason et al. "SCD1 Inhibition Causes Cancer Cell Death by Depleting Mono-Unsaturated Fatty Acids", PLoS ONE, 7(3): e33823-1-e33823-8, Mar. 2012.
Matsui et al. "Characterization of Clonogenic Multiple Myeloma Cells", Blood, 103(6): 2332-2336, Mar. 15, 2004.
Matsui et al. "Clonogenic Multiple Myeloma Progenitors, Stem Cell Properties, and Drug Resistance", Cancer Research, 68(1): 190-197, Jan. 1, 2008.
Medema "Cancer Stem Cells: The Challenges Ahead", Nature Cell Biology, 15(4): 338-344, Apr. 2013.
Menendez et al. "Increased Dosage of Tumor Suppressors Limits the Tumorigenicity of iPS Cells Without Affecting Their Pluripotency", Aging Cell, 11: 41-50, 2011.
Minville-Walz et al. "Inhibition of Stearoyl-CoA Desaturase 1 Expression Induces CHOP-Dependent Cell Death in Human Cancer Cells", PLoS ONE, XP055072956, 5(12): e14363-1-e14363-13, Dec. 16, 2010. Abstract.
Miura et al. "Variation in the Safety of Induced Pluripotent Stem Cell Lines", Nature Biotechnology, 27(8): 743-745, Aug. 2009.
Momcilovic et al. "DNA Damage Responses in Human Induced Pluripotent Stem Cells and Embryonic Stem Cells", PLoS ONE, 5(10: e13410-1-e13410-14, Oct. 2010.
Morgan-Lappe et al. "Identification of Ras-Related Nuclear Protein, Targeting Protein for Xenopus Kinesin-Like Protein 2, and Stearoyl-CoA Desaturase 1 as Promising Cancer Targets Fom an RNAi-Based Screen", Cancer Research, 67: 4390-4398, May 4, 2007.
Narsinh et al. "Single Cell Transcriptional Profiling Reveals Heterogeneity of Human Induced Pluripotent Stem Cells", The Journal of Clinical Investigation, 121(3): 1217-1221, Mar. 2011.
O'Brien et al. "A Human Colon Cancer Cell Capable of Initiating Tumour Growth in Immunodeficient Mice", Nature, 445: 106-110, Jan. 4, 2007.
Ozaki et al. "5-Fluorouracil Derivatives. XXIII. Synthesis and Antitumor Activities of 1-Carbamoyl-5-Fluorouracils Having Aromatic Ring", Chinese Journal of Chemistry, 16(2): 171-177, 1998.
Ozaki et al. "5-Fluorouracil. I. The Synthesis of 1-Carbamoyl-5-Fluorouracils", Bulletin of the Chemical Society of Japan, 50(9): 2406-2412, Sep. 1977.

Pandey et al. "Resveratrol Suppresses Growth of Cancer Stem-Like Cells by Inhibiting Fatty Acid Synthase", Breast Cancer Research and Treatment, XP019962447, 130(2): 387-398, Dec. 29, 2010. Abstract, p. 393, 1-h Col., Para 2-r-h Col., Para 2.
Park et al. "Inhibition of Hepatic Stearoyl-CoA Desaturase Activity by Trans-10,Cis-12 Conjugated Linoleic Acid and Its Derivatives", Biochimica et Biophysica Acta, 1486: 285-292, 2000.
Peng et al. "Oleate Blocks Palmitate-Induced Abnormal Lipid Distribution, Endoplasmic Reticulum Expansion and Stress, and Insulin Resistance in Skeletal Muscle", Endocrinology, 152(6): 2206-2218, Jun. 2011.
Preston et al. "Reduced Endoplasmic Reticulum (ER)-to-Golgi Protein Trafficking Contributes to ER Stress in Lipotoxic Mouse Beta Cells by Promoting Protein Overload", Diabetologia, 52: 2369-2373, 2009.
Puri et al. "Concise Review: Embryonic Stem Cells Versus Induced Pluripotent Stem Cells: The Game Is On", Stem Cells, 30: 10-14, 2012.
Qin et al. "Regulation of Apoptosis and Differentiation by P53 in Human Embryonic Stem Cells", The Journal of Biological Chemistry, 282(8): 5842-5852, Feb. 23, 2007.
Raju et al. "Inhibition of Fatty Acyl Desaturase by Cyclopropene Fatty Acids", The Journal of Biological Chemistry, 242(3): 379-384, Feb. 10, 1967.
Regenbrecht et al. "The Molecular Basis of Genistein-Induced Mitotic Arrest and Exit of Self-Renewal in Embryonal Carcinoma and Primary Cancer Cell Lines", BMC Medical Genomics, XP021045841, 1(49): 1-13, Oct. 10, 2008. Abstract, p. 50, r-h Col., Para 2, p. 51, 1-h Col., Para 3.
Roongta et al. "Cancer Cell Dependance on Unsaturated Fatty Acids Implicates Stearoyl-CoA Desaturase as a Target for Cancer Therapy", Molecular Cancer Research, XP055072211, 9(11): 1551-1561, Sep. 27, 2011. Abstract, p. 1554, 1-h Col., Para 2-r-h Col., Para 2.
Scaffidi et al. "In Vitro Generation of Human Cells With Cancer Stem Cell Properties", Nature Cell Biology, 13(9): 1051-1061, Aug. 21, 2011.
Scaglia et al "Inhibition of StearoylCoA Desaturase-1 Inactivates Acetyl-CoA Carboxylase and Impairs Proliferation in Cancer Cells: Role of AMPK", PLoS ONE, 4(8): e6812-1-e6812-14, Aug. 2009.
Scaglia et al. "Stearoyl-CoA Desaturase Is Involved in the Control of Proliferation, Anchorage-Independent Growth, and Survival in Human Transformed Cells", The Journal of Biological Chemistry, 280(27): 25339-25349, Jul. 8, 2005.
Schatton et al. "Identification of Cells Initiating Human Melanomas", Nature, 451(7176): 345-349, Jan. 17, 2008.
Schmidt et al. "Eradication of Melanomas by Targeted Elimination of a Minor Subset of Tumor Cells", Proc. Natl. Acad. Sci. USA, PNAS, 108(6): 2474-2479, Feb. 8, 2011.
Schriebl et al. "Selective Removal of Undifferentiated Human Embryonic Stem Cells Using Magnetic Activated Cell Sorting Followed by a Cytotoxic Antibody", Tissue Engineering: Part A, 18(9/10): 899-909, 2012.
Schuldiner et al. "Selective Ablation of Human Embryonic Stem Cells Expressing A 'Suicide' Gene", Stem Cells, 21: 257-265, 2003.
Singh et al. "Identification of a Cancer Stem Cell in Human Brain Tumors", Cancer Research, 63: 5821-5828, Sep. 15, 2003.
Tang et al. "An Antibody Against SSEA-5 Glycan on Human Pluripotent Stem Cells Enables Removal of Teratoma-Forming Cells", Nature Biotechnology, 29(9): 829-835, Sep. 2011.
Toth "1-Acetyl-2-Phenylhydrazine Carcinogenesis in Mice", British Journal of Cancer, XP002706081, 39(5): 584-587, 1979. p. 585-586, Tables 1-2.
Visvader et al. "Cancer Stem Cells in Solid Tumours: Accumulating Evidence and Unresolved Questions", Nature Reviews Cancer, 8: 755-768, Oct. 2008.
Wang et al. "Acetyl-CoA Carboxylase-Alpha Inhibitor TOFA Induces Human Cancer Cell Apoptosis", Biochemical and Biophysical Research Communications, XP026281581, 385(3): 302-306, Jul. 31, 2009. Abstract.
Wang et al. "Specific Lectin Biomarkers for Isolation of Human Pluripotent Stem Cells Identified Through Array-Based Glycomic Analysis", Cell Research, 21: 1551-1563, 2011.

(56) References Cited

OTHER PUBLICATIONS

Xin et al. "Discovery of Piperidine-Aryl Urea-Based Stearoyl-CoA Desaturase 1 Inhibitors", Bioorganic & Medicinal Chemistry Letters, 18: 4298-4302, 2008.

Zhang et al. "Identification and Characterization of Ovarian Cancer-Initiating Cells From Primary Human Tumors", Cancer Research, 68(11): 4311-4320, Jun. 1, 2008.

Zhang et al. "Scd1 Plays a Tumor-Suppressive Role in Survival of Leukemia Stem Cells and the Development of Chronic Myeloid Leukemia", Molecular and Cellular Biology, XP055072864, 32(10): 1776-1787, May 15, 2012. Abstract, p. 1781, r-h Col., Para 3, p. 1783, 1-h Col., Lines 4-9-r-h Col., Para 2.

Zhao et al. "Discovery of 1-(4-Phenoxypiperidin-1-Y)-2-Arylaminoethanone Stearoyl-CoA Desaturase 1 Inhibitors", Bioorganic & Medicinal Chemistry Letters, 17: 3388-3391, 2007.

Translation Dated Mar. 6, 2016 of Notification of Office Action Dated Feb. 14, 2016 From the State Intellectual Property Office of the People's Republic of China Re. Application No. 201380038889.6.

Notificaiton of Office Action Dated Feb. 14, 2016 From the State Intellectual Property Office of the People's Republic of China Re. Application No. 201380038889.6 and Its Summary in English.

24h

72h

120h

ESC-derived teratoma iPSC-derived teratoma

Control                A939572

SELECTIVE INHIBITORS OF UNDIFFERENTIATED CELLS

RELATED APPLICATIONS

This application is a National Phase of PCT Patent Application No. PCT/IL2013/050441 having International filing date of May 22, 2013, which claims the benefit of priority under 35 USC §119(e) of U.S. Provisional Patent Application Nos. 61/696,387 filed on Sep. 4, 2012 and 61/650,049 filed on May 22, 2012. The contents of the above applications are all incorporated by reference as if fully set forth herein in their entirety.

FIELD AND BACKGROUND OF THE INVENTION

The present invention, in some embodiments thereof, relates to therapy and, more particularly, but not exclusively, to treatment of undifferentiated cells such as pluripotent cells and undifferentiated cancel cells, to novel compounds suitable therefor, and to methods of identifying compounds suitable therefor.

Human pluripotent stem cells (hPSCs) hold great promise for regenerative medicine, due to their unique abilities to self-renew and to differentiate into all the cell types of the human body. However, the same properties also make these cells potentially tumorigenic.

Tumor formation was reported to positively correlate with the residual presence of undifferentiated pluripotent cells [Miura et al., Nature Biotechnology 27:743-745 (2009)]. Very few hPSCs are required for teratoma formation [Lee et al., Cell Cycle 8:2608-2612 (2009); Hentze et al., Stem Cell Research 2:198-210 (2009)], and even after prolonged differentiation in culture some tumorigenic pluripotent cells remain [Narsinh et al., Journal of Clinical Investigation 121:1217-1221 (2011); Ghosh et al., Cancer Research 71:5030-5039 (2011); Fu et al., Stem Cells and Development 21:521-529 (2012)].

It has therefore been recommended to eliminate residual pluripotent cells prior to the clinical application of their derivatives [Ben-David & Benvenisty, Nature Reviews Cancer 11:268-277 (2011)].

Importantly, while the generation of induced pluripotent stem (iPS) cells may have resolved the problem of immunogenic rejection, the risk of teratoma formation remains a major obstacle that is equally relevant for embryonic stem (ES) cells and for iPS cells [Miura et al., Nature Biotechnology 27:743-745 (2009); Fu et al., Stem Cells and Development 21:521-529 (2012); Ben-David & Benvenisty, Nature Reviews Cancer 11:268-277 (2011); Puri & Nagy, Stem Cells 30:10-14 (2012).

To promote the removal of residual pluripotent cells from differentiated cultures, several strategies have been suggested, based on either genetic manipulations or cell sorting, including: introduction of suicide genes [Schuldiner et al., Stem Cells 21:257-265 (2003); Hara. et al., Stem Cells and Development 17:619-627 (2008)]; interference with tumor progression genes [Blum et al., Nature Biotechnology 27:281-287 (2009)] or with tumor suppressors [Menendez et al., Aging Cell 11:41-50 (2012)]; fluorescence-activated or magnetic-activated cell sorting (FACS or MACS) based on antibodies against PSC-specific surface antigens [Fong et al., Stem Cell Reviews 5:72-80 (2009); Tang et al., Nature Biotechnology 29:829-834 (2011); Wang et al., Cell Research 21:1551-1563 (2011)]; and the use of cytotoxic antibodies against pluripotent cells [Choo et al., Stem Cells 26:1454-1463 (2008); Schriebl et al., Tissue Engineering Part A (2012 Jan. 4, electronically published)].

Previous studies have suggested that hPSCs may be especially sensitive to some cellular perturbations, and are thus more prone than other cell types to undergo apoptosis under some circumstances [Qin et al., Journal of Biological Chemistry 282:5842-5852 (2007); Momcilovic et al., PloS One 5:e13410 (2010)].

The cancer stem cell hypothesis postulates that cancer growth is driven by a subset of cancer cells, referred to in the art as cancer stem cells or cancer stem-like cells (CSCs), which are characterized by tumor-initiation potential, self-renewal capacity, resistance to therapy and an ability to differentiate into heterogeneous and possibly non-tumorigenic cancer cells [Scaffidi & Misteli, Nature Cell Biology 13:1051-1061 (2011); Campos et al., Clinical Cancer Research 16:2715-2728 (2010); Medema, Nature Cell Biology 15:338-344 (2013); Visvader & Lindeman, Nature Reviews Cancer 8:755-768 (2008)]. CSCs which have been reported include a subpopulation of leukemia cells which express CD34 but not CD38 [Bonnet & Dick, Nature Medicine 3: 730-737 (1997], as well as cancer cell subpopulations in brain cancer [Singh et al., Cancer Research 63:5821-5828 (2003)], breast cancer [Al-Hajj et al., PNAS 100:3983-3988 (2003)], colon cancer [O'Brien et al., Nature 445:106-110], ovarian cancer [Zhang et al., Cancer Research 68:4311-4320 (2008)], pancreatic cancer [Li et al., Cancer Research 67:1030-1037 (2007)], prostate cancer [Maitland & Collins, Journal of Clinical Oncology 26:2862-2870 (2008); Lang et al., Journal of Pathology 217:299-306 (2009)], melanoma [Schatton et al., Nature 451:345-349 (2008); Boiko et al., Nature 466:133-137 (2010); Schmidt et al., PNAS 108:2474-2479 (2011); Civenni et al., Cancer Research 71:3098-3109 (2011)] and multiple myeloma [Matsui et al., Blood 103:2332-2336 (2004); Matsui et al., Cancer Research 68:190-197 (2008)].

Stearoyl-CoA desaturase (SCD) is an enzyme which catalyzes production of oleic acid by desaturation of stearic acid. Two isoforms, SCD1 and SCD5, have been reported in humans.

Inhibition of SCD1 has been reported to induce endoplasmic reticulum (ER) stress and unfolded protein response (UPR) in some human cancer cell lines, leading to apoptosis of these cells, and has been suggested as a potential target for cancer therapy [Roongta et al., Molecular Cancer Research 9:1551-1561 (2011); Minville-Walz et al., PloS One 5:e14363 (2010); Scaglia et al., PloS One 4:e6812 (2009); Hess et al., PloS One 5:e11394 (2010); Morgan-Lappe et al., Cancer Research 67:4390-4398 (2007); Mason et al., PloS One 7:e33823 (2012)]. SCD1 has been reported to be expressed in hPSCs [Assou et al., Stem Cells 25:961-973 (2007)], but its role in these cells has not been previously described.

Accumulation of saturated fatty acid SCD1 substrates has been reported to induce ER stress and UPR by several mechanisms: generation of reactive oxygen species (ROS), which leads to ER calcium depletion [Borradaile et al., Molecular Biology of the Cell 17:770-778 (2006)]; alteration of the ER membrane composition, which results in a dramatic impairment of its structure and integrity [Borradaile et al., Journal of Lipid Research 47:2726-2737 (2006)]; and impairment of the ER-to-Golgi trafficking, which results in the build-up of proteins in the ER [Preston et al., Diabetologia 52:2369-2373 (2009)]. Oleic acid, the product of SCD1 activity, has been reported to compete with the saturated fatty acids, block the abnormal lipid distribution, and attenuate ER stress [Peng et al., Endocrinology 152:

2206-2218 (2011); Hapala et al., *Biology of the Cell/under the auspices of the European Cell Biology Organization* 103:271-285 (2011)].

High SCD activity has been reported to be associated with increased cardiovascular risk profile, including elevated plasma triglycerides, high body mass index and reduced plasma HDL [Attie et al., *J Lipid Res* 43:1899-1907 (2002)].

International Patent Application PCT/CA2006/000949 (published as WO 2006/130986), International Patent Application PCT/CA2007/001026 (published as WO 2007/143823), International Patent Application PCT/CA2007/001027 (published as WO 2007/143824), International Patent Application PCT/CA2007/001396 (published as WO 2008/017161), International Patent Application PCT/CA2007/001858 (published as WO 2008/046226), International Patent Application PCT/CA2007/002139 (published as WO 2008/064474) and U.S. Patent Application No. 2008/0182838 describe SCD1 inhibitors and uses thereof in the treatment of cardiovascular disease, obesity, diabetes, neurological disease, metabolic syndrome, insulin resistance, cancer and liver steatosis.

Additional background art includes Behrouzian and Buist [*Prostaglandins, Leukotrienes and Essential Fatty Acids* 68:107-112 (2003)]; Raju and Reiser [*J Biol Chem* 242:379-384 (1967)]; Park et al. [*Biochim Biophys Acta* 1486:285-292 (2000)]; Liu et al. [*J Med Chem* 50:3086-3100 (2007)]; Zhao et al. [*Bioorg Med Chem Lett* 17:3388-3391 (2007)]; Xin et al. [*Bioorg Med Chem Lett* 18:4298-4302 (2008)]; and International Patent Applications having publication nos. WO 2005/011653, WO 2005/011654, WO 2005/011655, WO 2005/011656, WO 2005/011657, WO 2006/014168, WO 2006/034279, WO 2006/034312, WO 2006/034315, WO 2006/034338, WO 2006/034341, WO 2006/034440, WO 2006/034441, WO 2006/034446, WO 2006/086445, WO 2006/086447, WO 2006/101521, WO 2006/125178, WO 2006/125179, WO 2006/125180, WO 2006/125181, WO 2006/125194, WO 2007/044085, WO 2007/046867, WO 2007/046868, WO 2007/050124, WO 2007/130075, WO 2007/136746, WO 2008/074835, WO 2008/074835, WO 2008/074824, WO 2008/036715, WO 2008/044767, WO 2008/029266, WO 2008/062276, WO 2008/127349, WO 2008/003753, WO 2007/143697, WO 2008/024390, WO 2008/096746 and WO 2008/056687; and Liu [*Expert Opinion on Therapeutic Patents* 19:1169-1191 (2009)].

SUMMARY OF THE INVENTION

According to an aspect of some embodiments of the invention, there is provided a use of a compound of Formula I

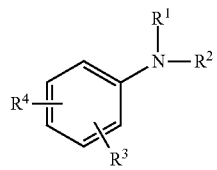

Formula I as a cytotoxic inhibitor of undifferentiated cells, wherein:
R$^1$ is hydrogen, and
R$^2$ is selected from the group consisting of:
  hydrogen,
  2,4-dioxo-5-fluoropyrimidin-1-ylcarbonyl,
  2-methylbenzofuran-3-ylmethyleneamino,
  and —NH—R$^5$, wherein R$^5$ is selected from the group consisting of:
  pyridinylcarbonyl,
  2-hydroxyl-2-phenyl-2-thiophen-2-yl-acetyl,
  (C$_{1-6}$)alkyl-carbonyl,
  N-(ethoxycarbonylmethyl)-2,4-dioxo-pyrrolidine-3-ylidene-methyl,
  naphthylsulfonyl, and
  N-hydroxy-acetimidoyl;
or wherein:
R$^1$ is benzoyl and R$^2$ is 4-chlorobenzamido; and
R$^3$ and R$^4$ are independently selected from the group consisting of hydrogen, halo, NH$_2$, biphenyloxymethyl and (C$_{1-4}$)alkyl,
with the proviso that at least one of R$^1$, R$^2$, R$^3$ and R$^4$ is not hydrogen, halo, NH$_2$ or (C$_{1-4}$)alkyl.

According to some embodiments of the invention, R$^1$ is hydrogen, and
R$^2$ is selected from the group consisting of:
  2,4-dioxo-5-fluoropyrimidin-1-ylcarbonyl,
  2-methylbenzofuran-3-ylmethyleneamino, and
  —NH—R$^5$, wherein R$^5$ is selected from the group consisting of:
    pyridinylcarbonyl,
    2-hydroxyl-2-phenyl-2-thiophen-2-yl-acetyl,
    (C$_{1-6}$)alkyl-carbonyl,
    N-(ethoxycarbonylmethyl)-2,4-dioxo-pyrrolidine-3-ylidene-methyl,
    naphthylsulfonyl, and
    N-hydroxy-acetimidoyl;
or:
R$^1$ is benzoyl and R$^2$ is 4-chlorobenzamido; and
R$^3$ and R$^4$ are independently selected from the group consisting of hydrogen, chloro, NH$_2$, and methyl.

According to an aspect of some embodiments of the invention, there is provided a use of a compound of formula II:

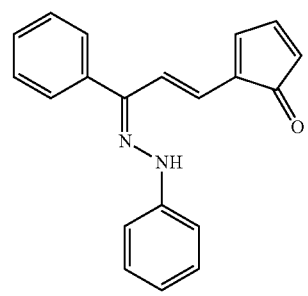

Formula II as a cytotoxic inhibitor of undifferentiated cells.

According to an aspect of some embodiments of the invention, there is provided a use of a compound of formula III:

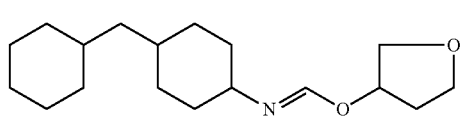

Formula III as a cytotoxic inhibitor of undifferentiated cells.

According to an aspect of some embodiments of the invention, there is provided a use of a compound of formula IV:

Formula IV

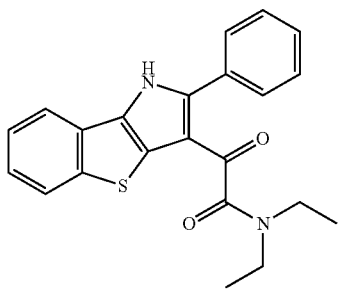

as a cytotoxic inhibitor of undifferentiated cells.

According to an aspect of some embodiments of the invention, there is provided a use of a compound of formula V:

Formula V

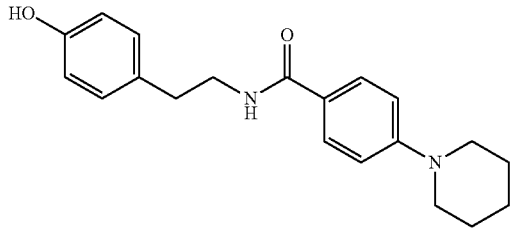 [SMILES: O=C(NCCc1ccc(O)cc1)c1ccc(N2CCCCC2)cc1]

as a cytotoxic inhibitor of undifferentiated cells.

According to an aspect of some embodiments of the invention, there is provided a use of a compound of formula VI:

Formula VI

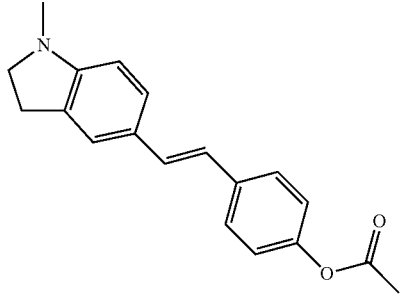 [SMILES: CC(=O)Oc1ccc(/C=C/c2ccc3c(c2)CCN3C)cc1]

as a cytotoxic inhibitor of undifferentiated cells.

According to an aspect of some embodiments of the invention, there is provided a pharmaceutical composition comprising a therapeutically effective amount of a compound described herein and a pharmaceutically acceptable carrier.

According to an aspect of some embodiments of the invention, there is provided a method of treating a proliferative disease or disorder associated with proliferation of undifferentiated cells in a subject in need thereof, the method comprising administering to the subject a therapeutically effective amount of a compound described herein.

According to an aspect of some embodiments of the invention, there is provided a use of a compound described herein in the manufacture of a medicament for treating a proliferative disease or disorder associated with proliferation of undifferentiated cells in a subject in need thereof.

According to an aspect of some embodiments of the invention, there is provided a compound described herein for use in treating a proliferative disease or disorder associated with proliferation of undifferentiated cells in a subject in need thereof.

According to some embodiments of the invention, the composition is identified for use in inhibiting undifferentiated cells.

According to some embodiments of the invention, the undifferentiated cells comprise pluripotent stem cells.

According to some embodiments of the invention, the undifferentiated cells comprise undifferentiated cancer cells.

According to some embodiments of the invention, the composition is identified for use in treating a proliferative disease or disorder associated with proliferation of undifferentiated cells.

According to some embodiments of the invention, the proliferative disease or disorder is selected from the group consisting of a teratoma, an undifferentiated cancer, a leukemia, a brain cancer, a breast cancer, a colon cancer, an ovarian cancer, a pancreatic cancer, a prostate cancer, a melanoma, a liver cancer, a lung cancer, a head and neck cancer, a mesenchymal cancer and a multiple myeloma.

According to an aspect of some embodiments of the invention, there is provided a method of identifying a lead candidate for inhibiting pluripotent stem cells, the method comprising:
  (a) providing a plurality of samples of pluripotent stem cells, each of the samples comprising a different type of pluripotent stem cells;
  (b) contacting the samples with a candidate compound; and
  (c) monitoring a viability of the stem cells in the samples, whereby if the viability is reduced in at least two of the samples, the candidate compound is identified as capable of inhibiting pluripotent stem cells, thereby identifying the lead candidate.

According to some embodiments of the invention, the method is for identifying a lead candidate for selectively inhibiting pluripotent stem cells, the method further comprising:
  (d) providing at least one sample of differentiated cells;
  (e) contacting the at least one sample with the compound identified as capable of reducing a pluripotent stem cell population; and
  (f) monitoring a viability of the differentiated cells in the at least one sample, whereby if the viability is maintained in the at least one sample, the compound is identified as capable of selectively inhibiting pluripotent stem cells.

According to an aspect of some embodiments of the invention, there is provided a use of an SCD1 (Stearoyl-CoA desaturase-1) inhibitor as a cytotoxic inhibitor of pluripotent stem cells.

According to some embodiments of the invention, the SCD1 inhibitor is selected from the group consisting of A939572, CAY-10566, MF-438, CVT-11127, GSK-993, 5-(tetradecyloxy)-2-furoic acid, and a nucleic acid silencing sequence for SCD1.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
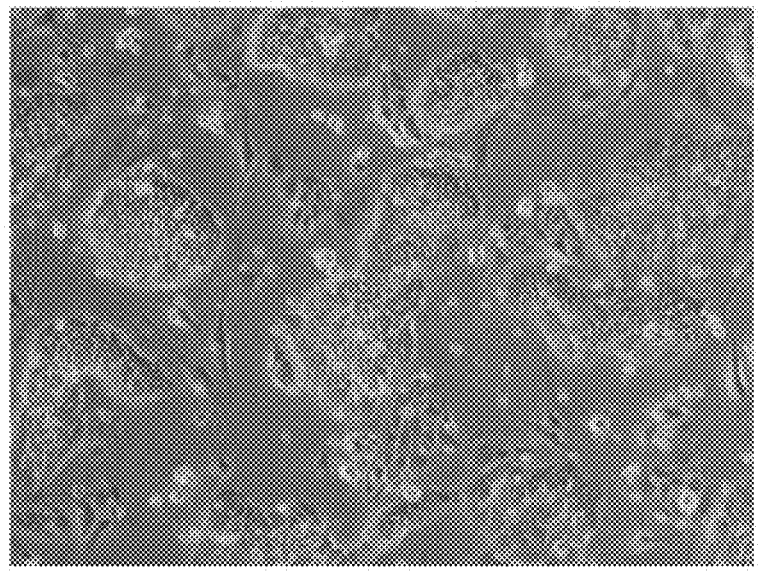
Figure 1B:
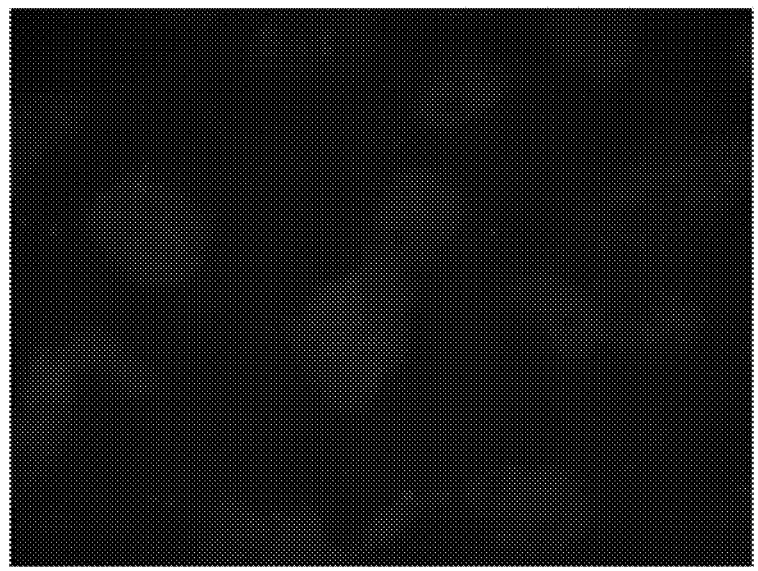
Figure 2A:
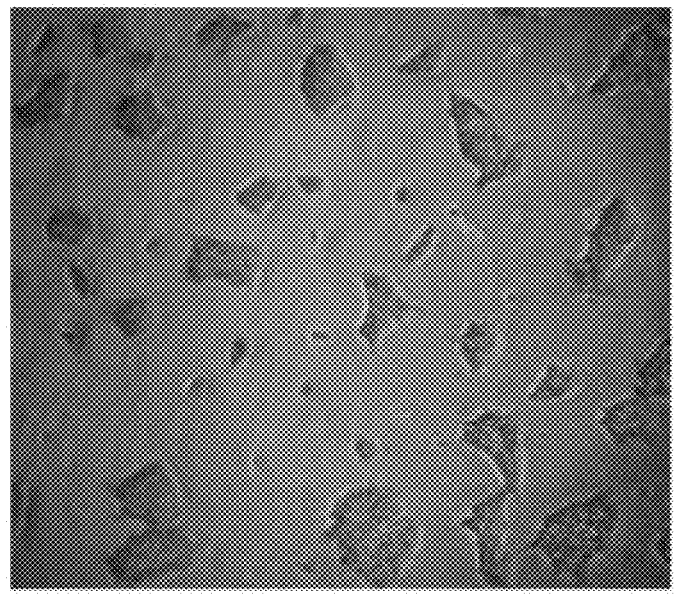
Figure 2B:
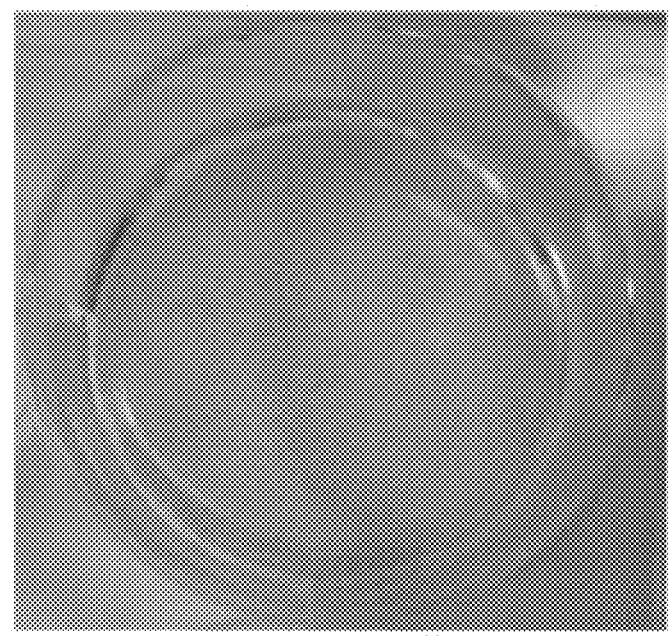
Figure 3:
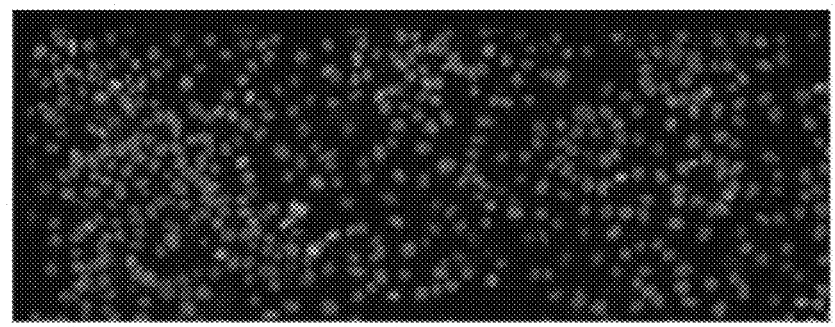
Figure 3:
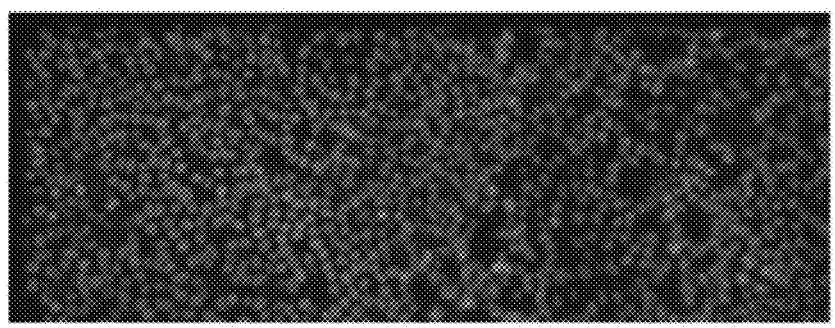
Figure 3:
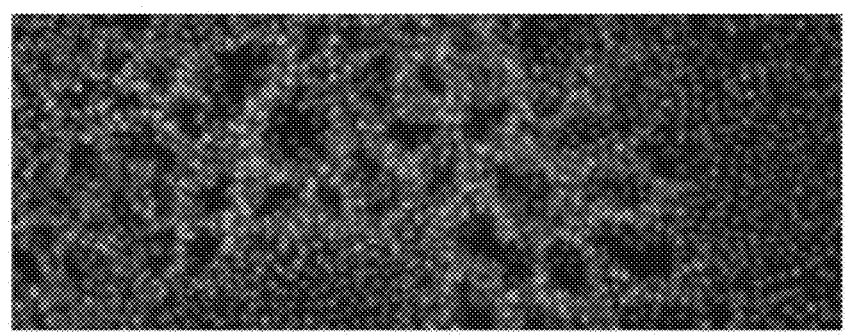
Figure 4:
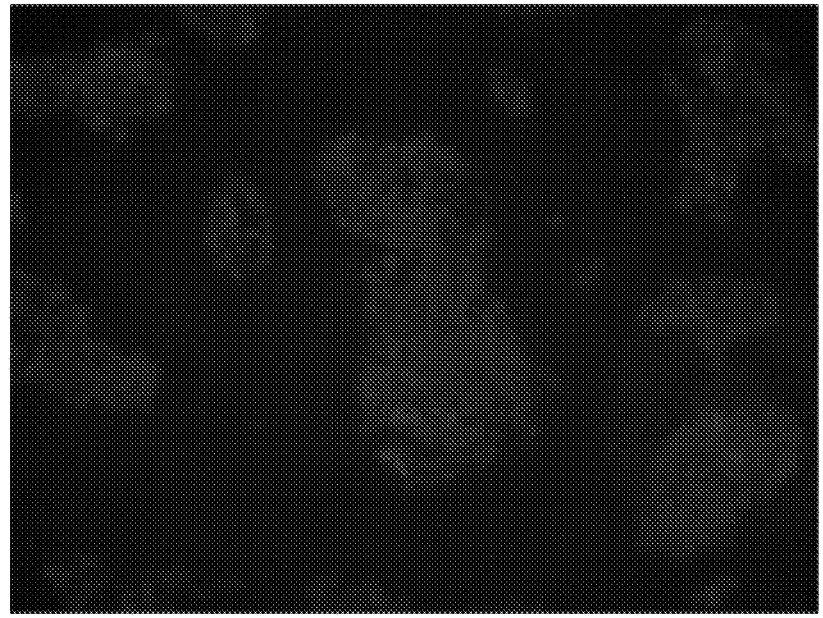
Figure 4:
Figure 5:
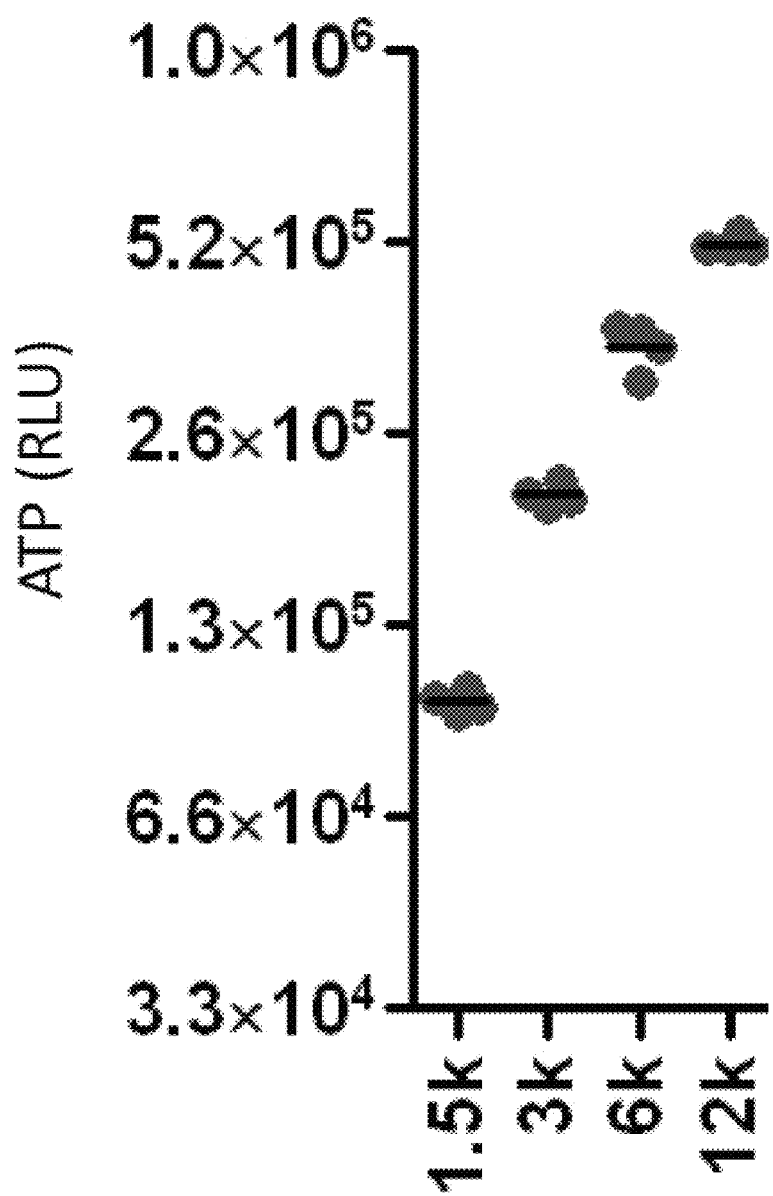
Figure 6:
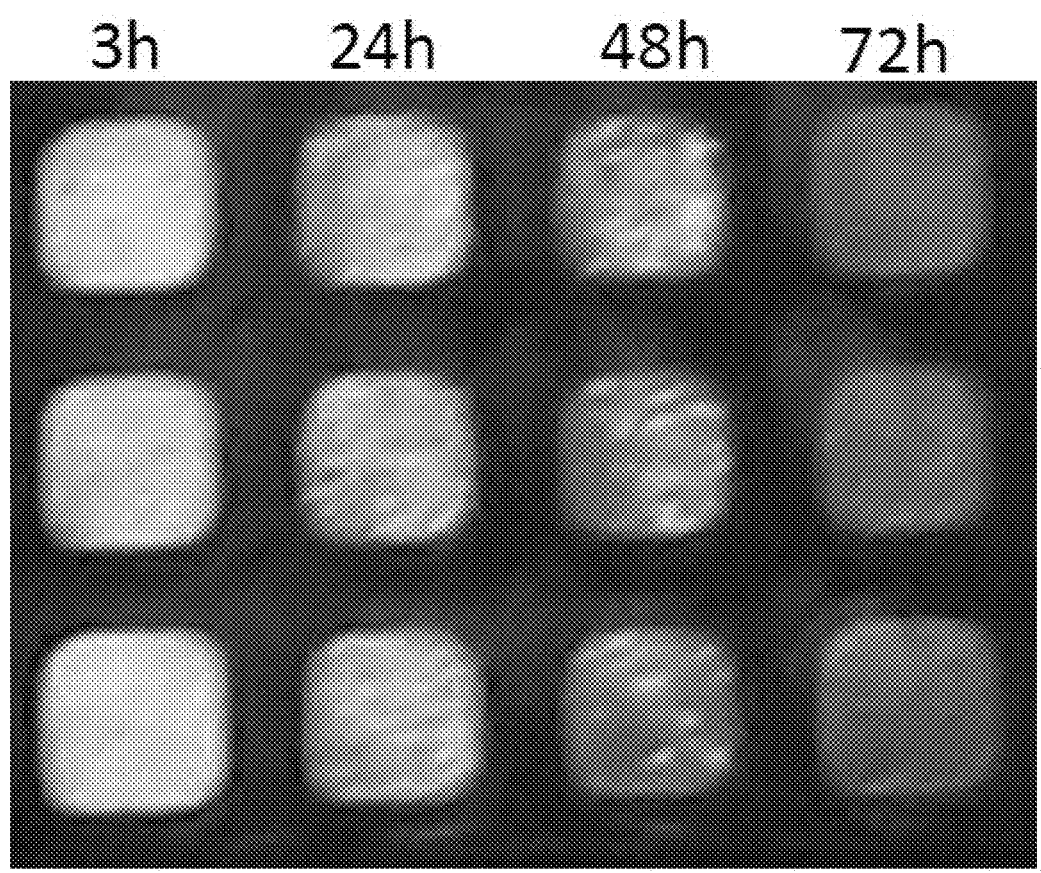
Figures 7, 8:
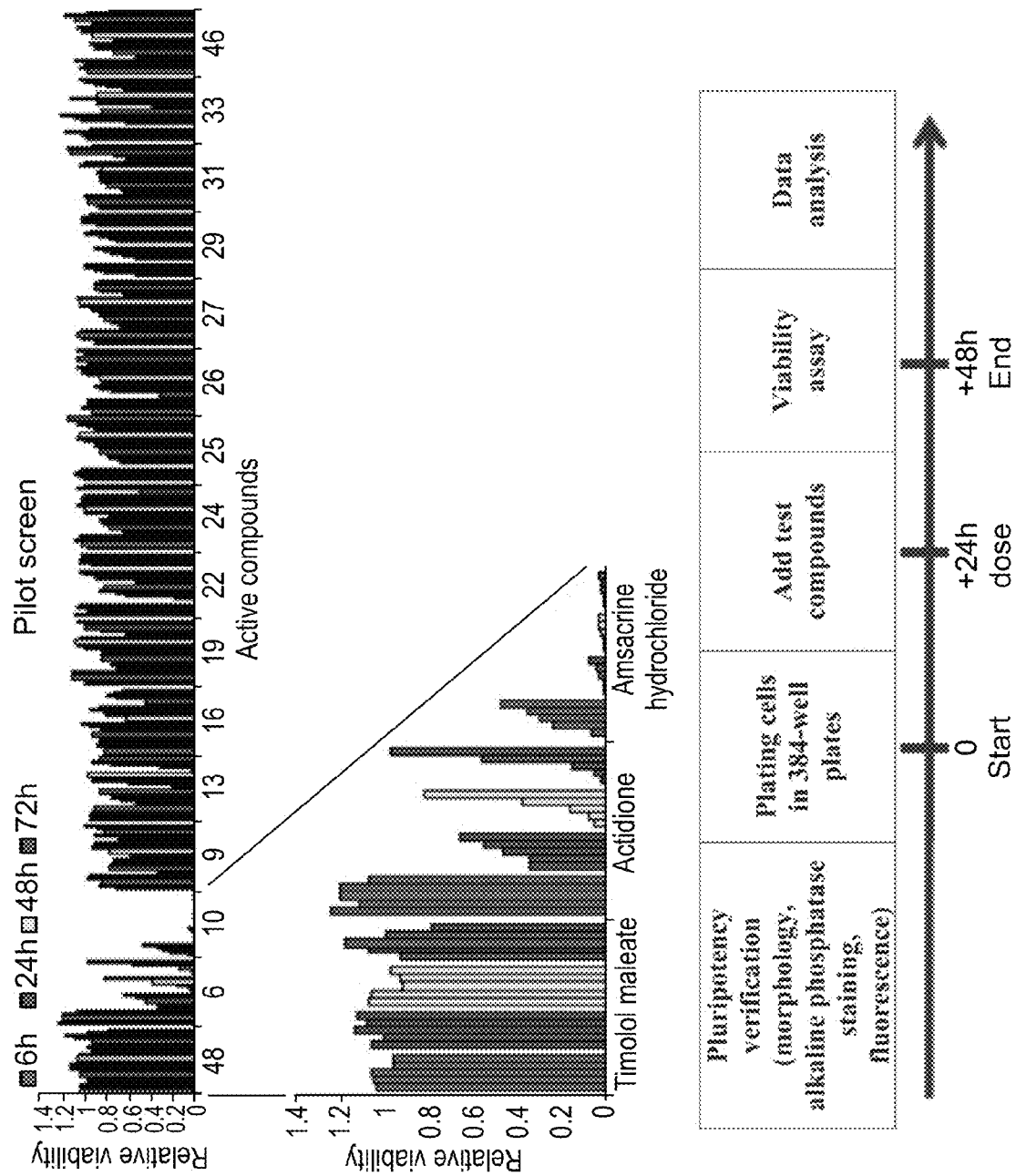
Figure 9:
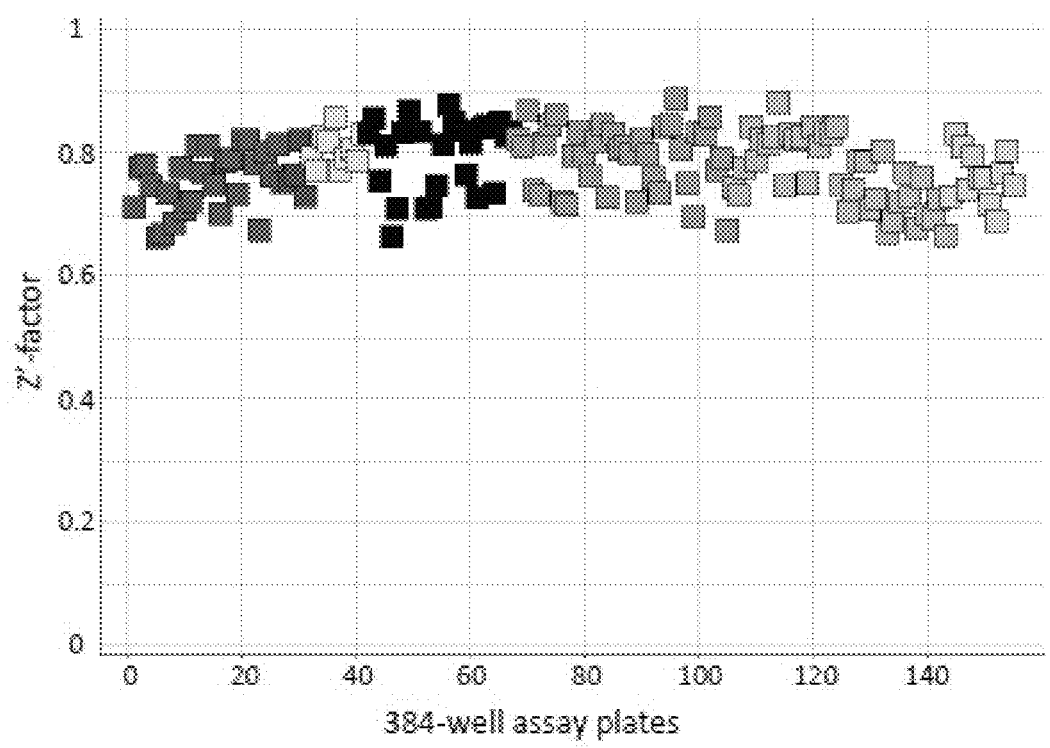
Figure 10:
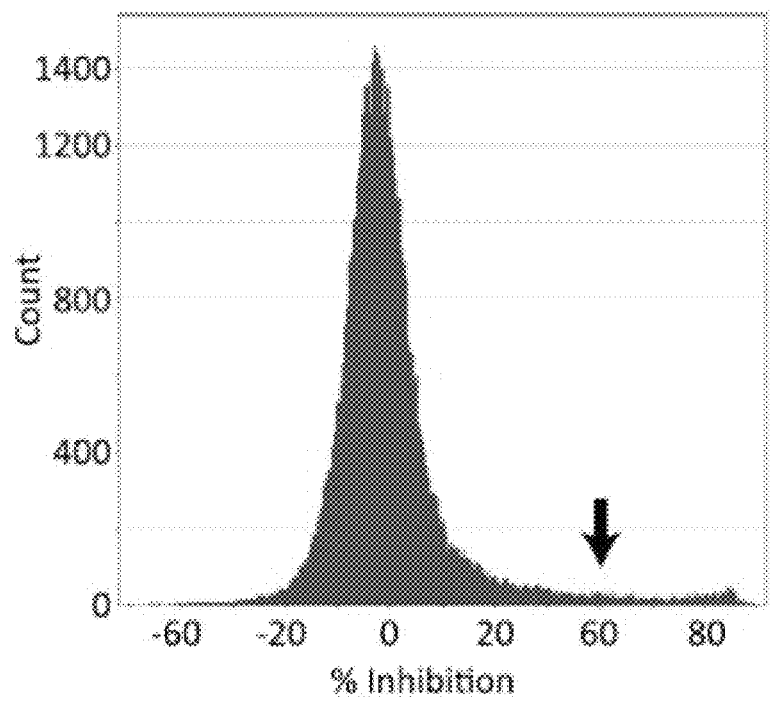
Figure 11:
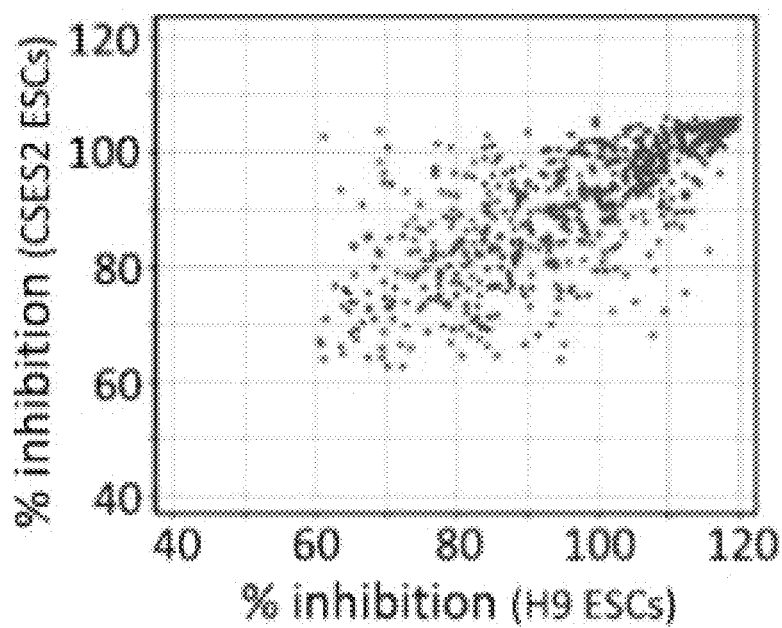
Figure 12A:
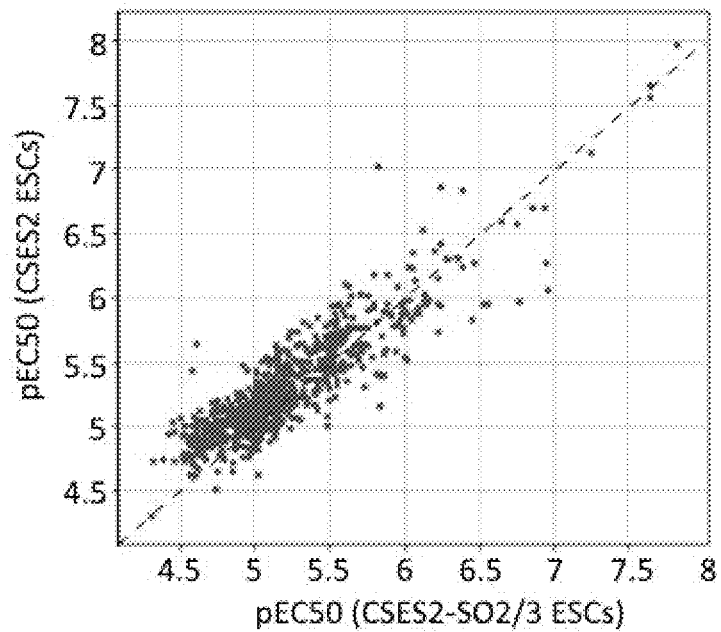
Figure 12B:
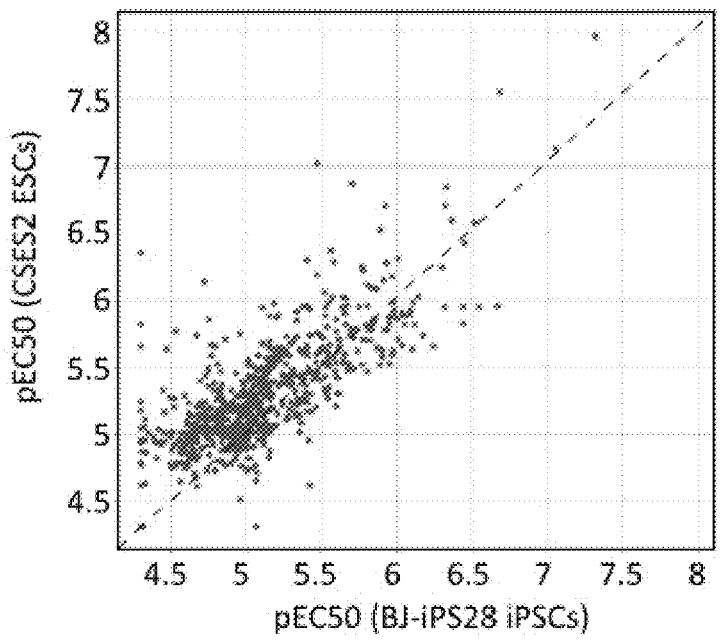
Figure 12C:
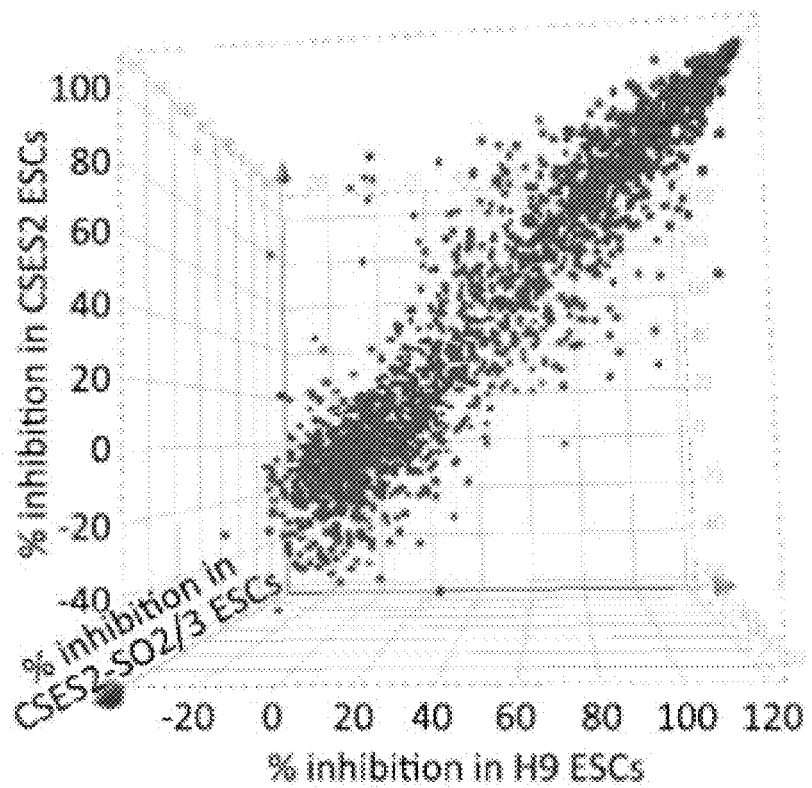
Figure 13:
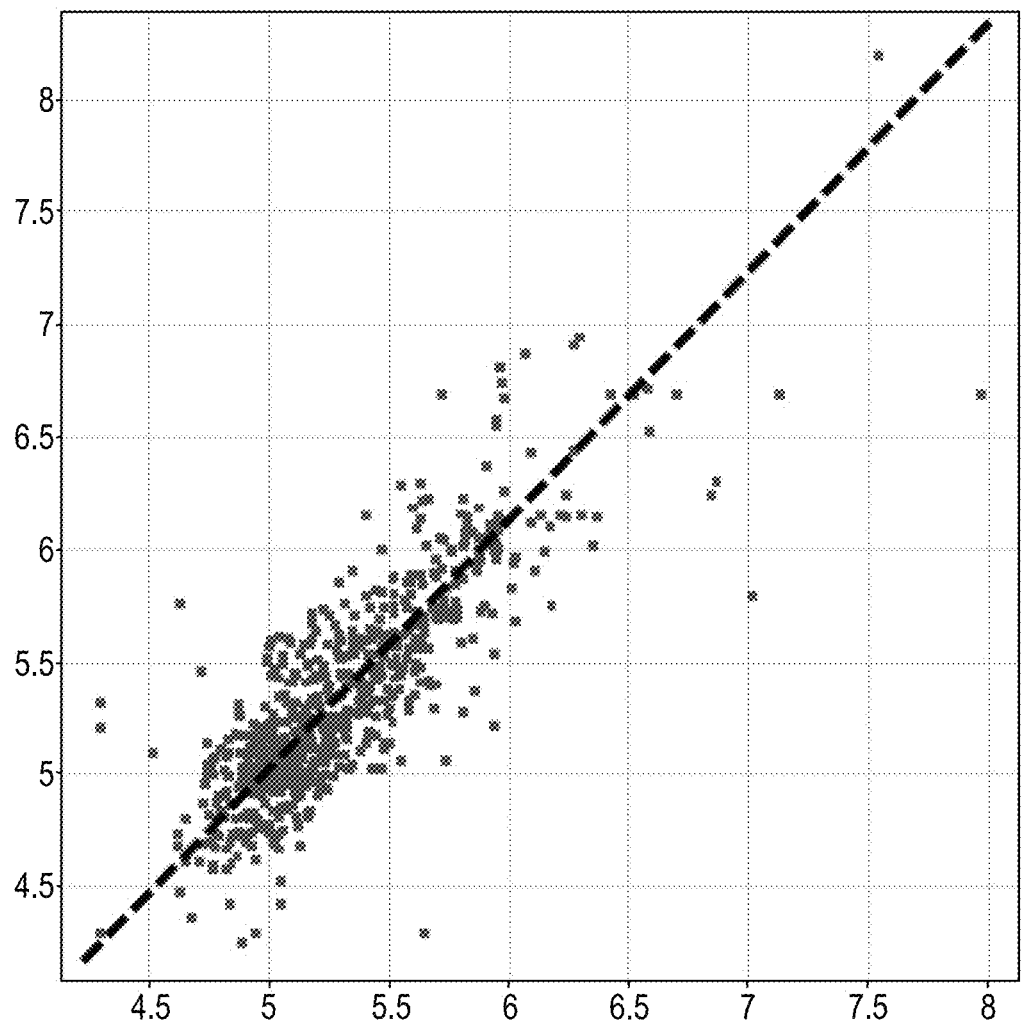
Figure 14:
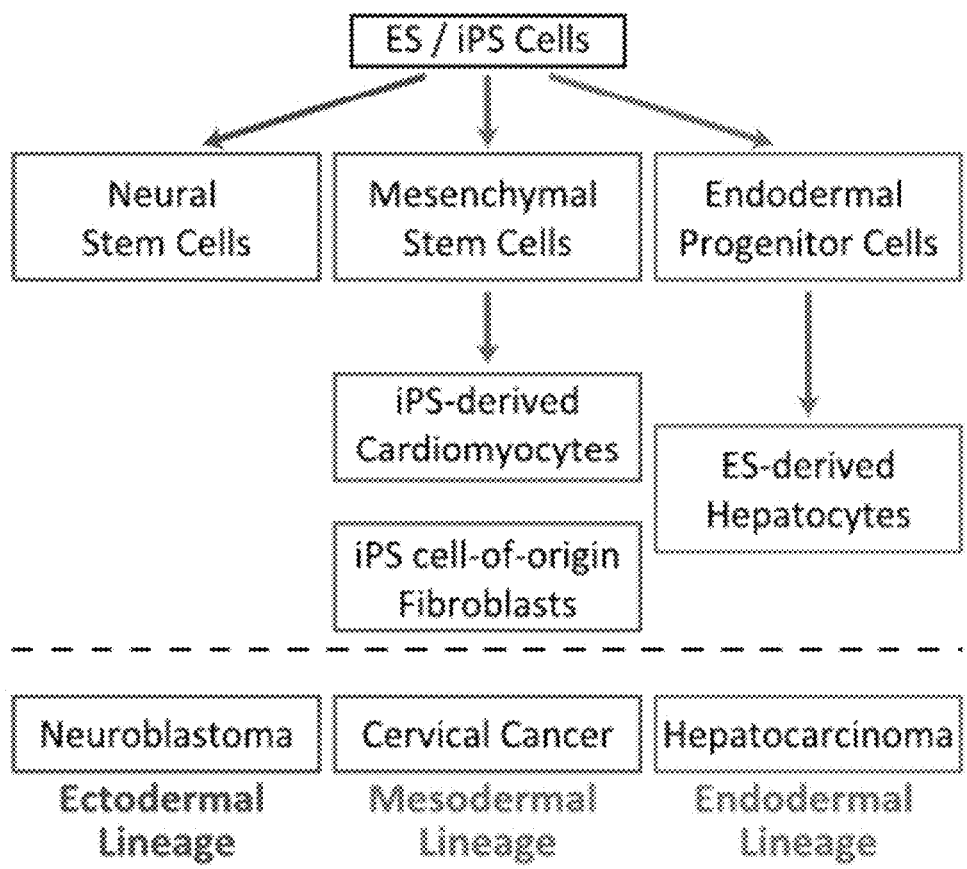
Figure 15:
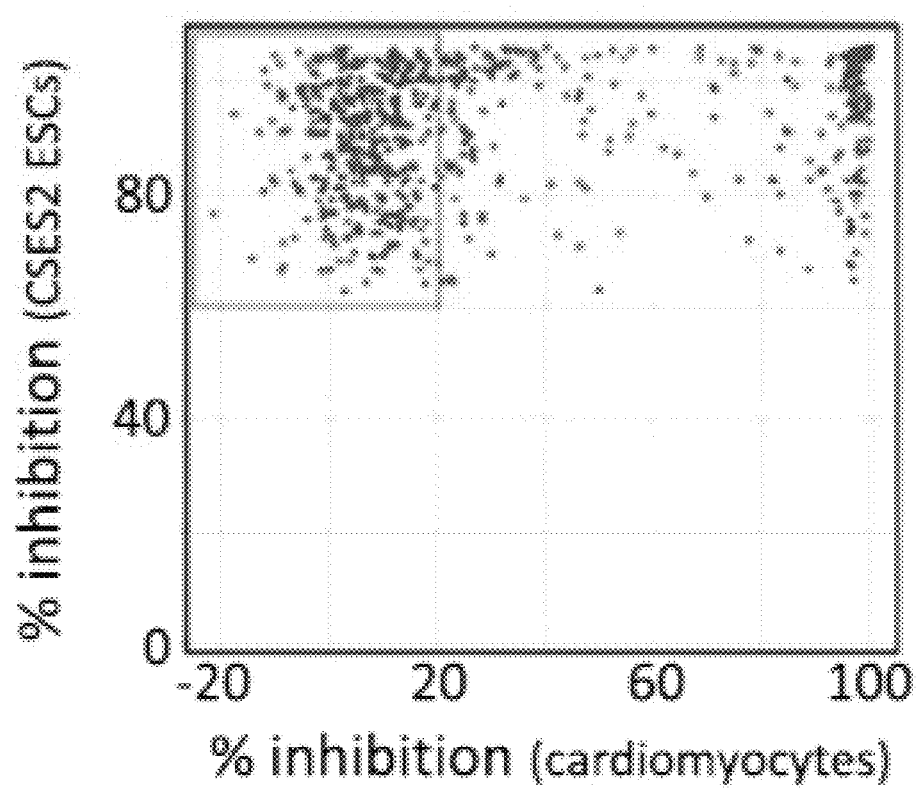
Figure 16:
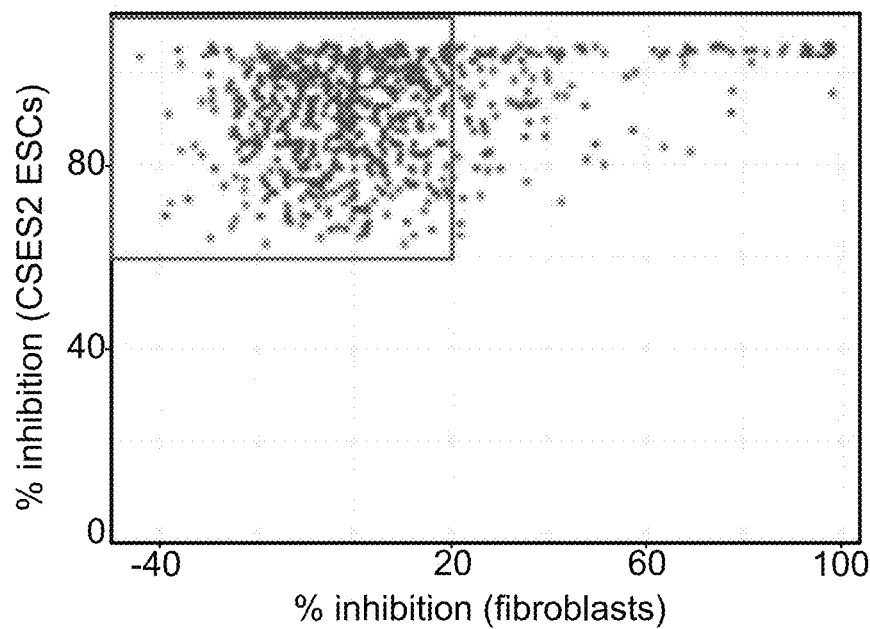
Figure 17:
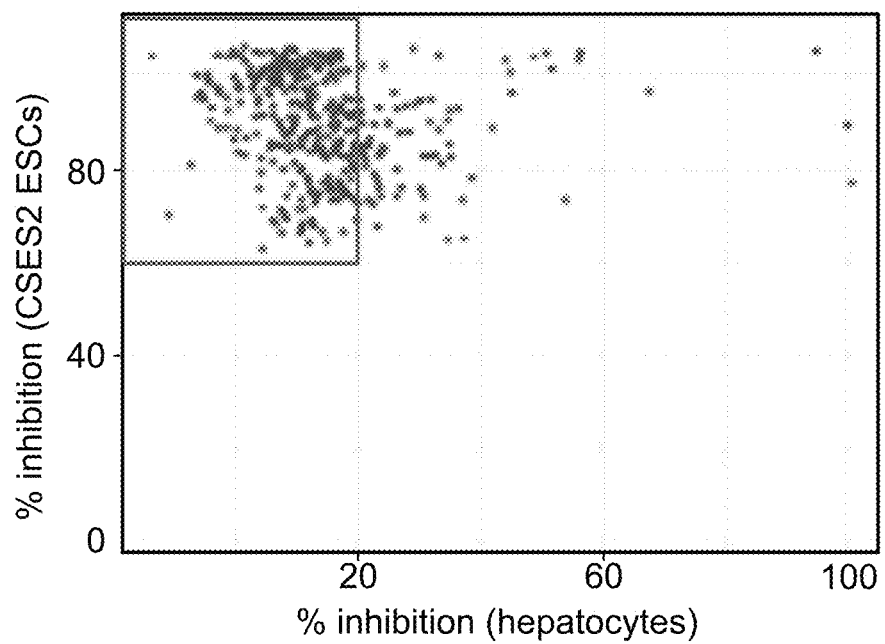
Figure 18:
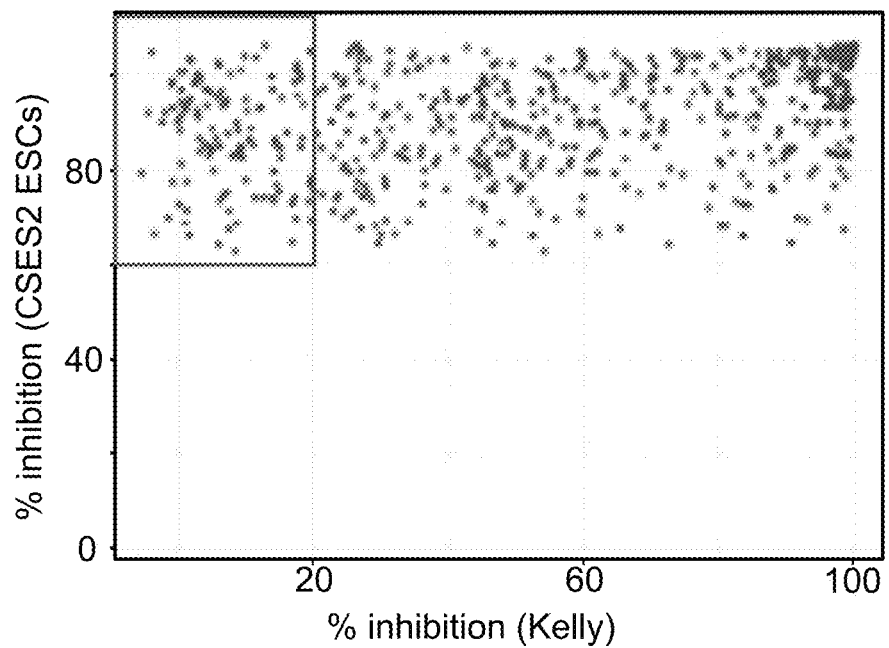
Figure 19:
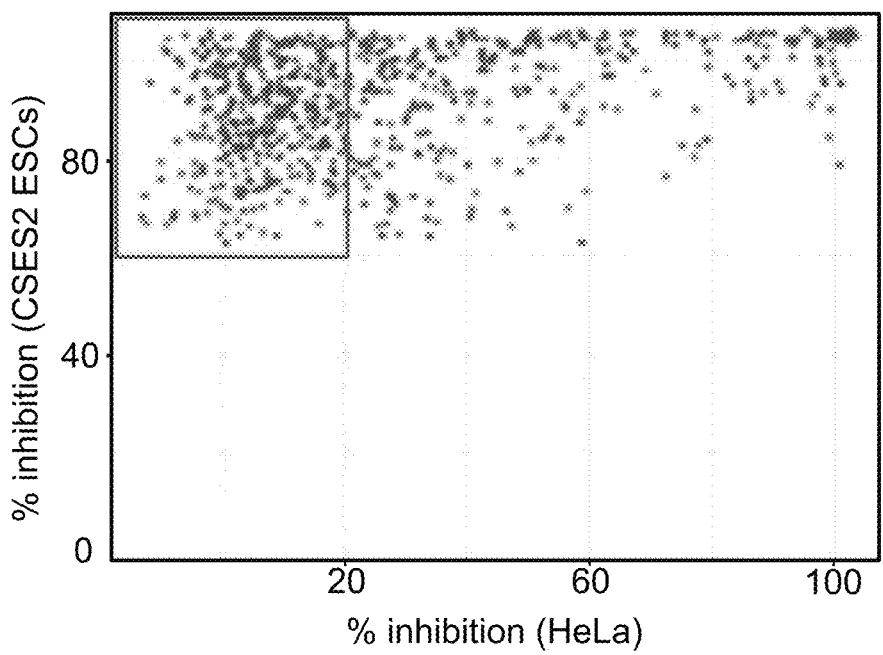
Figure 20:
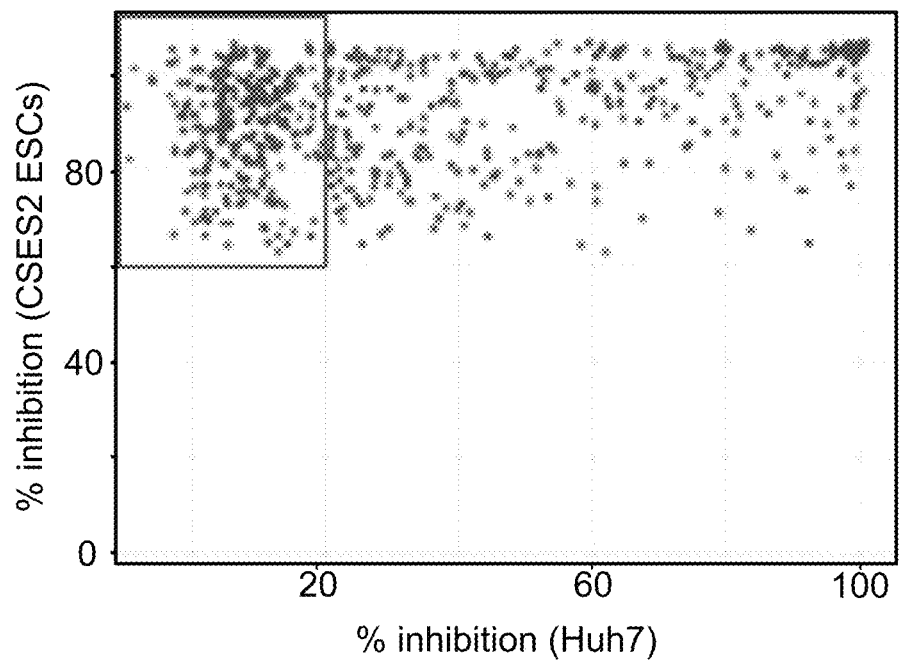
Figure 21:
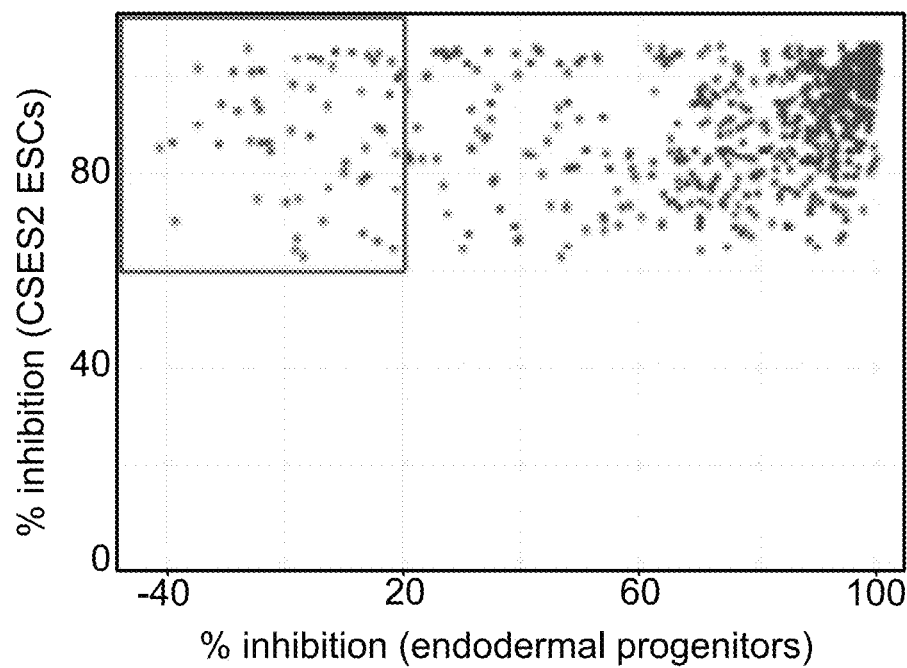
Figure 22:
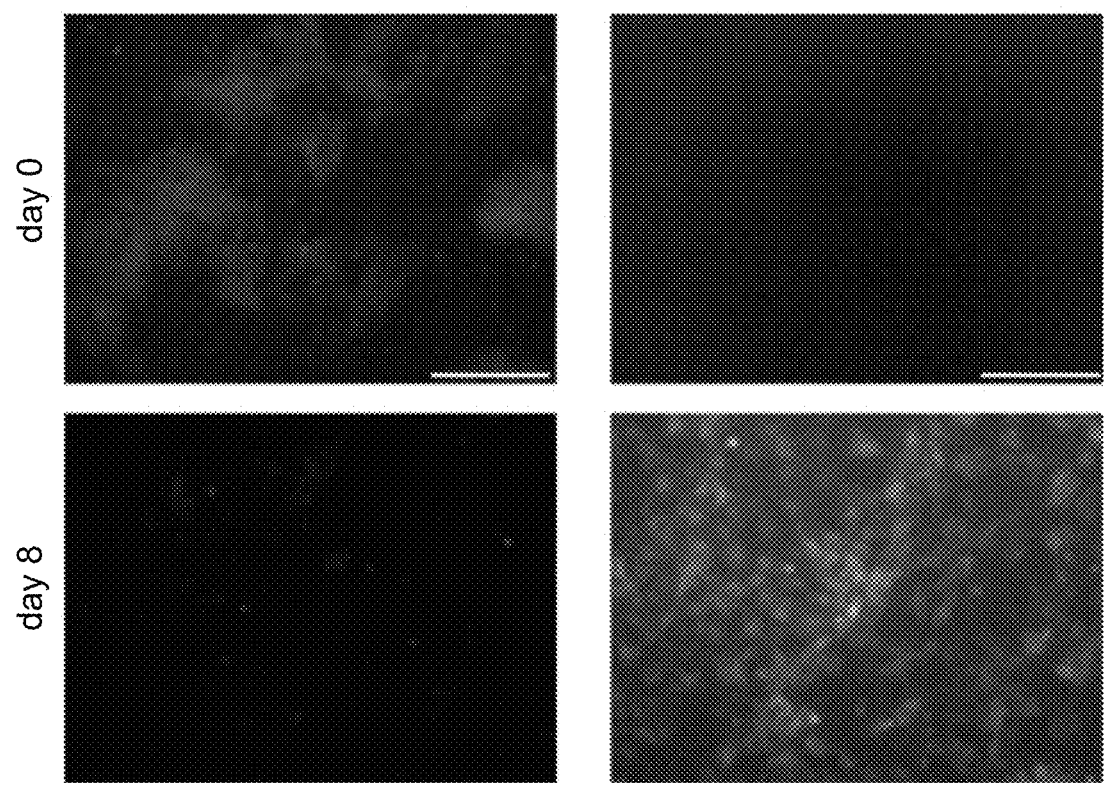
Figure 23:
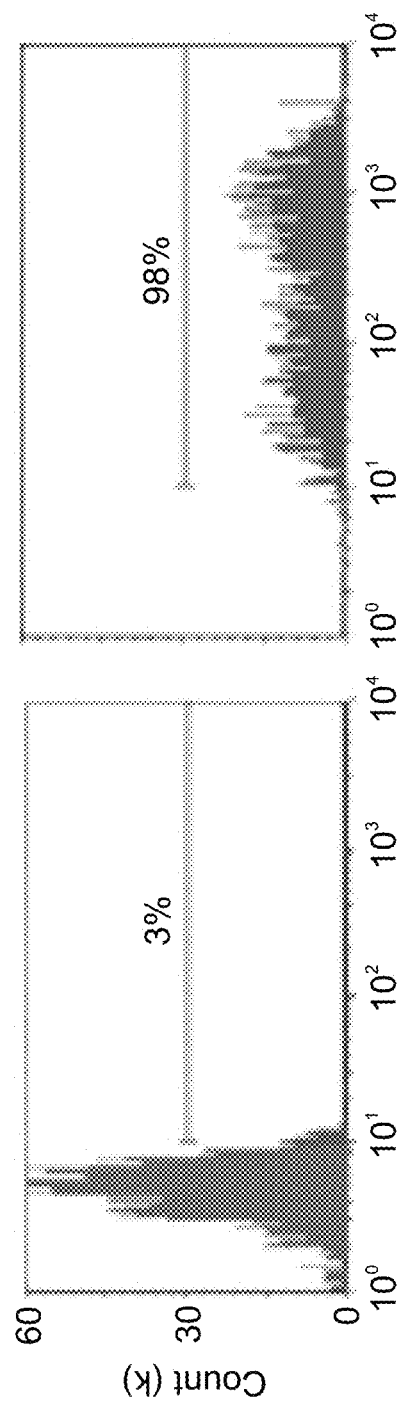
Figure 24:
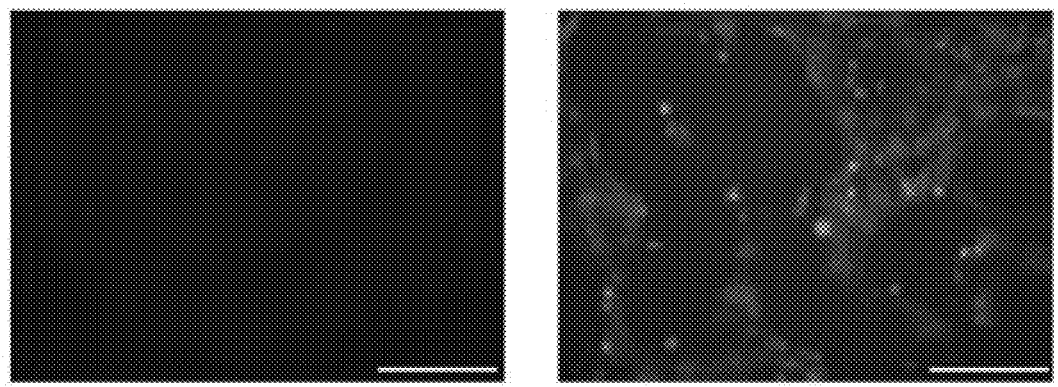
Figure 25A:
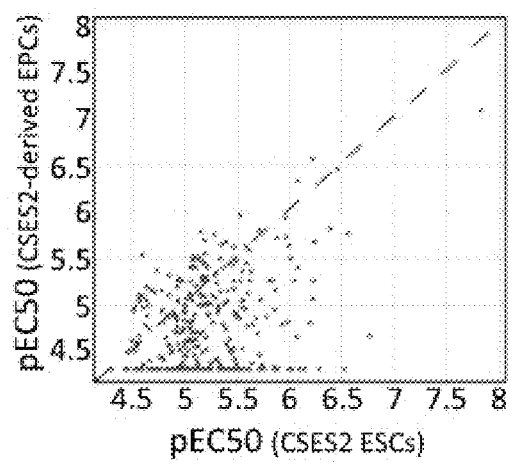
Figure 25B:
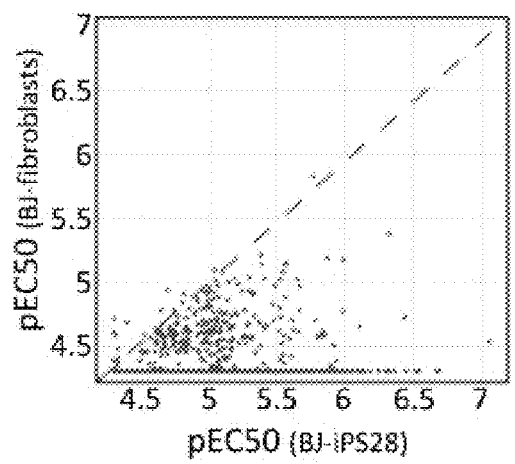
Figure 26A:
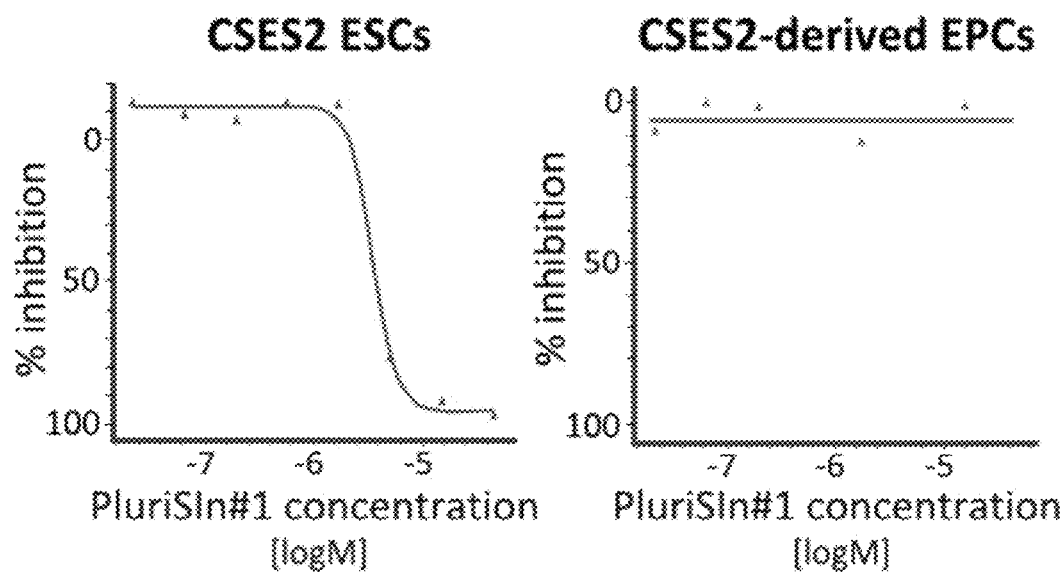
Figure 26B:
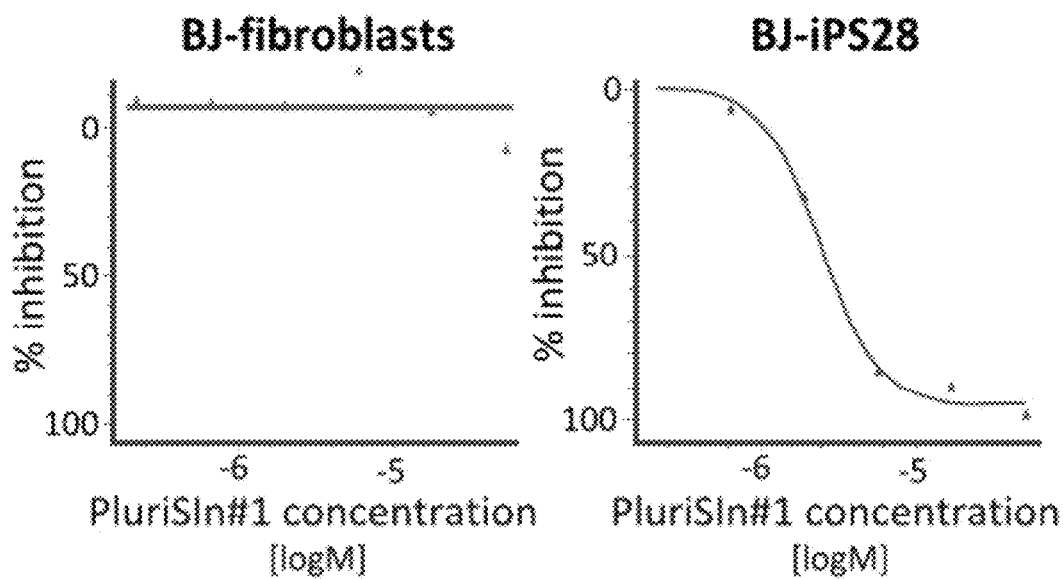
Figure 27:
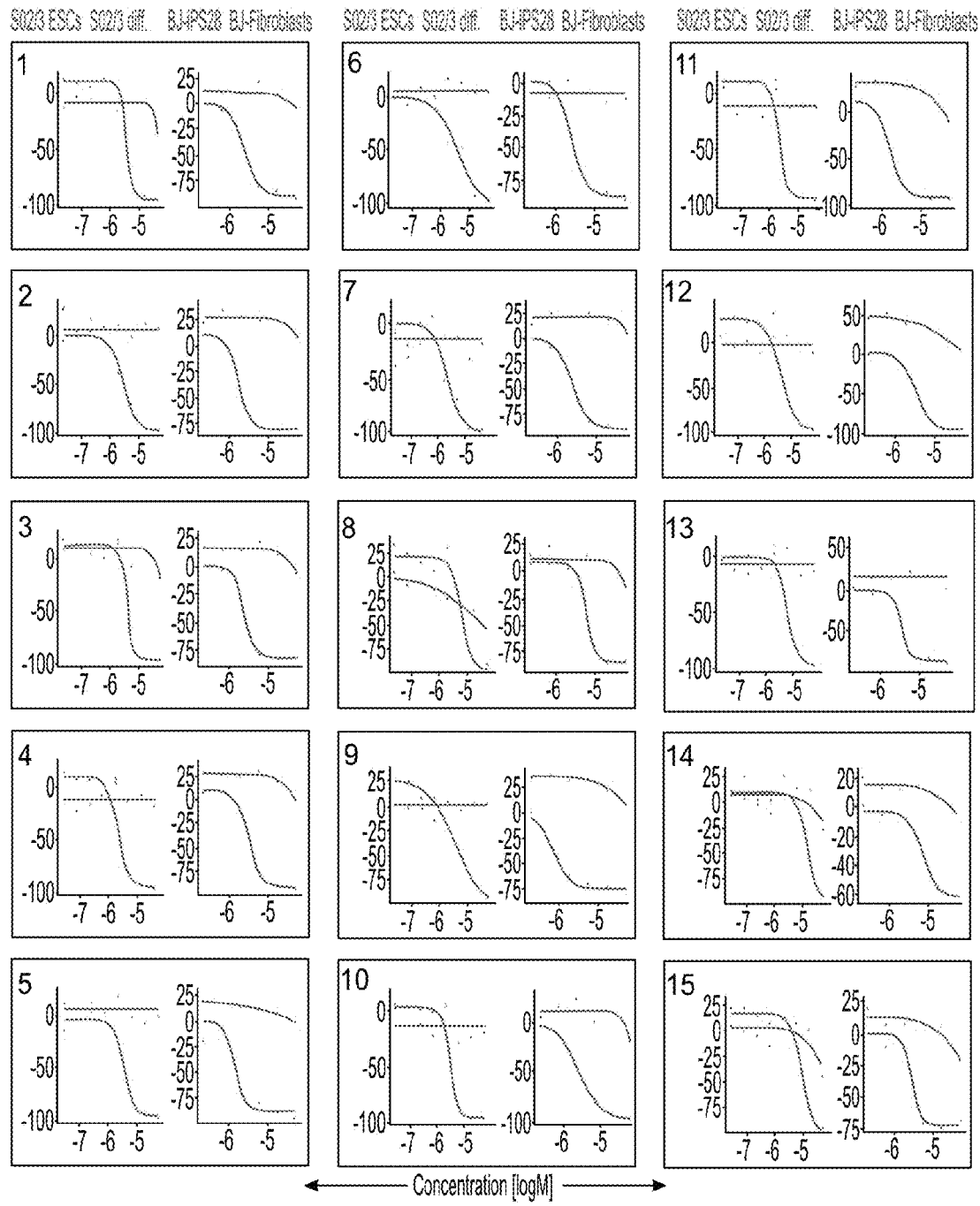
Figure 28:
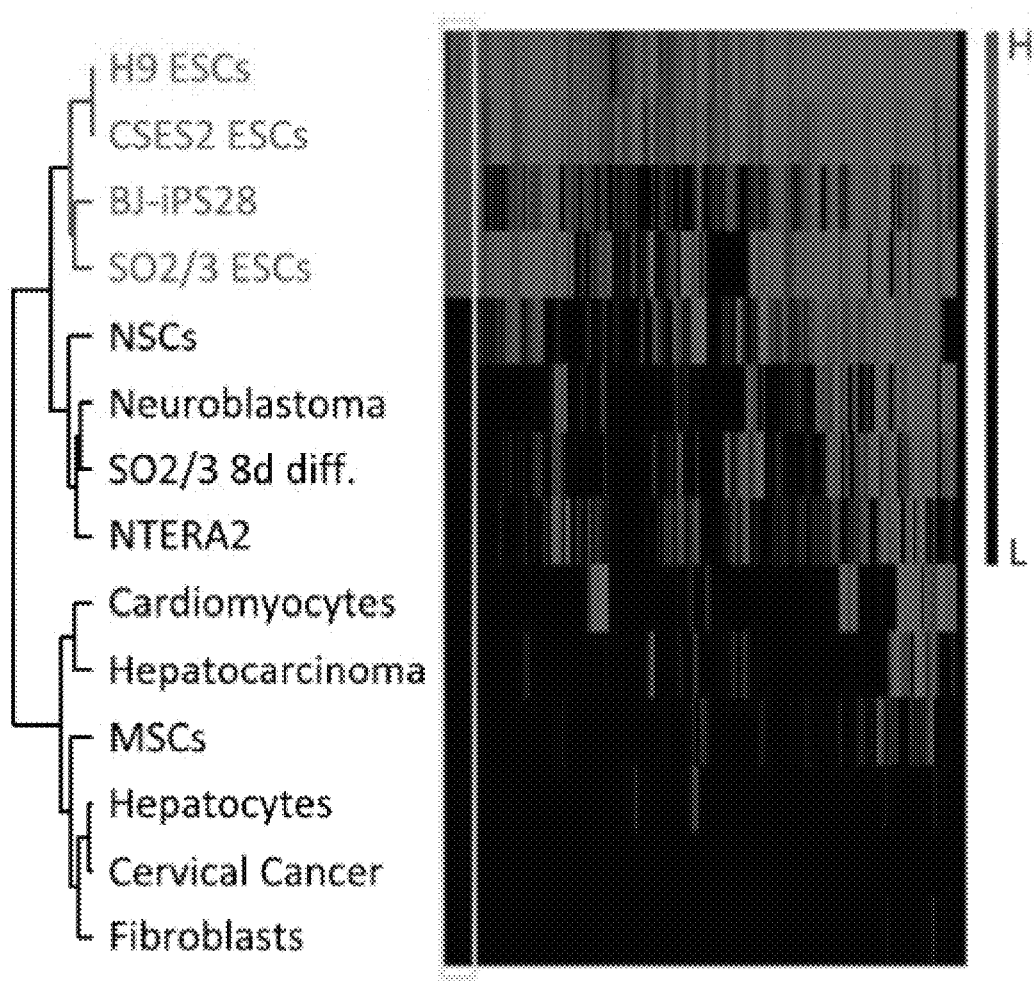
Figure 29:
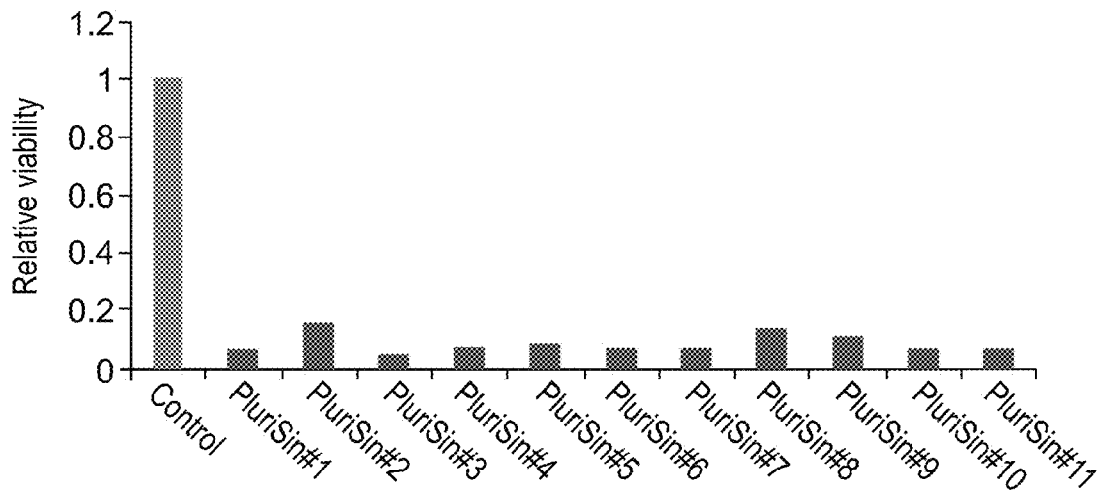
Figure 30:
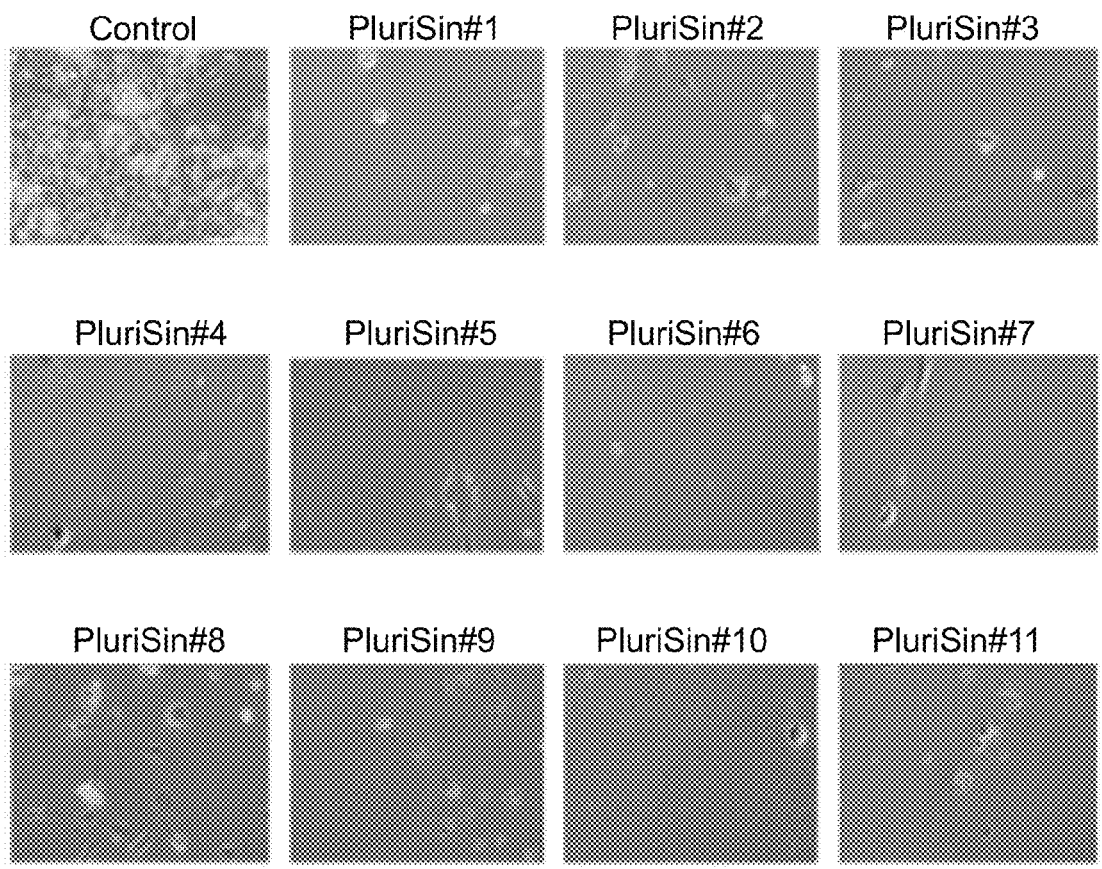
Figure 31:
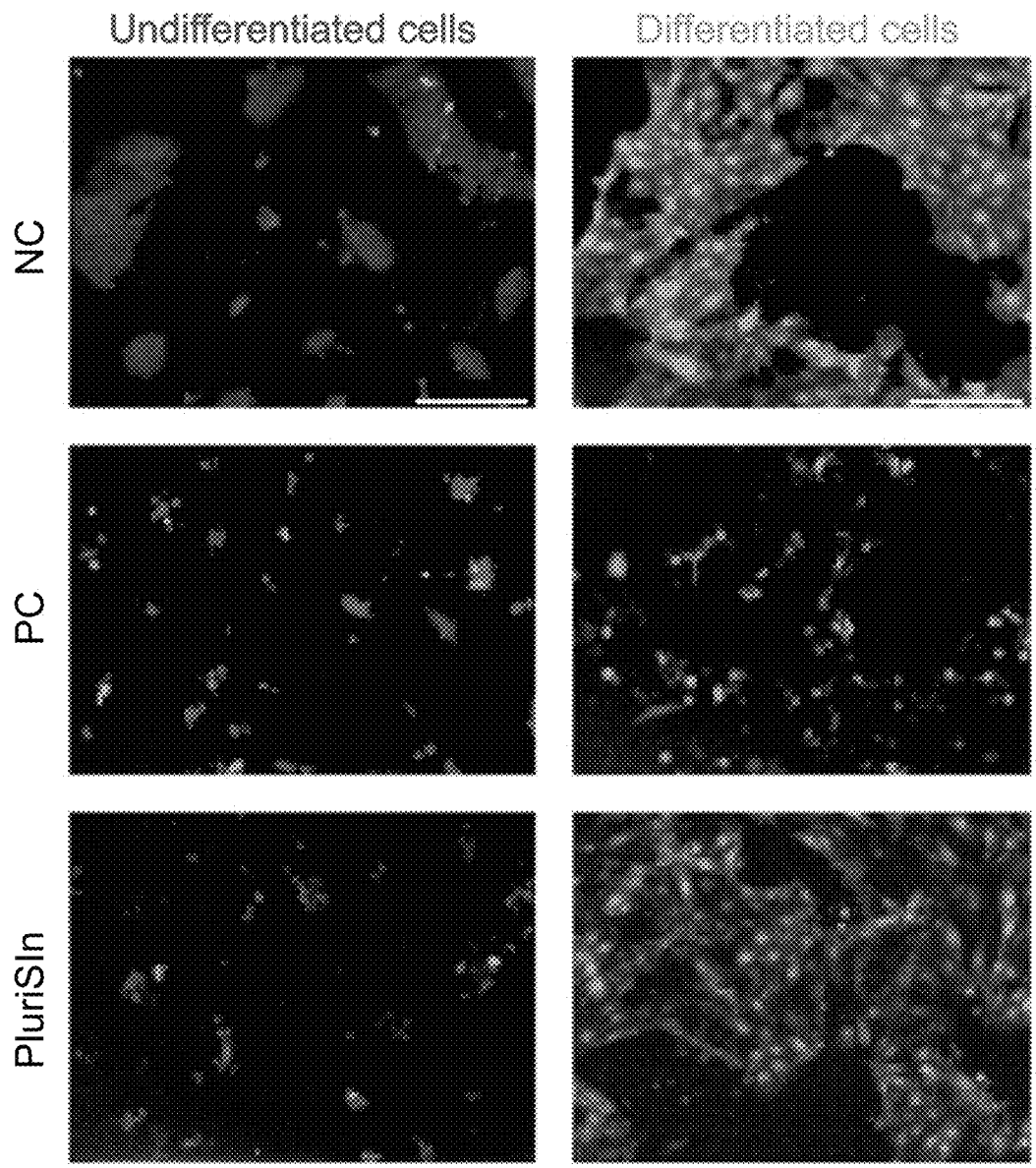
Figure 32A:
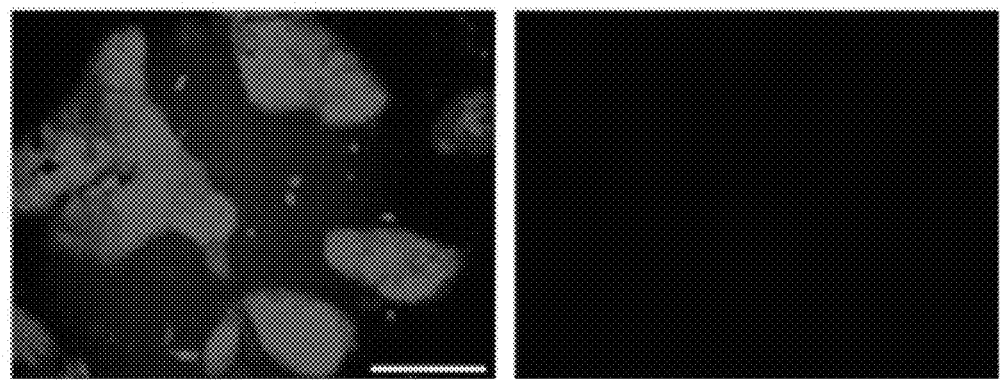
Figure 32B:
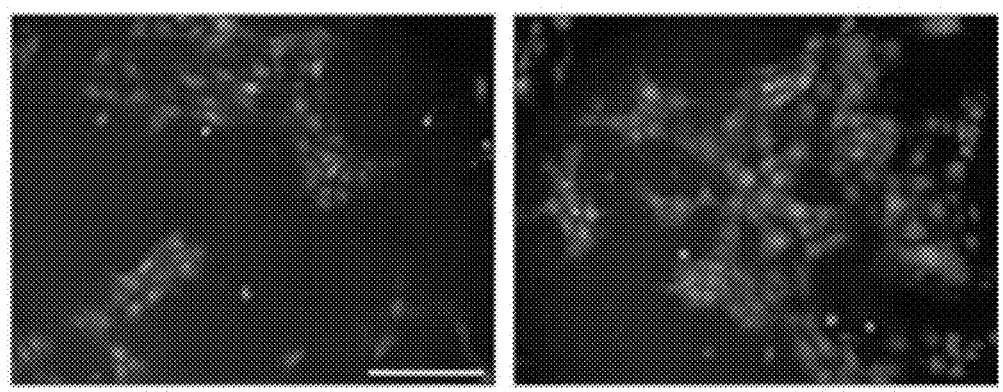
Figure 32C:
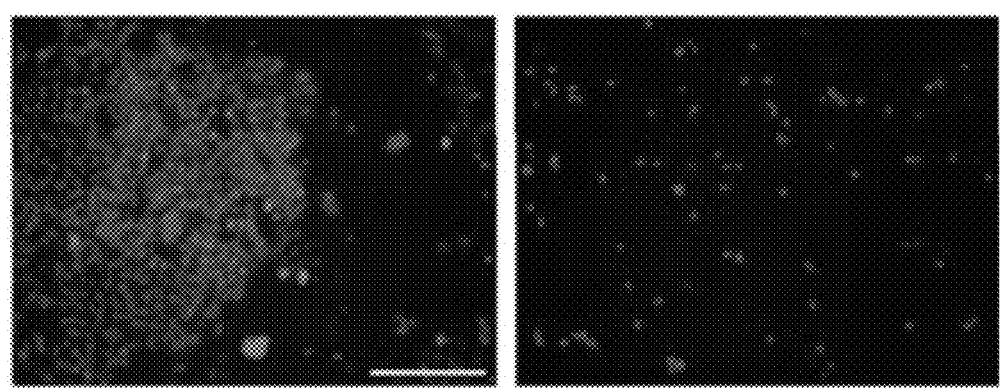
Figure 33:
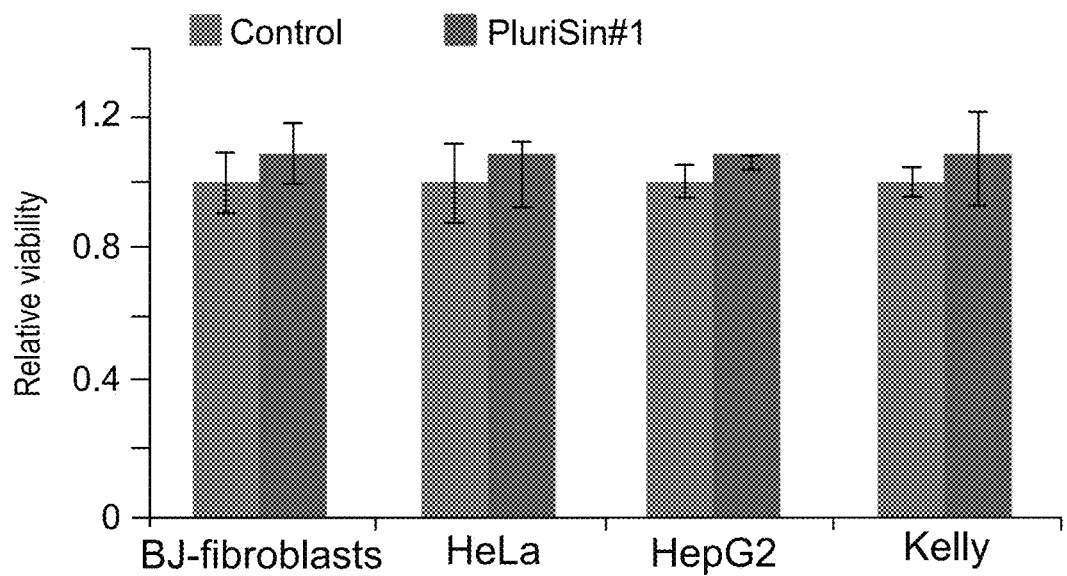
Figure 34:
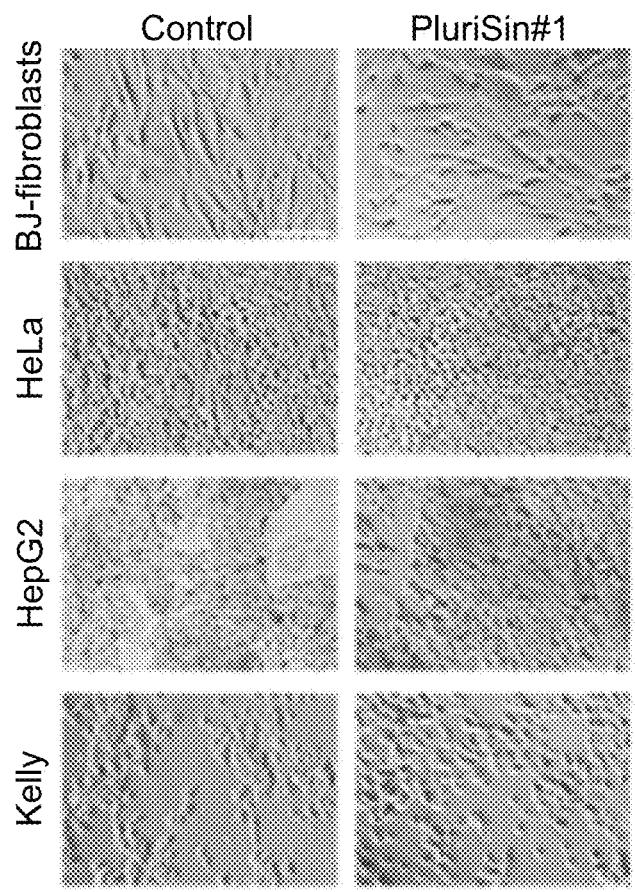
Figure 35:
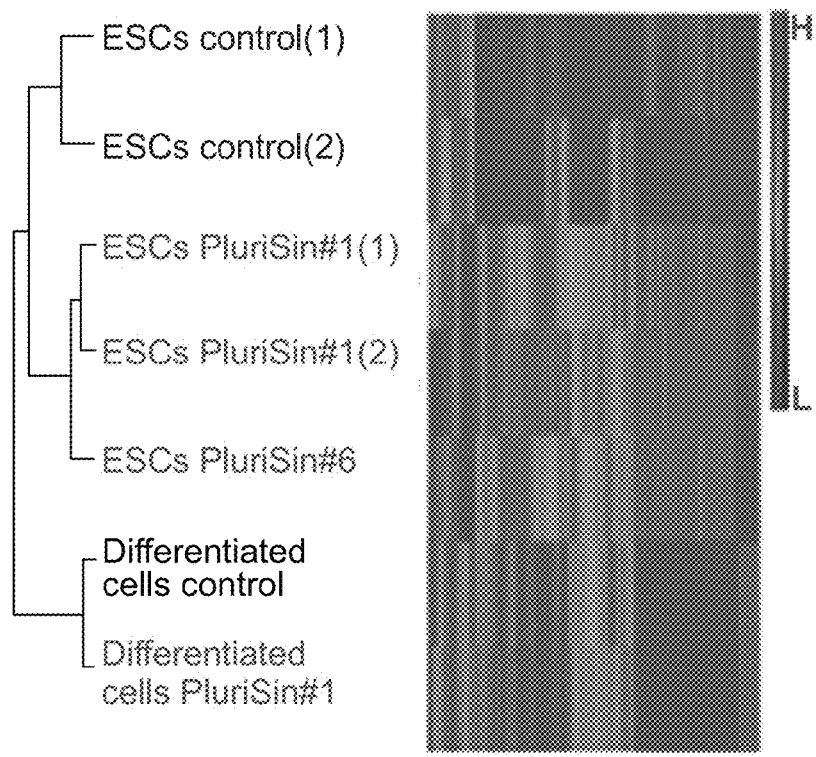
Figure 36:
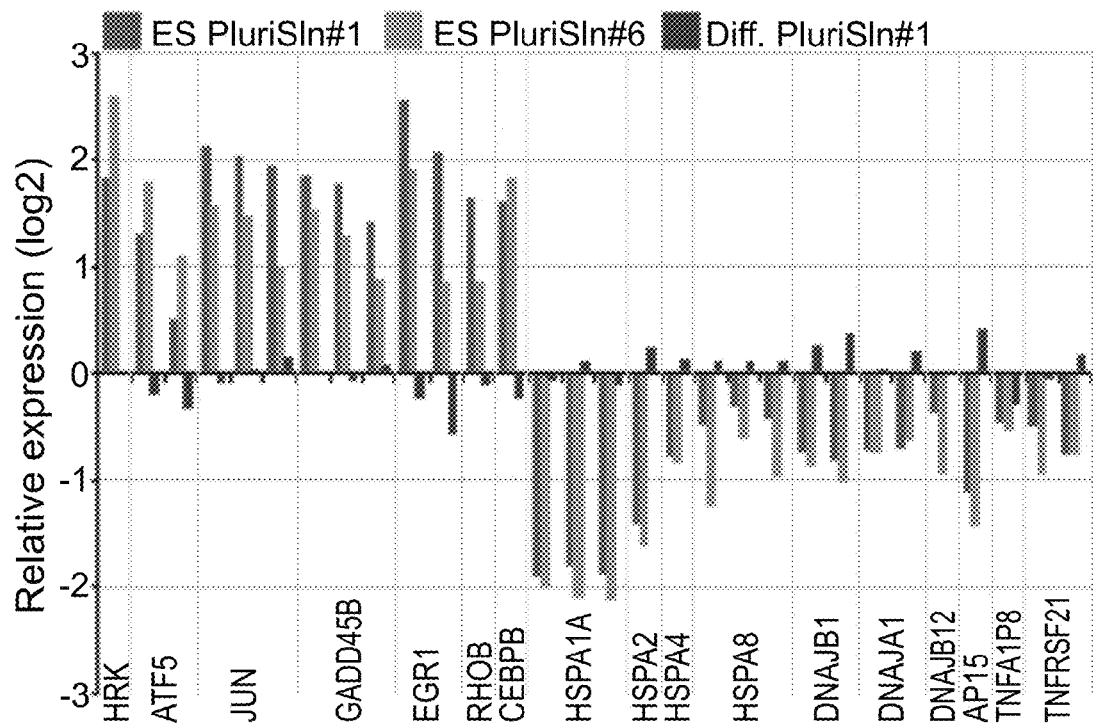
Figure 37A:
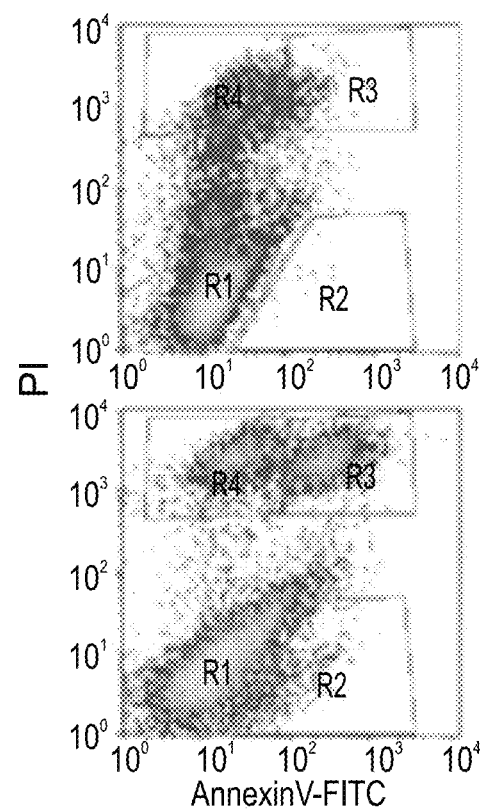
Figure 37B:
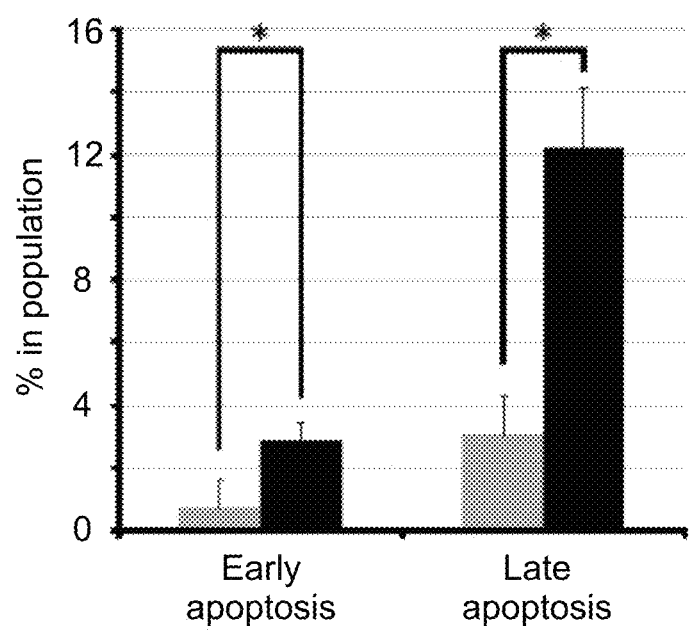
Figure 38:
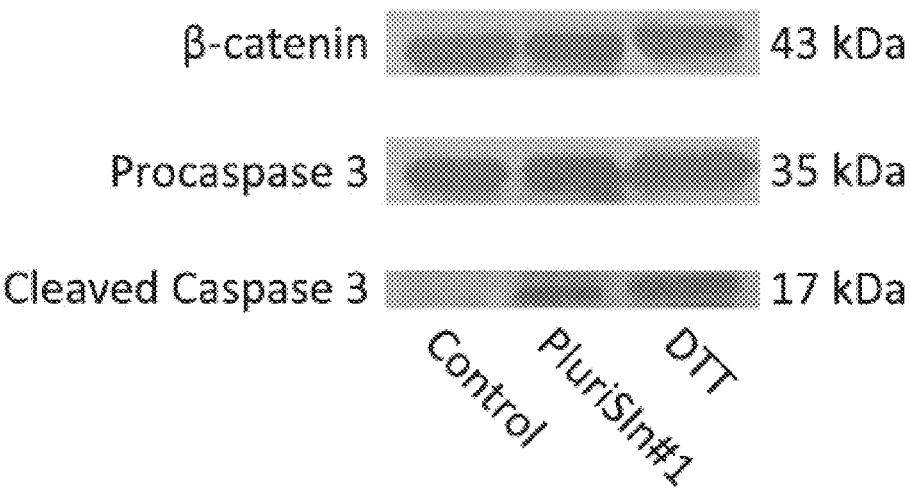
Figure 39:
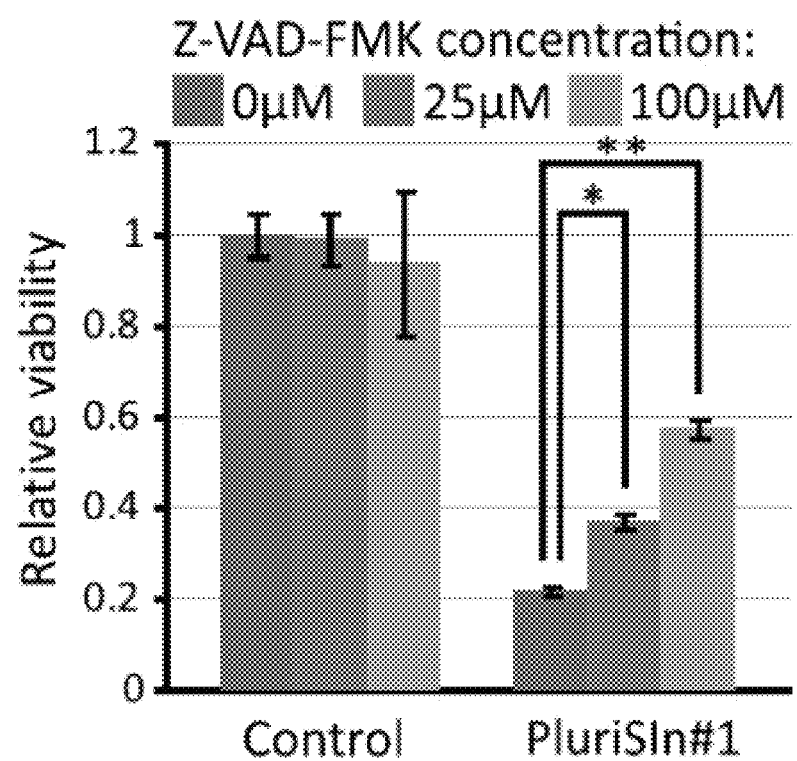
Figure 40:
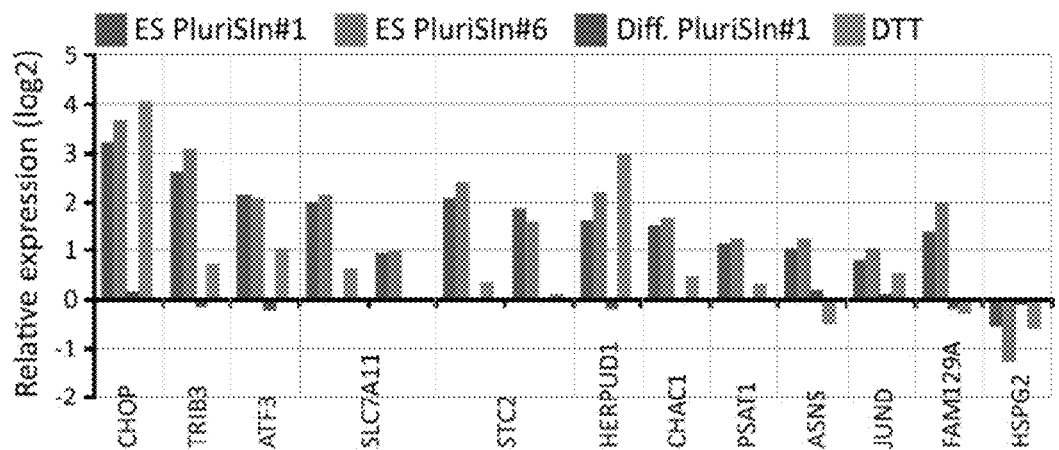
Figure 41:
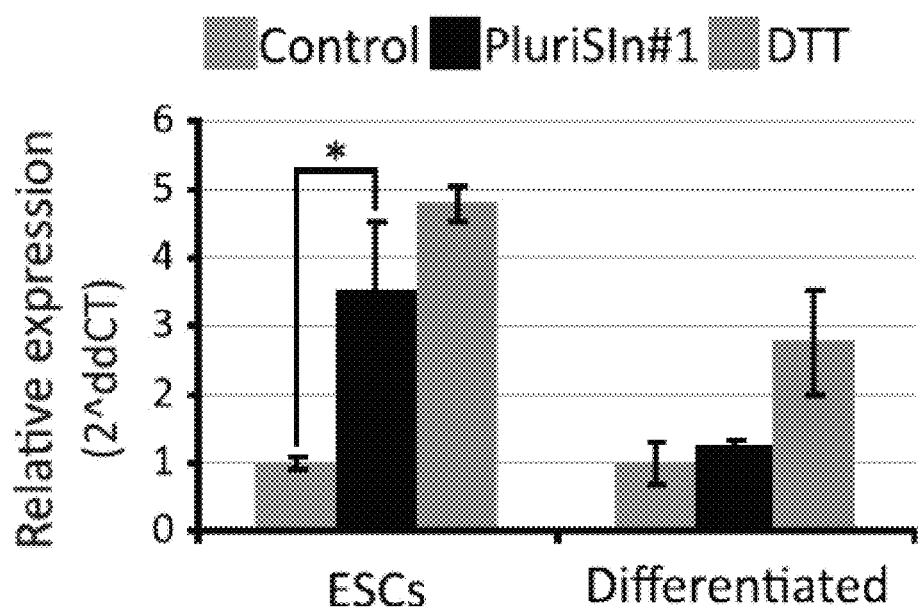
Figure 42:
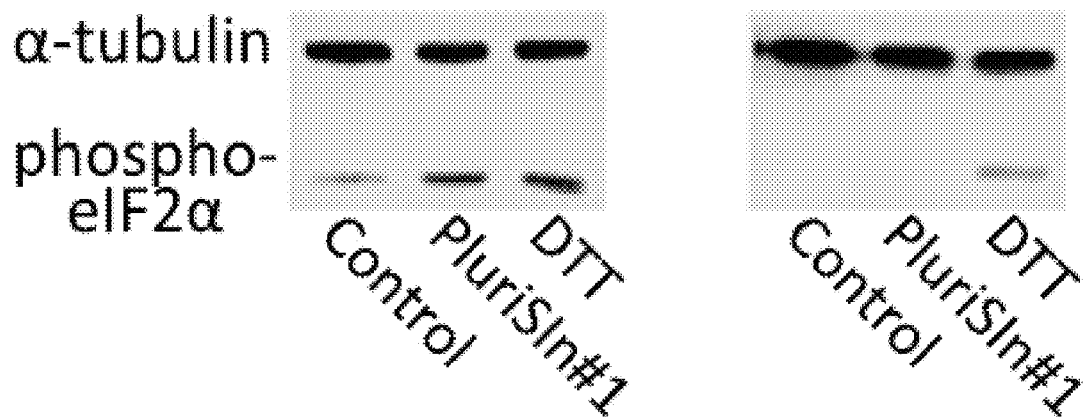
Figure 43:
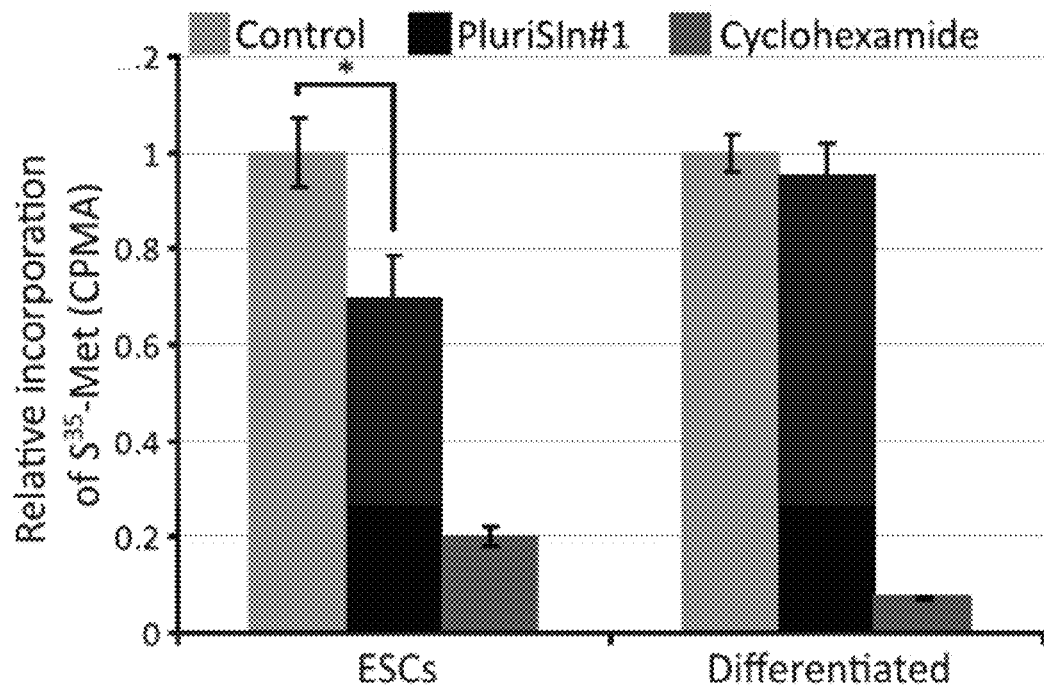
Figure 44:
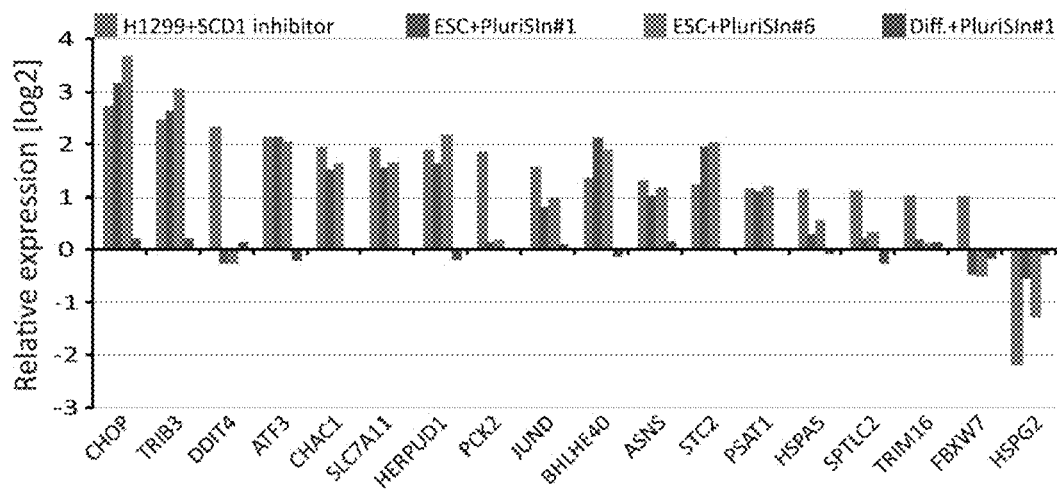
Figure 45:
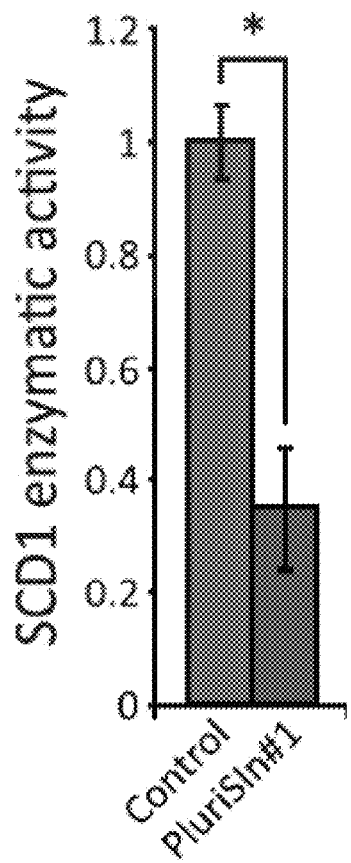
Figure 46:
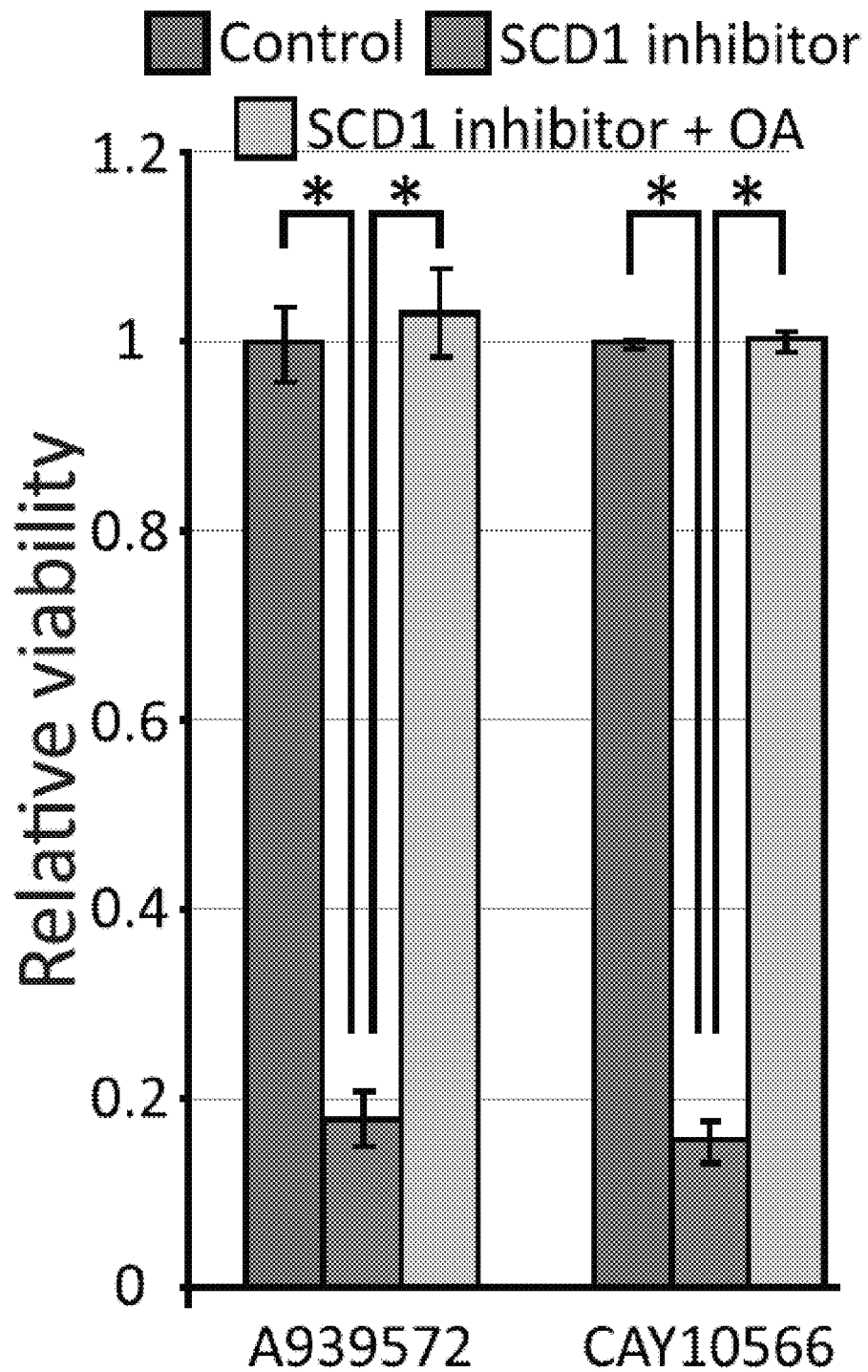
Figure 47:
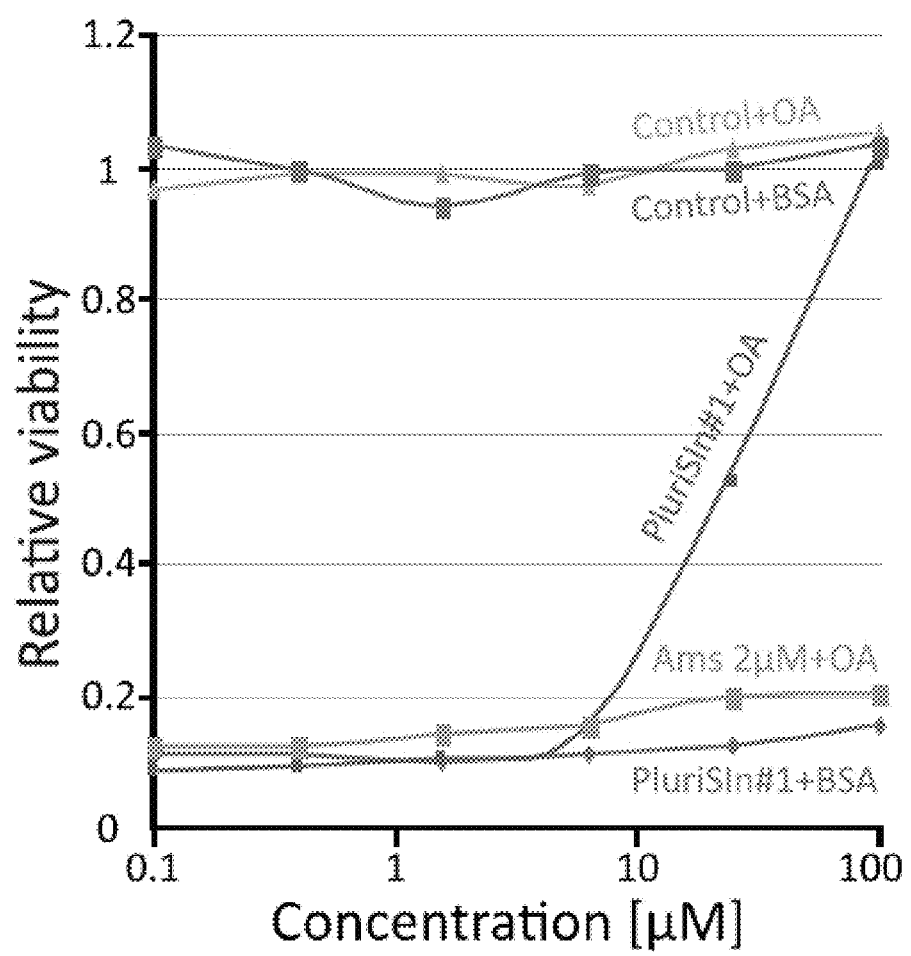
Figure 48:
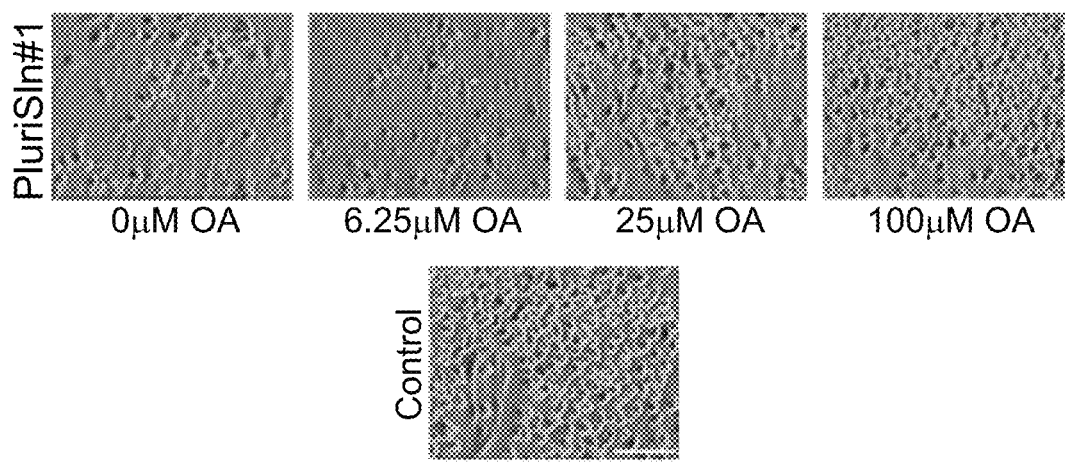
Figure 49:
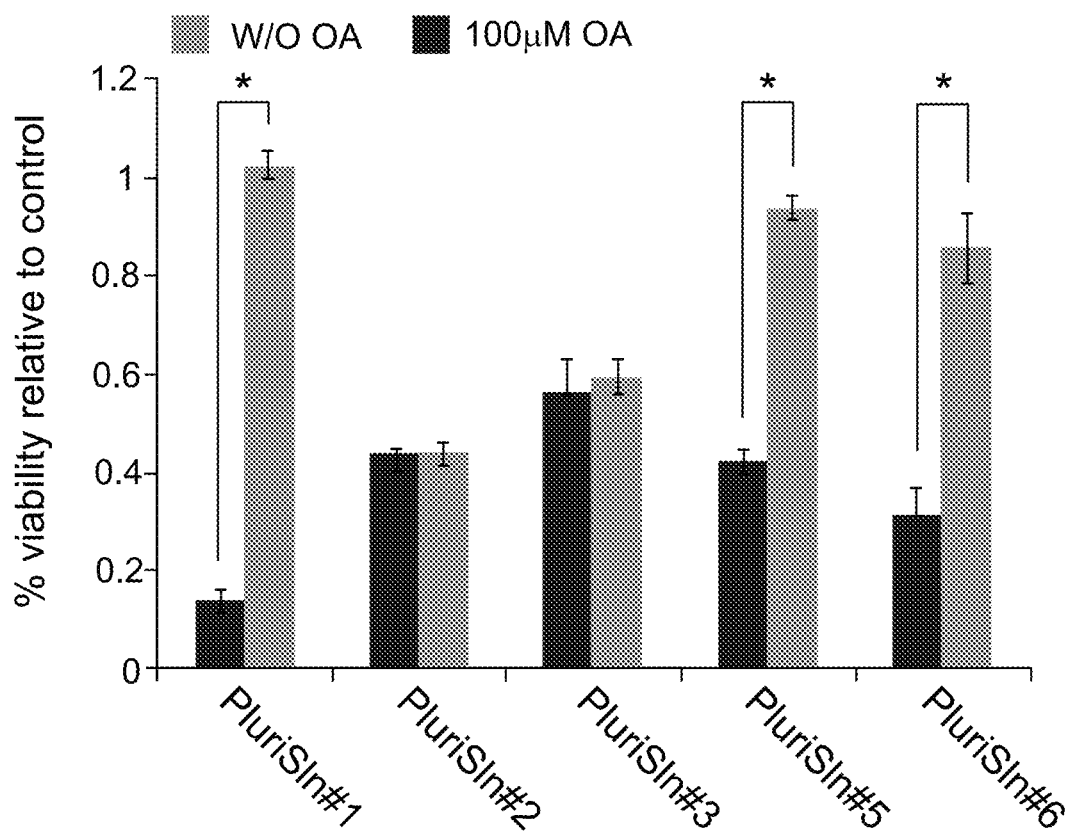
Figure 50:
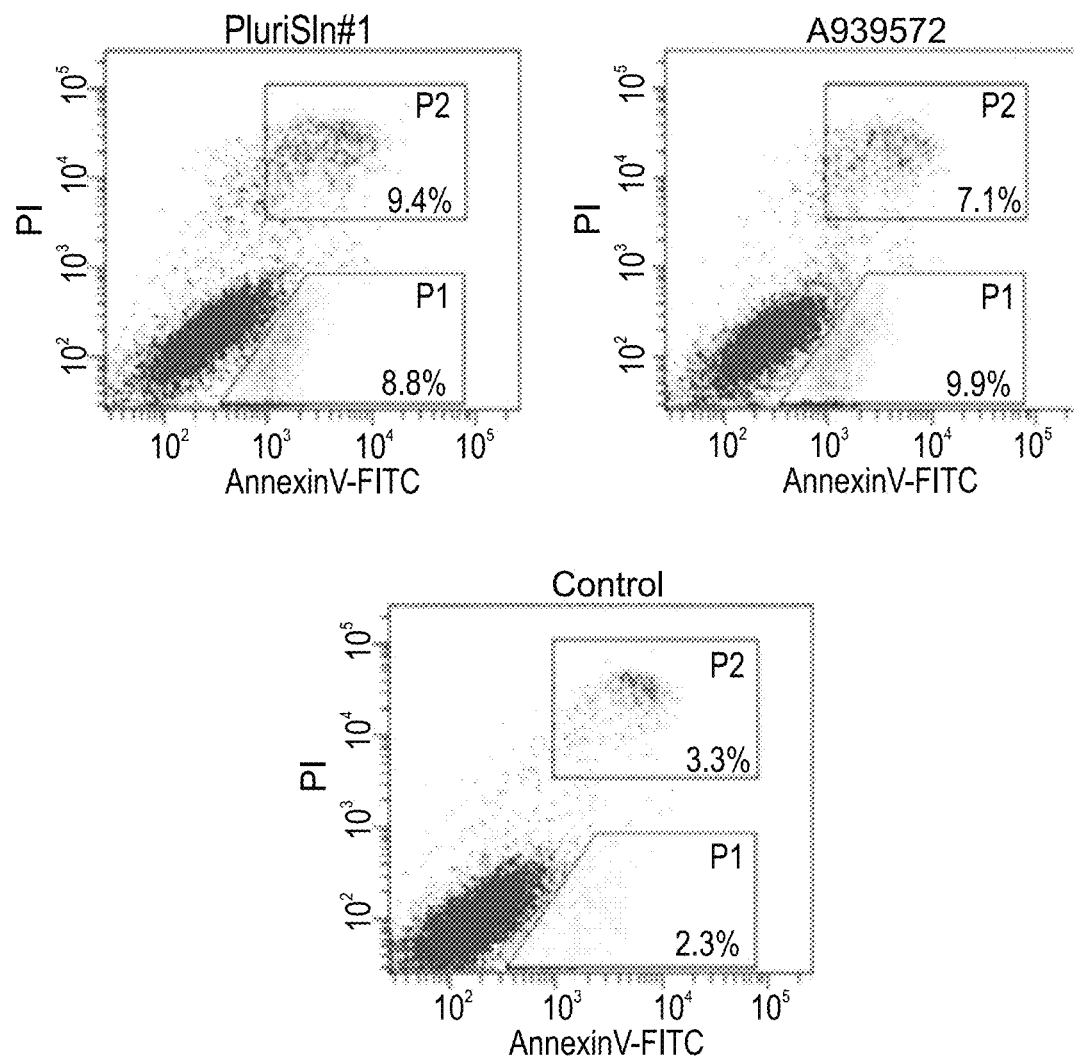
Figure 51:
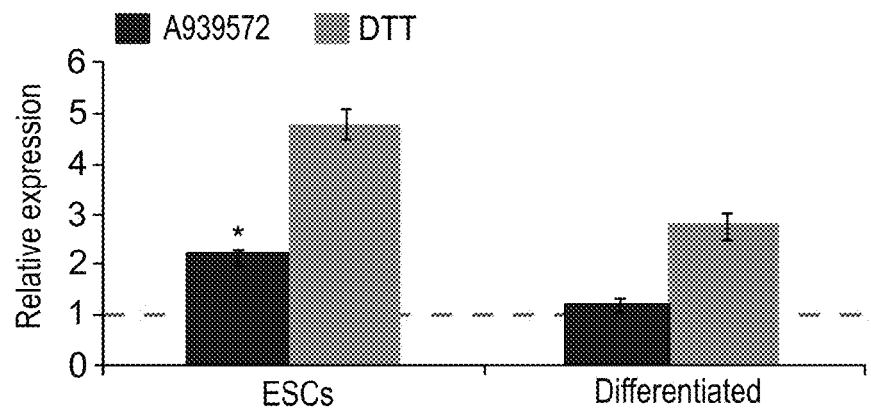
Figure 52:
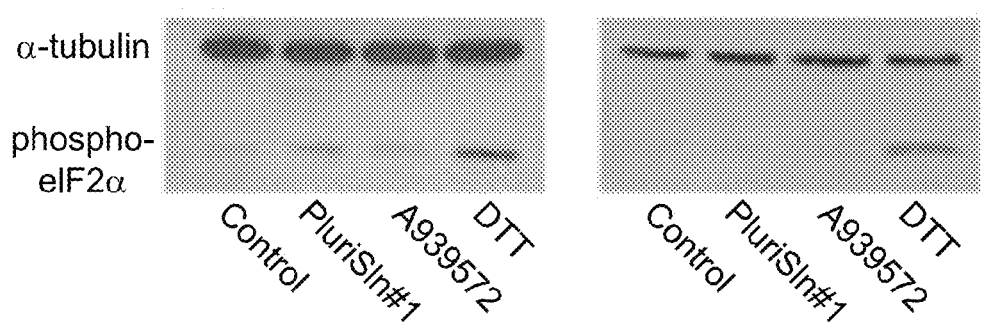
Figure 53:
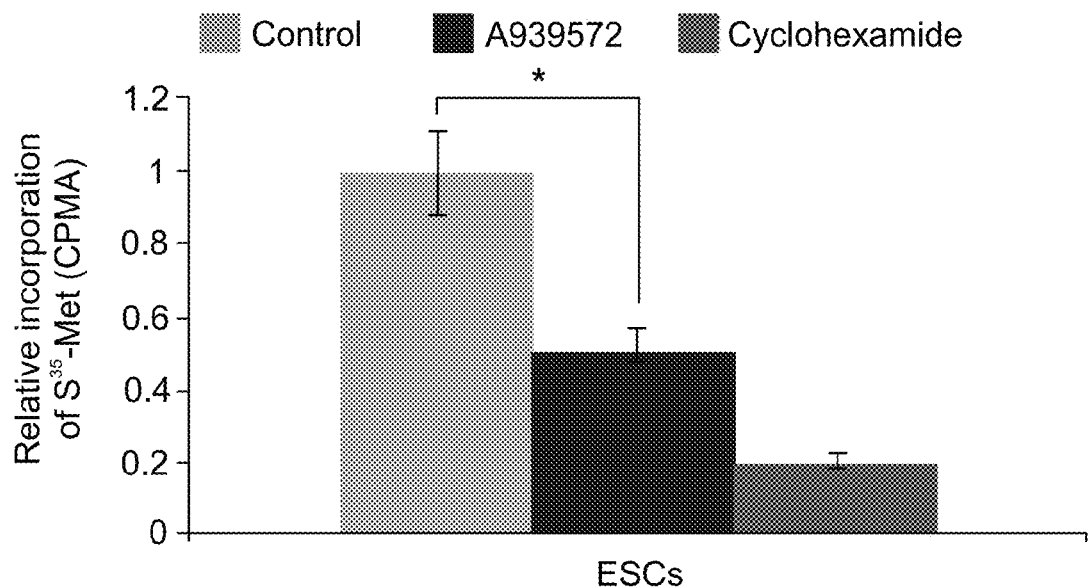
Figure 54:
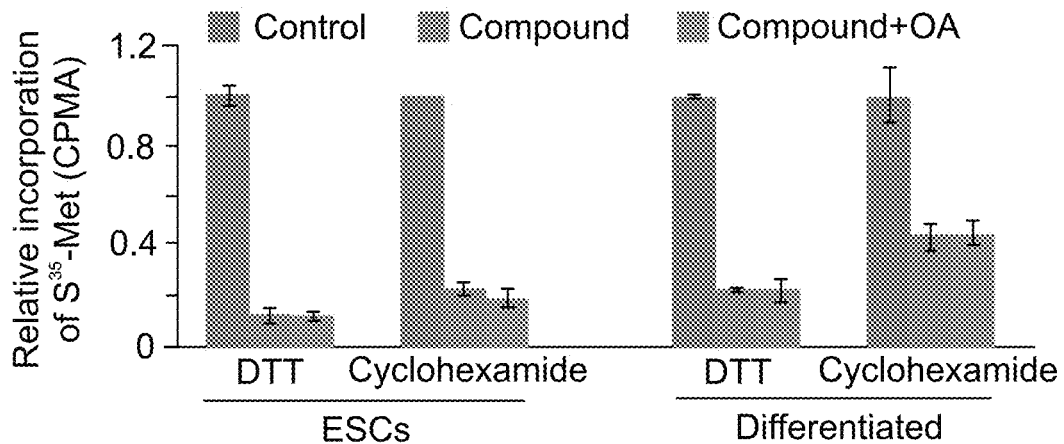
Figure 55:
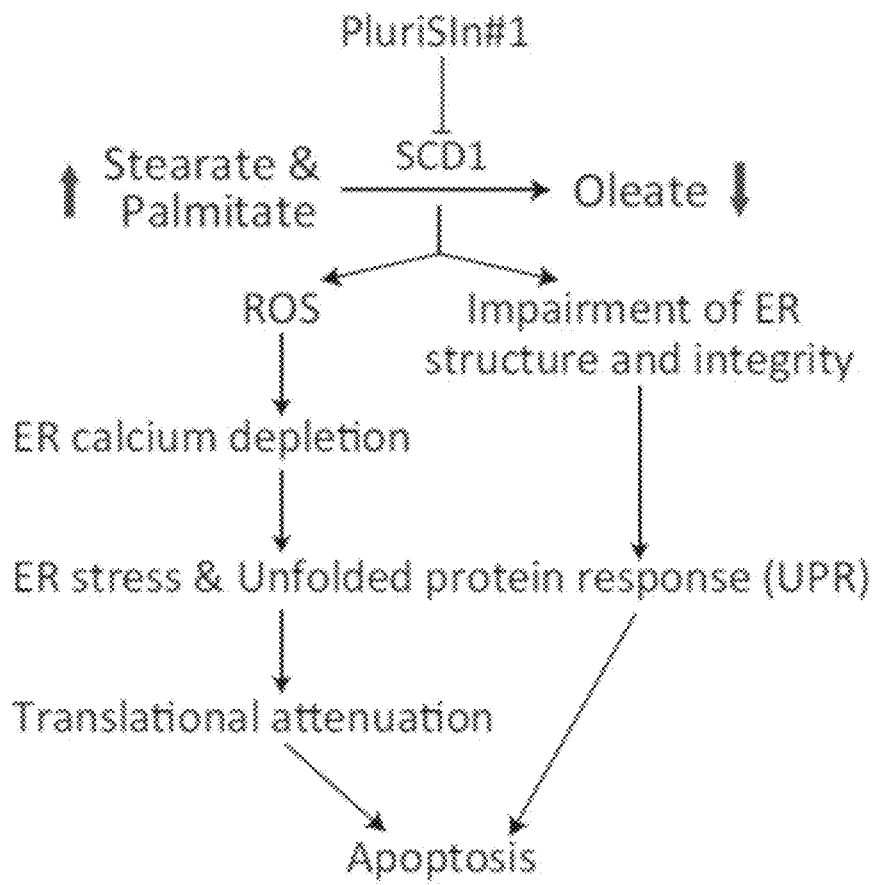
Figure 56:
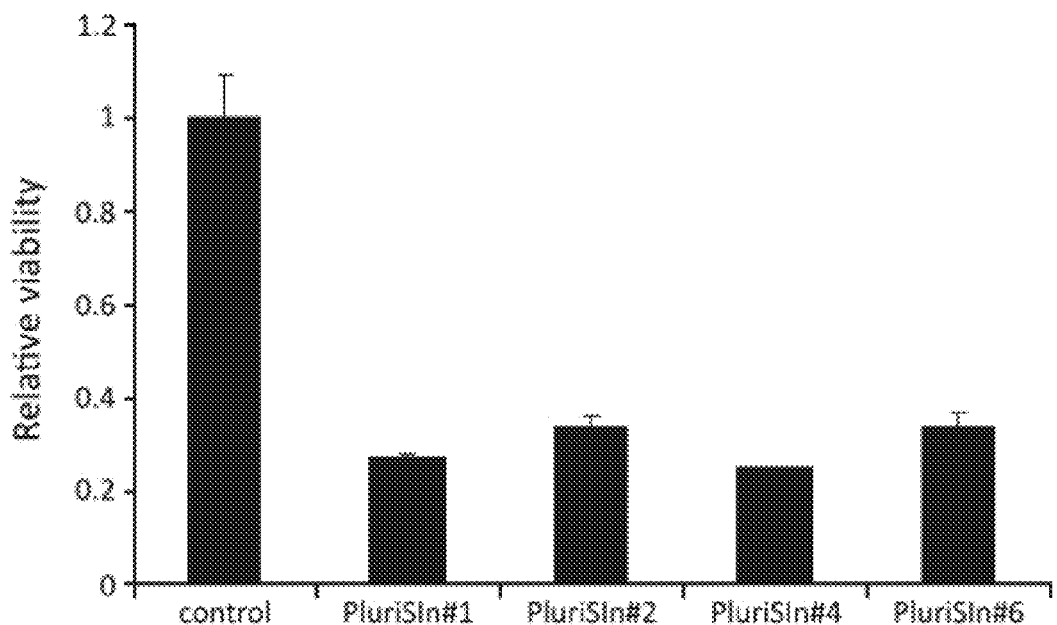
Figure 57:
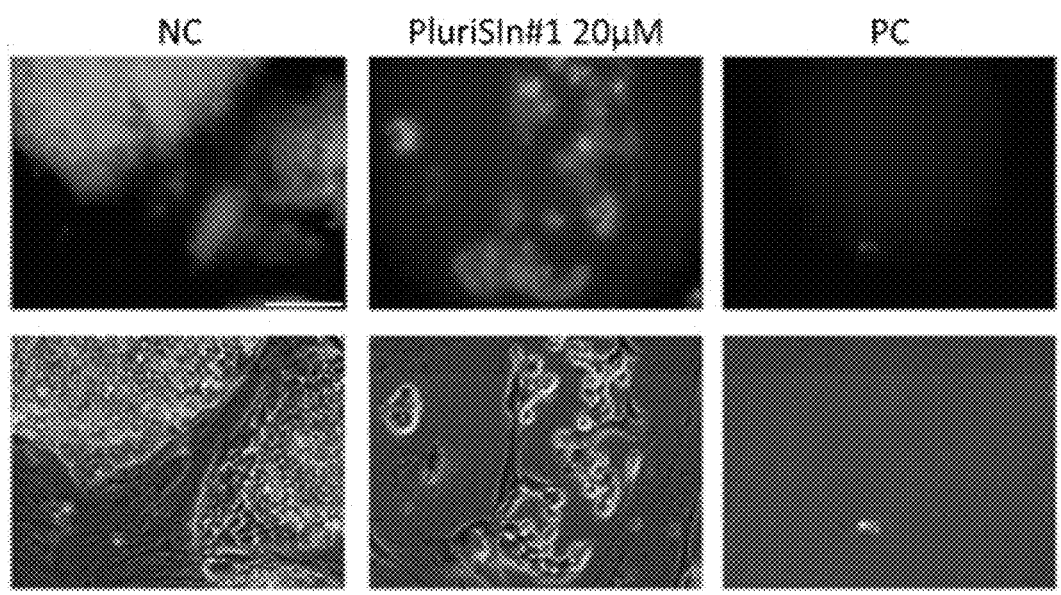
Figure 58:
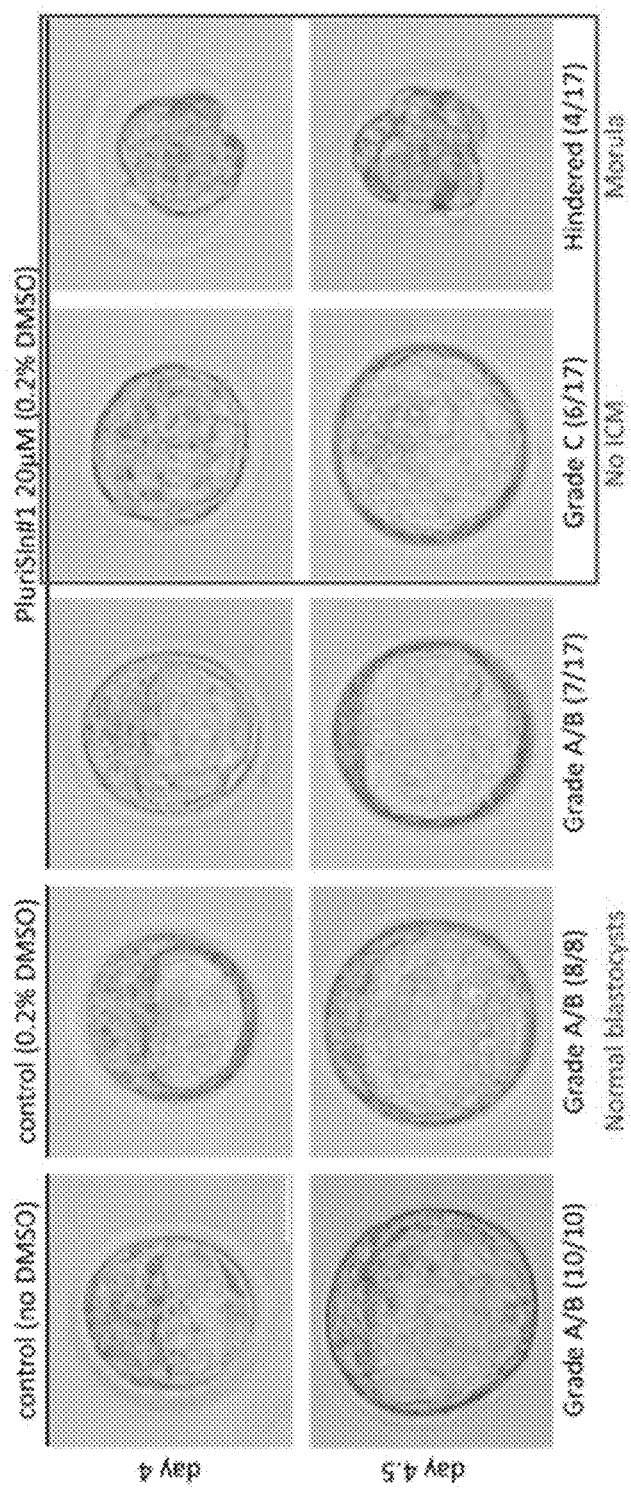
Figure 59:
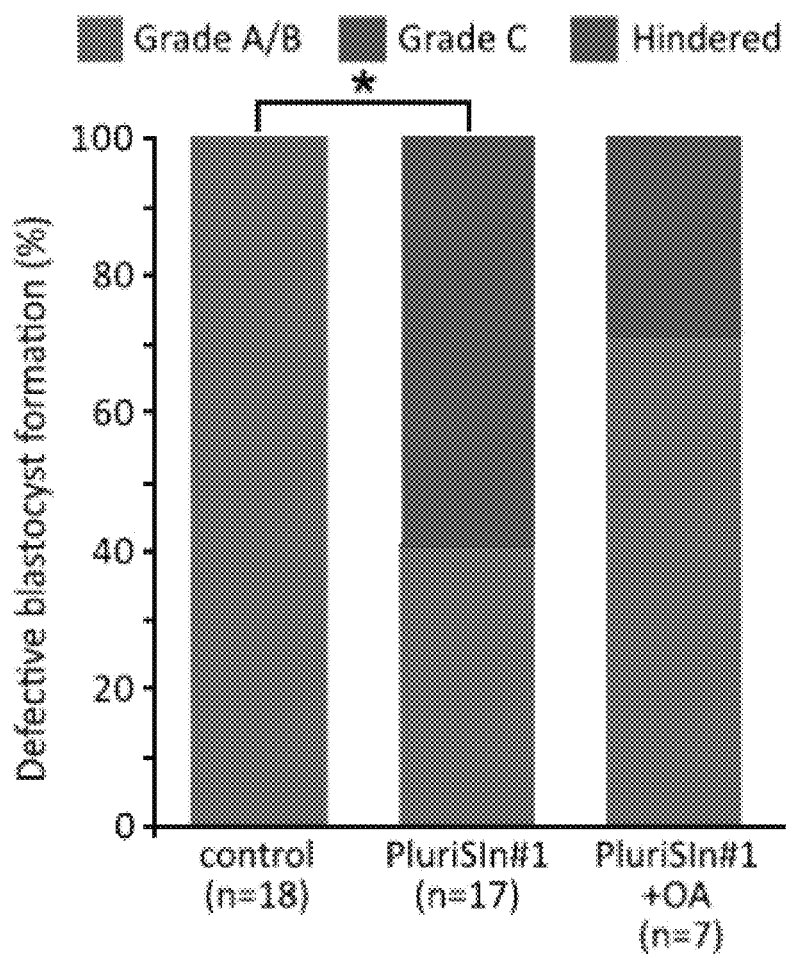
Figure 60:
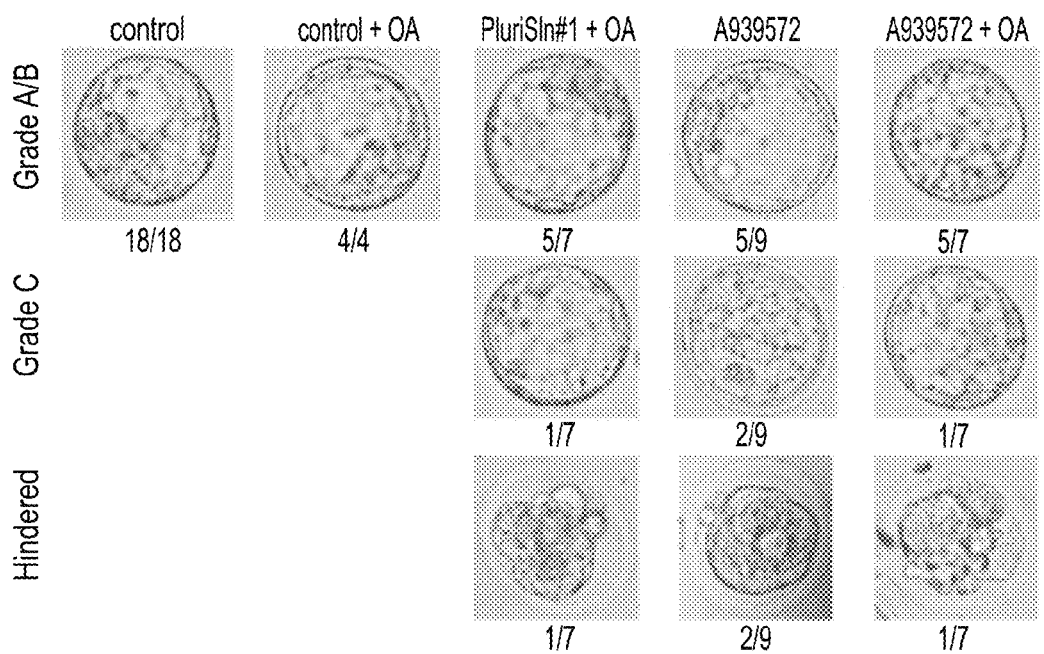
Figure 61:
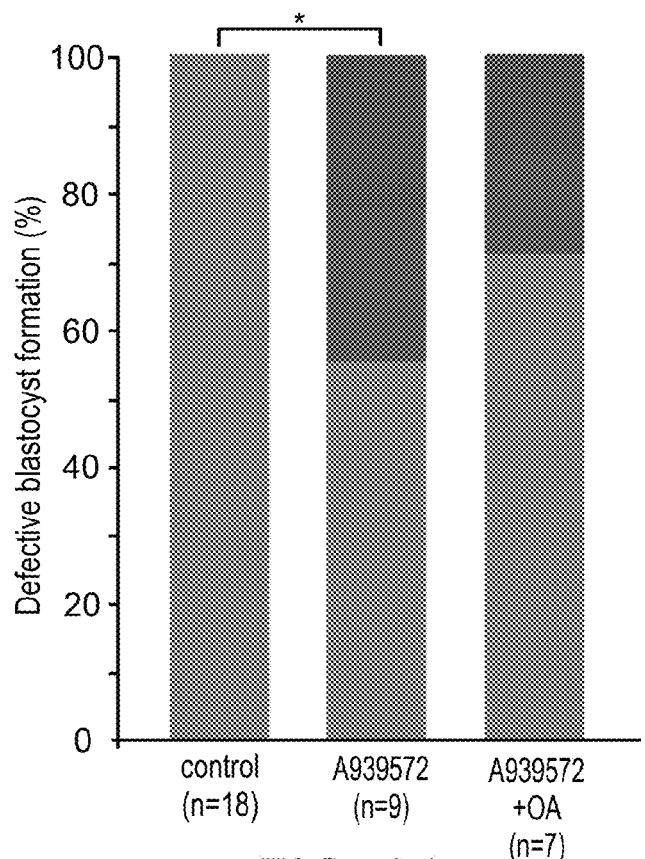
Figure 62:
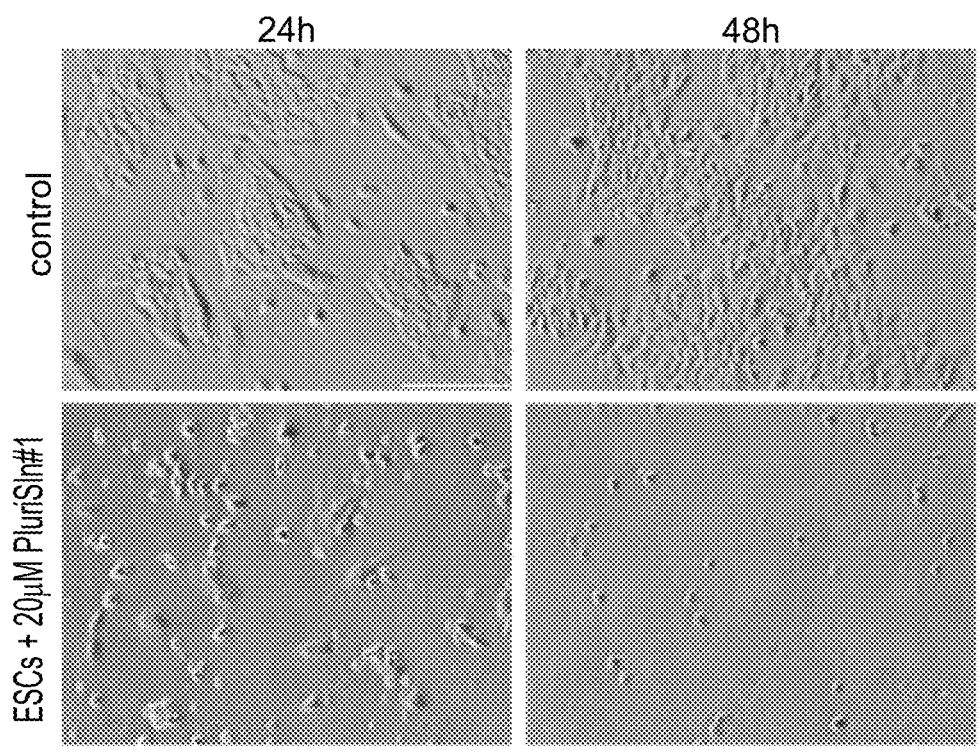
Figure 63A:
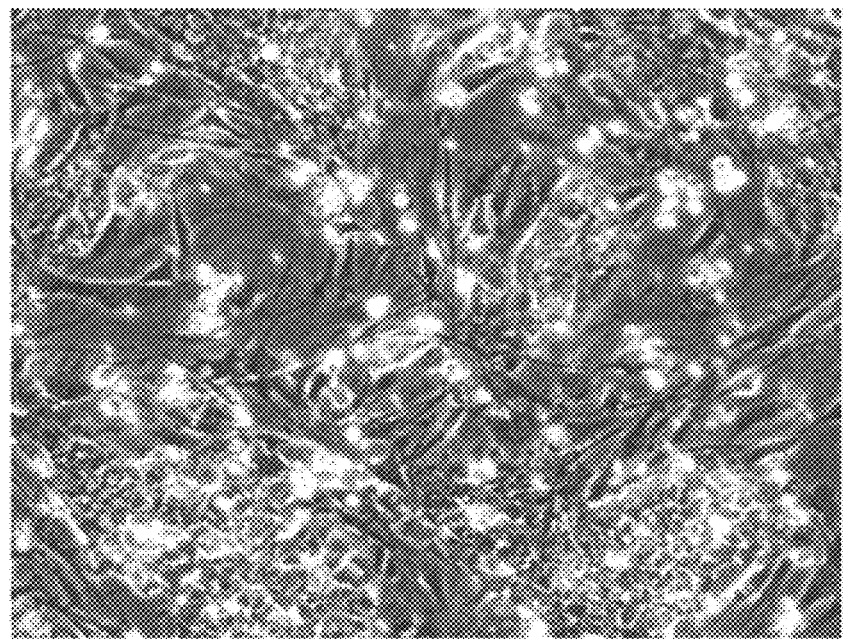
Figure 63B:
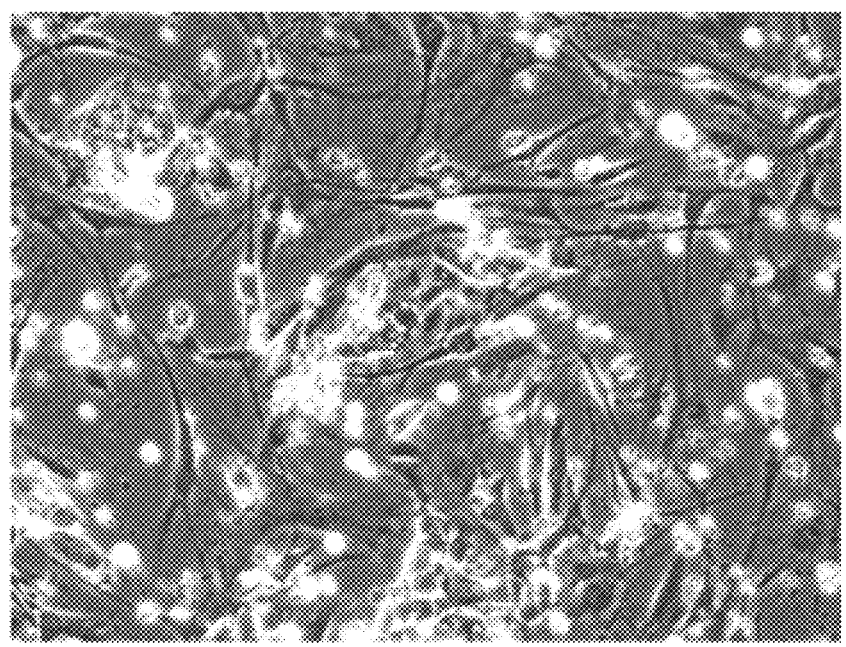
Figure 64:
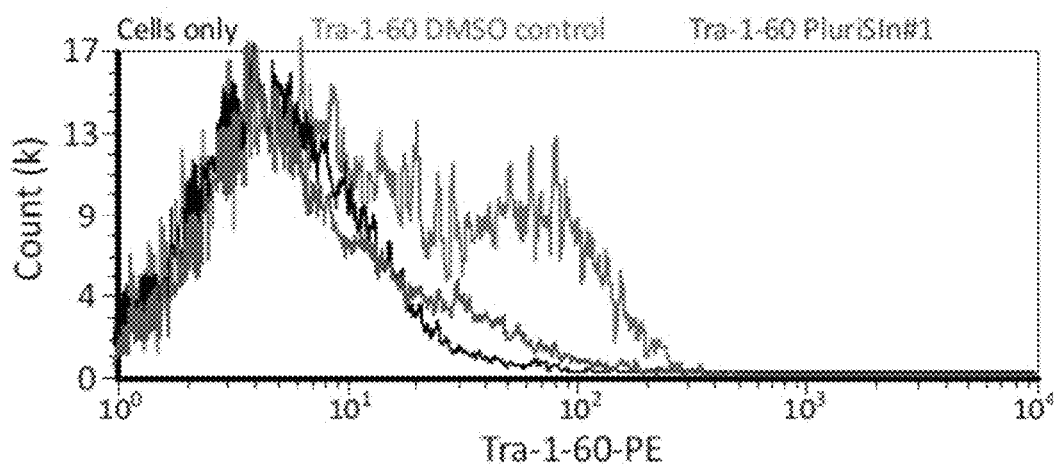
Figure 65:
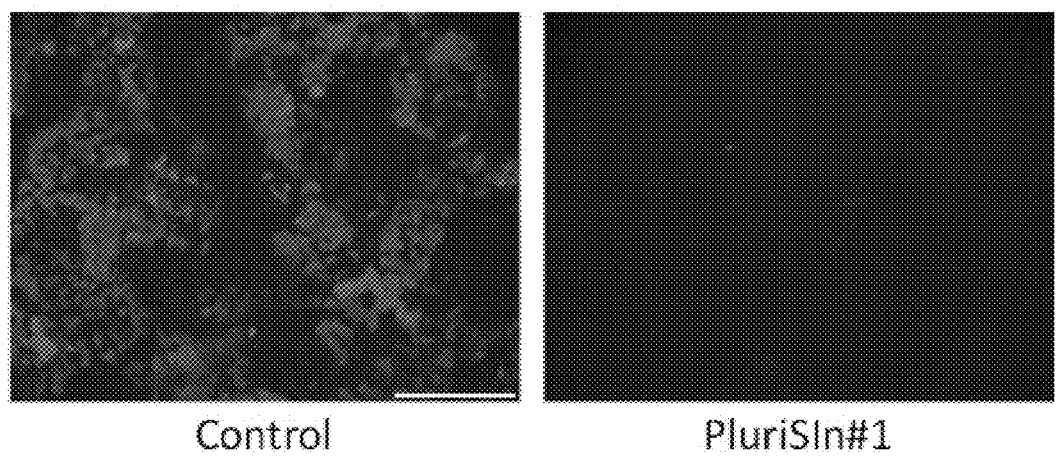
Figure 66A:
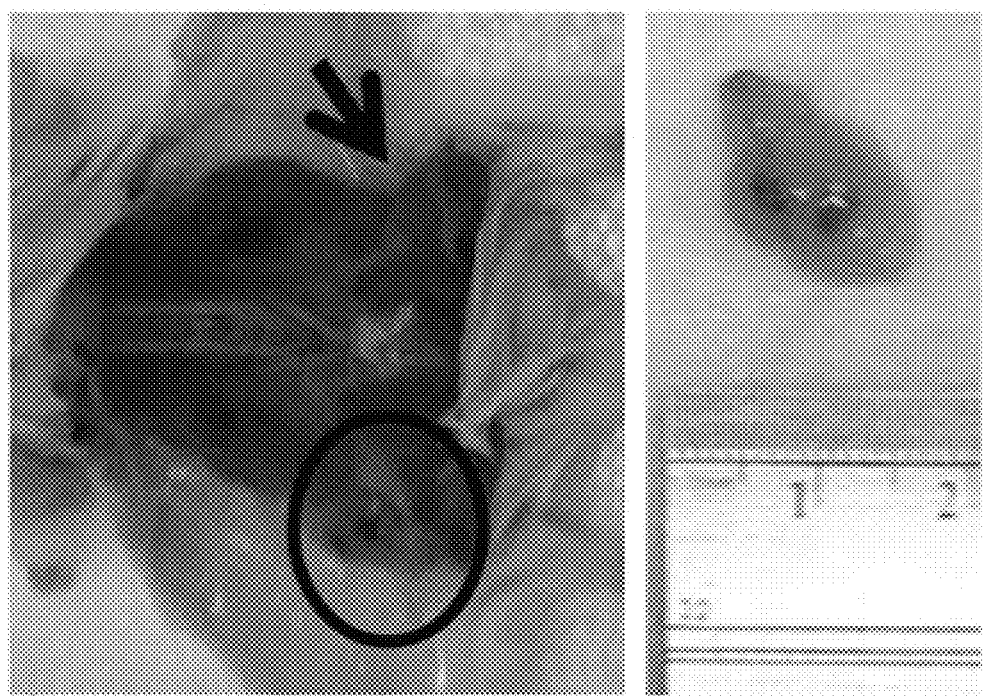
Figure 66B:
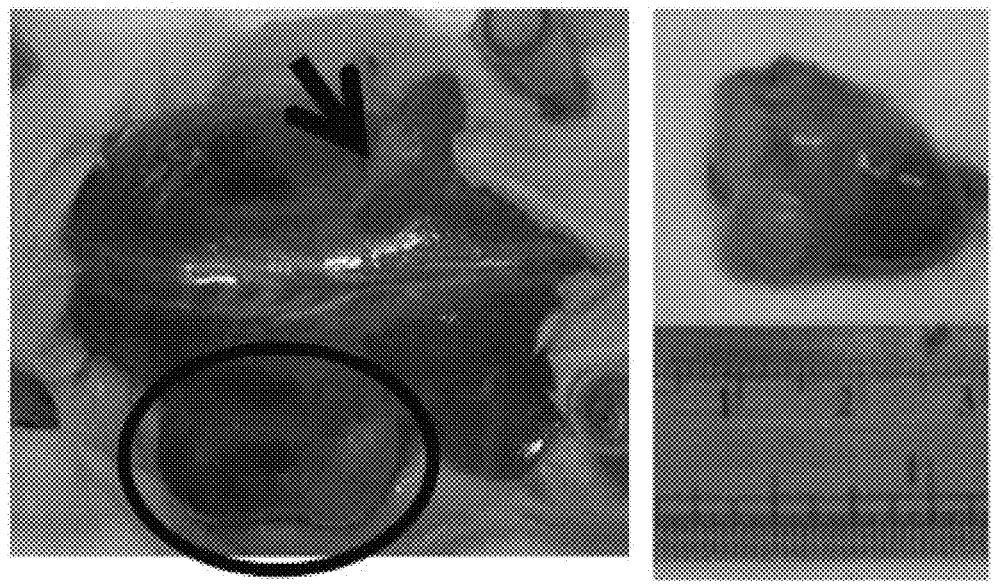
Figure 67A:
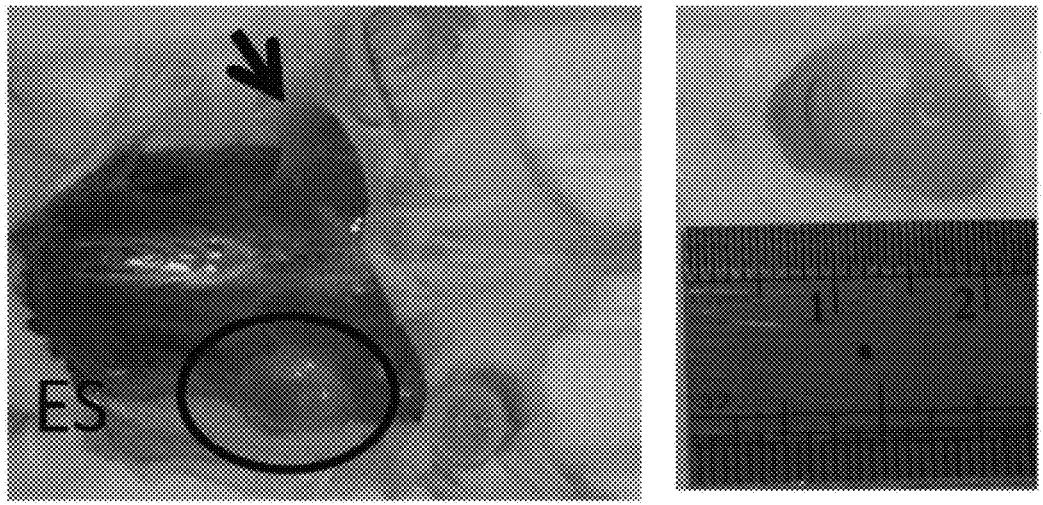
Figure 67B:
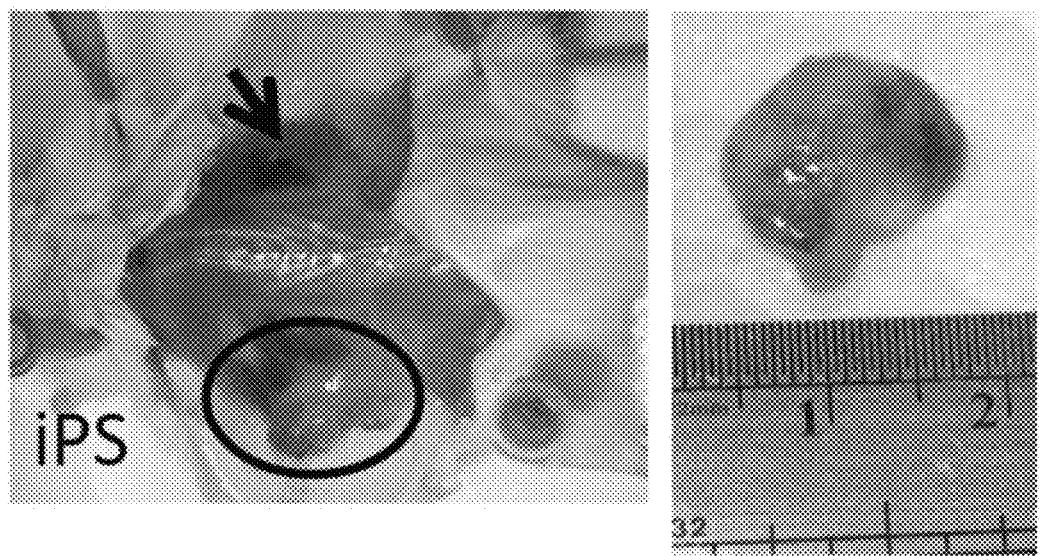
Figure 68:
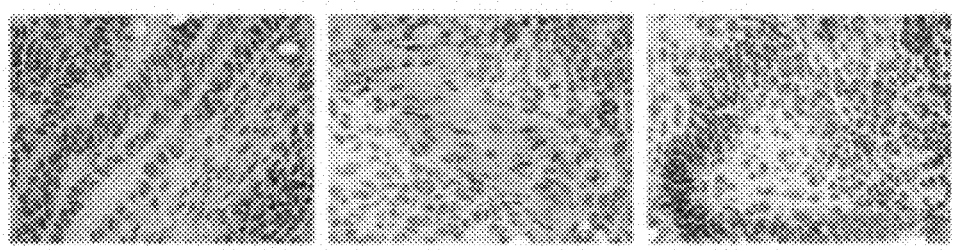
Figure 68:
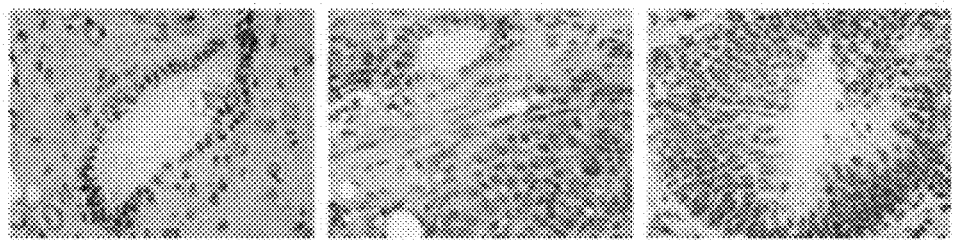
Figure 69:
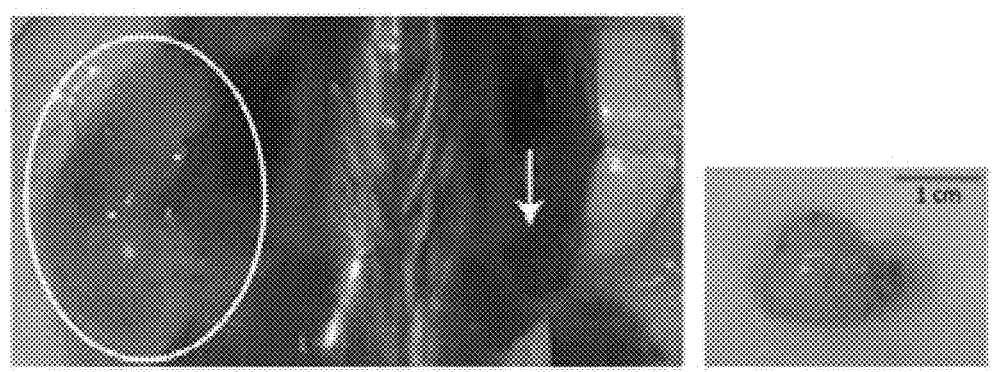
Figure 70:
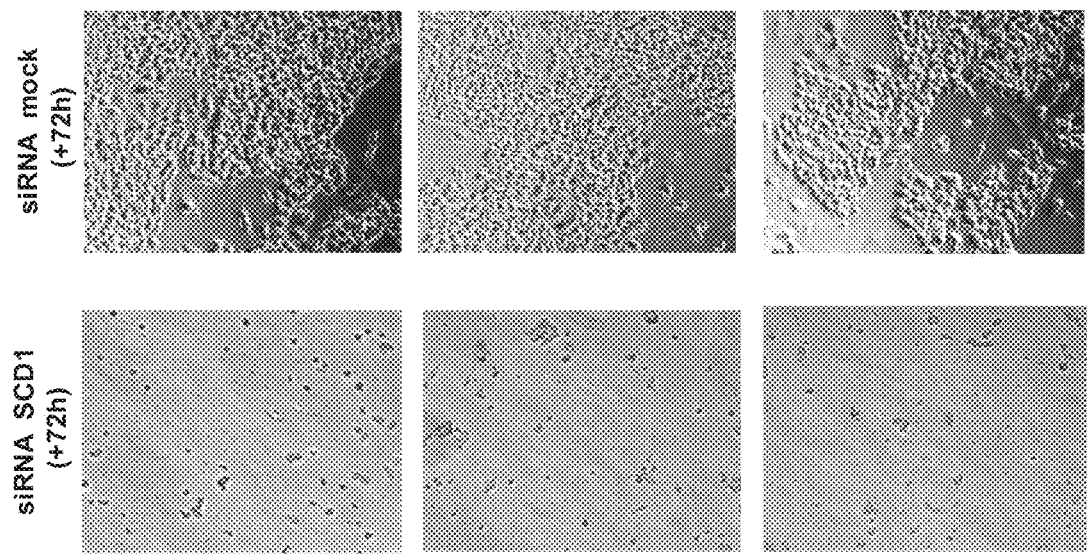
Figure 71:
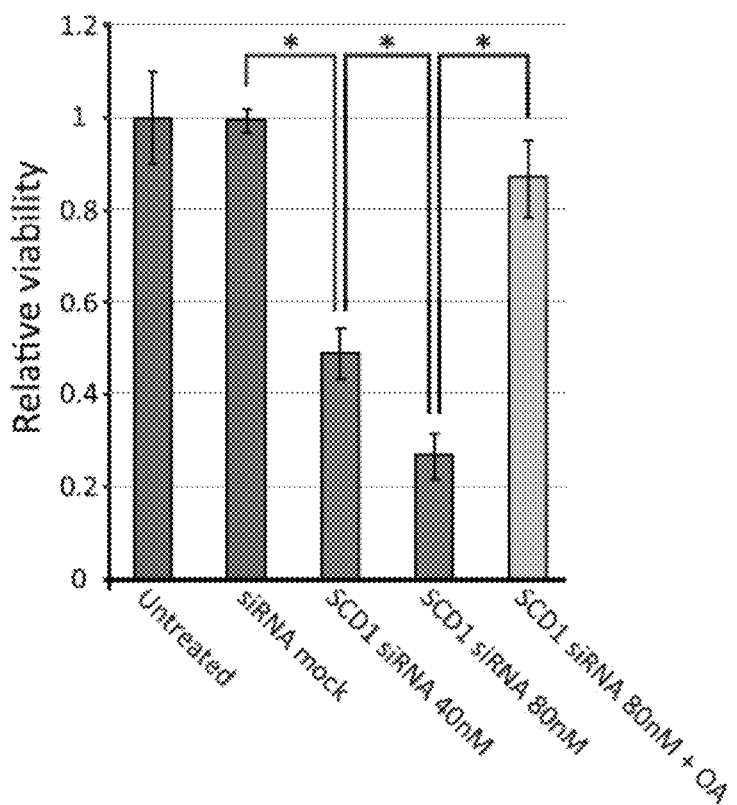
Figure 72:
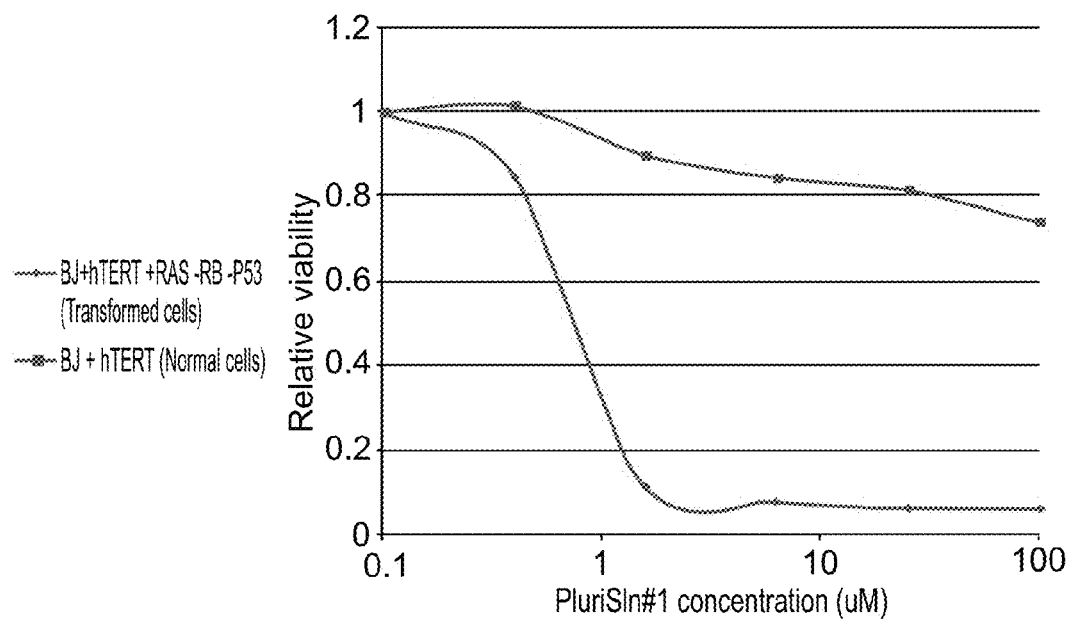
Figure 73:
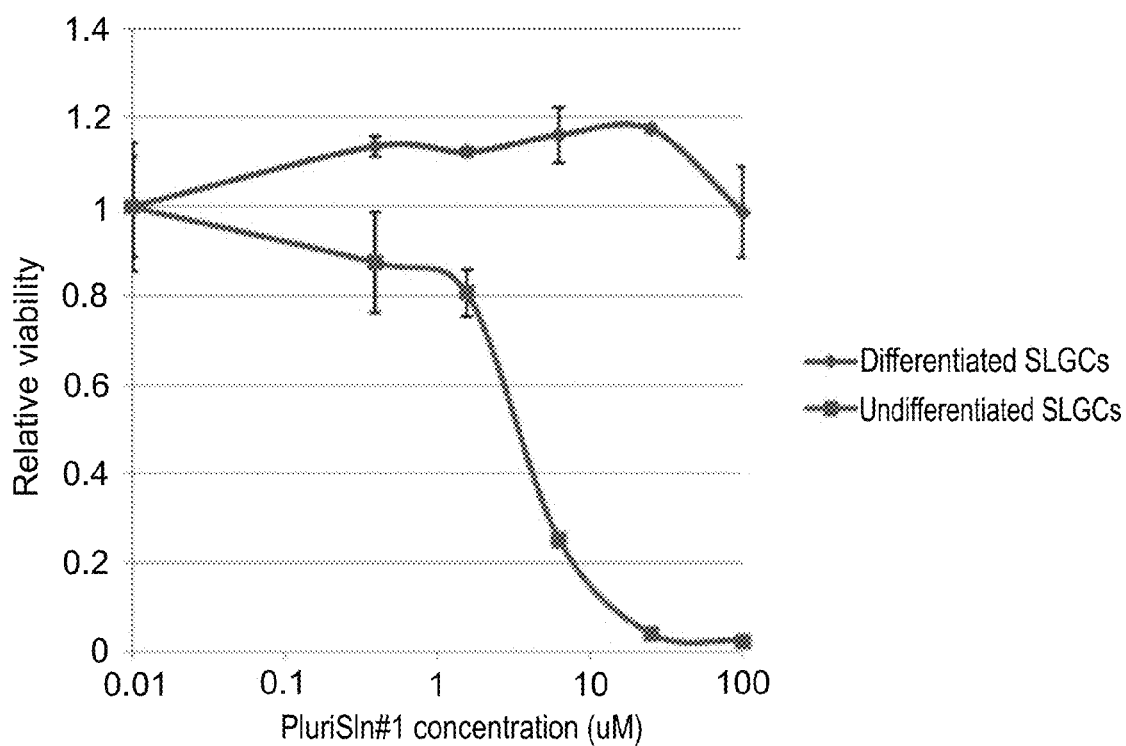

FIGS. 1A and 1B present microscopic images of genetically labeled CSES2-SO2/3 human embryonic stem cells, obtained by light microscopy (FIG. 1A), and by fluorescent microscopy showing fluorescence-labeled Oct-4 (FIG. 1B);

FIGS. 2A and 2B present images of H9 human embryonic stem cells stained for alkaline phosphatase, with (FIG. 2A) and without (FIG. 2B) magnification;

FIG. 3 presents fluorescent microscopy images of Mel-1 human embryonic stem cells stained for Oct-4, 24, 72 and 120 hours after being seeded in 384-well plates;

FIG. 4 presents fluorescent microscopy images of genetically labeled CSES2-SO2/human embryonic stem cells showing fluorescence-labeled Oct-4, 48 and 96 hours after being seeded in 384-well plates;

FIG. 5 is a graph showing relative light units (RLU) measured in an ATP-based luminescence assay of living H9 human embryonic stem cells, as a function of the number of H9 stem cells seeded in a sample (k=1,000; assay was performed 24 hours after seeding);

FIG. 6 presents an image of H9 cells stained with methylene blue in wells of a 384-well plate, 3, 24, 48 and 72 hours after being seeded;

FIG. 7 presents bar graphs showing exemplary results of a screen for cytotoxicity for timolol maleate (48), actidione (6), amsacrine hydrochloride (10), amodiaquine (9), carboplatin (13), ciprofloxacin (16), crotaline (19), doxycycline (22), estradiol (24), famotidine (25), fenofibrate (26), fludrocortisone acetate (27), imipramine (29), isoproterenol (31), ketoconazole (33), and tetracycline (46), following exposure to the compounds for 6, 24, 48 or 72 hours; 5 bars for each exposure time represent, from left-to-right, doses of 30 µM, 10 µM, 3 µM, 1 µM and 300 nm;

FIG. 8 is a scheme showing an exemplary protocol for screening cytotoxicity towards pluripotent cells;

FIG. 9 is a graph showing the Z' factor calculated for each of 149 384-well plates of an exemplary screen for cytotoxicity towards pluripotent cells (each color indicates a batch of plates which were screened together);

FIG. 10 is a histogram showing the number of tested compounds as a function of pluripotent cell inhibition exhibited by the compounds (cut-off value of 60% inhibition indicated by arrow);

FIG. 11 is a scatter plot showing inhibition of CSES2 and H9 human embryonic stem cells (ESCs) by 20 µM of exemplary compounds ($r^2$=0.87, data shown only for compounds inhibiting both cell types by over 60%);

FIGS. 12A-C are 2-dimensional (FIGS. 12A and 12B) and 3-dimensional (FIG. 12C) scatter plots showing $pEC_{50}$ values ($pEC_{50}$=-log $EC_{50}$, $EC_{50}$ values are in M units, FIGS. 12A and 12B) for exemplary compounds or percent inhibition by 20 µM of exemplary compounds (FIG. 12C), for CSES2 (FIGS. 12A-12C), CSES2-SO2/3 (FIGS. 12A and 12C) and H9 (FIG. 12C) human embryonic stem cells (ESCs) and BJ-iPS28 induced pluripotent stem cells (FIG. 12B);

FIG. 13 is a scatter plot showing $pEC_{50}$ values for exemplary compounds, as obtained for treatment of CSES2 cells for 24 hours (x-axis) and for 48 hours (y-axis) ($pEC_{50}$=-log $EC_{50}$, $EC_{50}$ values are in M units);

FIG. 14 is a scheme showing the relationship between exemplary pluripotent cells (embryonic stem (ES) cells and induced pluripotent stem (iPS) cells), and exemplary multipotent cells or progenitor cells, differentiated cells, and cancer cells;

FIG. 15 is a scatter plot showing inhibition of CSES2 cells (y-axis) and cardiomyocytes (x-axis) by 20 µM of exemplary compounds ($r^2$=0.03, data shown only for compounds inhibiting CSES2 cells by over 60%, selective inhibitors of CSES2 cells (less than 20% inhibition of cardiomyocytes) are indicated by rectangle);

FIG. 16 is a scatter plot showing inhibition of CSES2 cells and fibroblasts by 20 µM of exemplary compounds (data shown only for compounds inhibiting CSES2 cells by over 60%, selective inhibitors of CSES2 cells (less than 20% inhibition of fibroblasts) are indicated by rectangle);

FIG. 17 is a scatter plot showing inhibition of CSES2 cells and hepatocytes by 20 µM of exemplary compounds (data shown only for compounds inhibiting CSES2 cells by over 60%, selective inhibitors of CSES2 cells (less than 20% inhibition of hepatocytes) are indicated by rectangle);

FIG. 18 is a scatter plot showing inhibition of CSES2 cells and neuroblastoma (Kelly) cells by 20 µM of exemplary compounds (data shown only for compounds inhibiting CSES2 cells by over 60%, selective inhibitors of CSES2 cells (less than 20% inhibition of neuroblastoma cells) are indicated by rectangle);

FIG. 19 is a scatter plot showing inhibition of CSES2 cells and HeLa cells by 20 µM of exemplary compounds (data shown only for compounds inhibiting CSES2 cells by over 60%, selective inhibitors of CSES2 cells (less than 20% inhibition of HeLa cells) are indicated by rectangle);

FIG. 20 is a scatter plot showing inhibition of CSES2 cells and Huh7 cells by 20 µM of exemplary compounds (data shown only for compounds inhibiting CSES2 cells by over 60%, selective inhibitors of CSES2 cells (less than 20% inhibition of Huh7 cells) are indicated by rectangle);

FIG. 21 is a scatter plot showing inhibition of CSES2 cells and endodermal progenitor cells by 20 µM of exemplary compounds (data shown only for compounds inhibiting CSES2 cells by over 60%, selective inhibitors of CSES2 cells (less than 20% inhibition of endodermal progenitor cells) are indicated by rectangle);

FIG. 22 presents fluorescent microscopy images showing red fluorescence-labeling of Oct-4 (left) and green fluorescence labeling of SOX17 (right) in genetically labeled CSES2-SO2/3 cells before (day 0) and after (day 8) differentiation (scale bars=200 µm);

FIG. 23 presents histograms showing 98% of CSES2-SO2/3 cells exhibited fluorescent staining for CXCR4 after differentiation, whereas 3% exhibited fluorescent staining for CXCR4 before differentiation;

FIG. 24 presents fluorescent microscopy images showing red fluorescence labeling of Oct-4 (left, no fluorescence is visible, indicating lack of Oct-4) and green fluorescence labeling of SOX17 (right) in differentiated CSES2-SO2/3 cells after being plated in 384-well plates differentiation (scale bars=200 µm);

FIGS. 25A and 25B are scatter plots showing $pEC_{50}$ values for exemplary compounds, as obtained for treatment of BJ-fibroblasts (FIG. 25A, y-axis) and BJ-fibroblast-derived induced pluripotent stem cells (FIG. 25B, x-axis), as well as for CSES2-SO2/3 embryonic stem cells (FIG. 25B, x-axis) and CSES2-SO2/3-derived differentiated cells (FIG. 25B, y-axis) ($pEC_{50}=-\log EC_{50}$, $EC_{50}$ values are in M units);

FIGS. 26A and 26B present graphs showing the inhibition of CSES2 embryonic stem cells (FIG. 26A, left) and differentiated CSES2-derived endodermal progenitor cells (EPCs) (FIG. 26A, right), as well as the inhibition of BJ-fibroblasts (FIG. 26B, left) and BJ-fibroblast-derived BJ-iPS28 induced pluripotent stem cells (FIG. 26B, right), as a function of concentration of the exemplary compound PluriSIn #1 (concentration units shown on a logarithmic scale);

FIG. 27 presents graphs showing the inhibition (%) of CSES2-SO2/3 embryonic stem cells (SO2/3 ESCs), CSES2-SO2/3-derived differentiated cells (SO2/3 BJ-fibroblasts and BJ-iPS28 fibroblast-derived induced pluripotent stem cells as a function of concentration of the 15 exemplary compounds PluriSIns #1 to #15 (PluriSIn # is shown in upper left corner of each panel, concentration units shown on a logarithmic scale);

FIG. 28 presents a graph showing hierarchical clustering of cell types based on their inhibition by compounds (each compound is represented by a row), further showing the 15 compounds (marked by yellow rectangle) which inhibited only pluripotent stem cells (4 upper rows) (H=high inhibition, L=low inhibition);

FIG. 29 is a bar graph showing the number of viable H9 embryonic stem cells (relative to untreated control cells) 72 hours after treatment with 20 µM of each of PluriSIns #1 to #11, as determined by a methylene blue assay;

FIG. 30 presents microscopic images showing H9 embryonic stem cells 72 hours after treatment with 20 µM of each of PluriSIns #1 to #11, as well as untreated control cells;

FIG. 31 presents fluorescent microscopy images showing red fluorescence labeling of Oct-4 in CSES2-SO2/3 embryonic stem cells and green fluorescence labeling of SOX17 in CSES2-SO2/3-derived differentiated cells, following treatment with the exemplary compound PluriSIn #6, with 0.5% DMSO as a negative control (NC), or with 5 µM amsacrine hydrochloride as a cytotoxic positive control (PC) (scale bars=100 µm);

FIGS. 32A-32C present fluorescent microscopy images showing red fluorescence labeling of Oct-4 in CSES2-SO2/3 embryonic stem cells (FIG. 32A), green fluorescence labeling of SOX17 in CSES2-SO2/3-derived differentiated cells (FIG. 32B), and red fluorescence labeling of embryonic stem cells and blue fluorescence labeling of cell nuclei in a mixture of CSES2-SO2/3 embryonic stem cells and CSES2-SO2/3-derived differentiated cells (FIG. 32C), following treatment with the exemplary compound PluriSIn #1 (right panels) or with a DMSO control (left panels) (scale bars=100 µm);

FIG. 33 is a bar graph showing the number of viable BJ-fibroblasts, HeLa cells, HepG2 cells and Kelly cells (relative to untreated control cells) 72 hours after treatment with 20 µM PluriSIn #1, as determined by a methylene blue assay;

FIG. 34 presents microscopic images showing BJ-fibroblasts, HeLa cells, HepG2 cells and Kelly cells 72 hours after treatment with 20 µM PluriSIn #1, as well as untreated control cells;

FIG. 35 presents a graph showing gene expression-based hierarchical clustering of undifferentiated embryonic stem cells (ESCs) and ESC-derived differentiated endodermal progenitor cells, treated with PluriSIn #1, PluriSIn #6, or with no treatment (control); the map presents all differentially expressed genes (>2 fold) between control and treatment conditions (results of 2 experiments are presented for each of ESC controls and ESC with PluriSIn #1 treatment, red indicates high (H) expression, blue indicates low (L) expression);

FIG. 36 is a bar graph showing changes in expression of genes associated with apoptosis, following treatment of embryonic stem cells with PluriSIn #1 (ES PluriSIn#1) or PluriSIn #6 (ES PluriSIn#6), or treatment of ES-derived differentiated cells with PluriSIn #1 (Diff. PluriSIn #1);

FIGS. 37A and 37B present graphs showing a representative FACS analysis (FIG. 37A) of Annexin-V-fluorescein isothiocyanate (FITC) fluorescence and propidium iodide (PI) fluorescence, and a bar graph (FIG. 37B) showing embryonic stem cell apoptosis following treatment for 16 hours with 20 µM of the exemplary compound PluriSIn #1 (FIG. 37A, bottom, and FIG. 37B), or with control (0.2% DMSO; FIG. 37A, top, and FIG. 37B) (*p<0.05);

FIG. 38 presents images of immunoblots showing levels of procaspase-3 and cleaved caspase-3 in embryonic stem cells treated 20 µM of the exemplary compound PluriSIn #1 or with 1 mM dithiothreitol (DTT, a positive control), and in untreated control cells (β-catenin levels served as a loading control);

FIG. 39 is a bar graph showing viability of human embryonic stem cells treated for 24 hours with 20 µM of the exemplary compound PluriSIn #1, and of untreated control cells, in the presence of 0, 25 or 100 µM of Z-VAD-FMK (*p<0.05; **p<0.01);

FIG. 40 is a bar graph showing changes in expression of genes associated with endoplasmic reticulum (ER) stress and unfolded protein response (UPR), following treatment of embryonic stem cells with dithiothreitol (DTT, a general ER stress inducer) PluriSIn #1 (ES PluriSIn#1) or PluriSIn #6 (ES PluriSIn#6), or treatment of ES-derived differentiated cells with PluriSIn #1 (Diff. PluriSIn #1);

FIG. 41 is a bar graph showing expression (relative to control) of the spliced isoform sXBP1 (normalized to sRP2 levels) in embryonic stem cells (ESCs) and in cells derived from ESCs by 8-day differentiation (ESCs 8d diff.), following treatment for 12 hours with 20 µM of the exemplary compound PluriSIn #1, with 1 mM dithiothreitol (DTT) or with control (*p=0.007);

FIG. 42 presents images of an immunoblot showing phospho-eIF2α levels in embryonic stem cells and differentiated cells treated with 20 µM PluriSIn #1, with 1 mM dithiothreitol (DTT) or with control (α-tubulin served as a loading control);

FIG. 43 is a bar graph showing protein synthesis in embryonic stem cells (ES) and in fibroblasts, as determined by $^{35}$S-Met incorporation (normalized to total protein), following treatment for 12 hours with 20 µM PluriSIn #1, with 10 µM of cycloheximide or with control (*p=0.005);

FIG. 44 is a bar graph showing changes in expression of exemplary genes following treatment of embryonic stem cells (ESC) or ES-derived differentiated cells (Diff.) with the exemplary compounds PluriSIn #1 and PluriSIn #6, and treatment of H19299 cancer cells with the SCD inhibitor A939572;

FIG. 45 is a bar graph showing SCD1 activity (normalized to control levels) following treatment for 12 hours with 20 μM PluriSIn #1 or with control (*p=$2.1 \cdot 10^{-6}$);

FIG. 46 is a bar graph showing embryonic stem cell viability (normalized to control levels) following treatment for 48 hours with 75 nM of the SCD1 inhibitors A939572 and CAY-10566 in the presence or absence of 100 μM oleic acid (OA), or with control (*p≤0.0003);

FIG. 47 is a graph showing viability of pluripotent stem cells (relative to average control values), treated with 20 μM PluriSIn #1 or 2 μM amsacrine (ams) or untreated (control), as a function of concentration of oleic acid (OA) or oleic acid conjugated to bovine serum albumin (BSA);

FIG. 48 presents images showing pluripotent stem cells without treatment (Control) or following treatment with 20 μM PluriSIn #1 (3 right columns), with 0, 6.25, 25 and 100 μM oleic acid conjugated to bovine serum albumin;

FIG. 49 is a bar graph showing viability of embryonic stem cells following treatment with 20 μM of the exemplary compounds PluriSIn #1, #2, #3, #5 or #6, with and without 100 μM oleic acid conjugated to bovine serum albumin (OA) (*p≤0.006);

FIG. 50 presents graphs showing a representative FACS analysis of Annexin-V-fluorescein isothiocyanate (FITC) fluorescence and propidium iodide (PI) fluorescence following treatment for 18 hours with 20 μM of the exemplary compound PluriSIn #1, 100 nm of A939572, or with DMSO (control);

FIG. 51 is a bar graph showing expression (relative to control) of the spliced isoform sXBP1 in embryonic stem cells (ESCs) and in differentiated ESC-derived cells following treatment with 100 nm A939572 or with 1 mM dithiothreitol (DTT) (*p<0.05);

FIG. 52 presents images of an immunoblot showing phospho-eIF2α levels in embryonic stem cells (left) and in ESC-derived differentiated cells (right) treated with 20 μM PluriSIn #1, 100 nm A939572, 1 mM dithiothreitol (DTT) or with control (α-tubulin served as a loading control);

FIG. 53 is a bar graph showing protein synthesis in embryonic stem cells, as determined by $^{35}$S-Met incorporation (normalized to total protein), following treatment for 12 hours with 100 nm A939572, with 10 μM of cycloheximide or with control (*p<0.05);

FIG. 54 is a bar graph showing protein synthesis in H9 embryonic stem cells (ESCs) or BJ-fibroblasts (Differentiated), as determined by $^{35}$S-Met incorporation (normalized to total protein), following treatment for 48 hours with 1 mM dithiothreitol (DTT) or 10 μM of cycloheximide (Compound) with or without 100 μM oleic acid (OA), or with control;

FIG. 55 is a scheme showing a potential mechanism of exemplary compounds (e.g., PluriSIn #1), palmitic acid and oleic acid on cellular function and viability;

FIG. 56 presents a bar graph showing viability of mouse pluripotent stem cells following treatment with 20 μM of the exemplary compounds PluriSIn #1, #2, #4 or #6, relative to that of untreated (control) cells;

FIG. 57 presents present microscopic images of R1 Oct4-GFP mouse embryonic stem cells, obtained by light microscopy (lower panels) and by fluorescent microscopy showing fluorescence-labeled Oct-4 (upper panels), following treatment with the exemplary compound PluriSIn #6, with 0.5% DMSO as a negative control (NC), or with 5 μM amsacrine hydrochloride as a cytotoxic positive control (PC) (scale bar=100 μm);

FIG. 58 presents microscopic images of representative mouse embryos at 4 and 4.5 days post coitum, showing good quality (Grade A/B) blastocysts following treatment with control (0.2% DMSO or no DMSO) and in 7 of 17 samples following treatment with 20 μM PluriSIn #1, as well as bad quality (Grade C, no inner cell mass (ICM)) blastocysts in 6 of 17 samples, and hindered blastocysts (morulas) in 4 of 17 samples following treatment with 20 μM PluriSIn #1 (PluriSIn #1 administered with 0.2% DMSO, scale bar=100 μm);

FIG. 59 is a bar graph showing the proportion of good quality (Grade A/B) blastocysts, bad quality (Grade C) blastocysts and hindered blastocysts following treatment with control, or with 20 μM PluriSIn #1 in the presence or absence of 100 μM oleic acid (OA) (*p=0.0001);

FIG. 60 presents microscopic images of representative mouse embryos at 4.5 days post coitum, showing good quality (Grade A/B) blastocysts following treatment for 24 hours with control in the absence or presence of 100 μM oleic acid (OA), in 5 of 7 samples following treatment with 20 μM PluriSIn #1 or 100 nm A939572 with 100 μM oleic acid (OA), and in 5 of 9 samples following treatment with 100 nm A939572 alone, as well as bad quality (Grade C, no inner cell mass (ICM)) blastocysts and hindered blastocysts (morulas) in some samples following treatment with 20 μM PluriSIn #1 or 100 nm A939572 with 100 μM oleic acid (OA), or with 100 nm A939572 alone (scale bar=100 μm);

FIG. 61 is a bar graph showing the proportion of good quality (Grade A/B) blastocysts, bad quality (Grade C) blastocysts and hindered blastocysts following treatment for 24 hours with control, or with 100 nm A939572 in the presence or absence of 100 μM oleic acid (OA) (*p=0.007);

FIG. 62 presents microscopic images of H9 stem cells in a 6-well plate following exposure for 24 or 48 hours to 20 μM PluriSIn #1 or without PluriSIn #1 (control) (scale bar=200 μm);

FIGS. 63A and 63B present microscopic images of H9 stem cells on mouse embryonic fibroblasts in a 10-cm plate with embryonic stem cell medium, following exposure for 48 hours to 20 μM PluriSIn #1 (FIG. 63B) or no PluriSIn #1 (FIG. 63B of the sample shown in FIG. 63A);

FIG. 64 is a histogram showing the number of cells as a function of fluorescent staining for TRA-1-60, following a 48 hour treatment of a mixed cell population (differentiated and undifferentiated CSES2-SO2/3 cells) with PluriSIn #1 (Tra-1-60 PluriSIn#1) or with DMSO (Tra-1-60 DMSO control) (results for cells only, without staining, are also shown as a control);

FIG. 65 presents fluorescent microscopy images showing fluorescence labeling of Oct-4, following a 48 hour treatment of a mixed cell population (differentiated and undifferentiated CSES2-SO2/3 cells) with PluriSIn #1 or with control;

FIGS. 66A and 66B present images of mice injected on both sides with CSES2-SO2/3 embryonic stem cells (FIG. 66A) or BJ-iPS28 induced pluripotent stem cells (FIG. 66B), wherein injected cells on one side (injection locations marked by arrows) were pre-treated with PluriSIn #1 and no teratoma is visible, and injected cells on the other side were not pre-treated, and produced a teratoma (marked by ellipses, and shown in right panel);

FIGS. 67A and 67B present images of mice injected on both sides with a mixture of differentiated and undifferentiated H9 embryonic stem cells (FIG. 67A) or differentiated and undifferentiated BJ-iPS28 induced pluripotent stem cells (FIG. 67B), wherein injected cells on one side (injection locations marked by arrows) were pre-treated with PluriSIn #1 and no teratoma is visible, and injected cells on the other side were not pre-treated, and produced a teratoma (marked by ellipses, and shown in right panel);

FIG. 68 presents images showing histology of hematoxylin/eosin-stained ES-derived and iPS-derived teratomas;

FIG. 69 presents an image (left panel) of a mouse injected on both sides with human embryonic stem cells, wherein injected cells on one side (injection location marked by an arrow) were pre-treated with PluriSIn #1 and no teratoma is visible, and injected cells on the other side were not pre-treated, and produced a teratoma (marked by an ellipse, and shown in right panel);

FIG. 70 presents microscopic images of representative samples of human embryonic stem cells 72 hours after transfection with siRNA for SCD1 or with mock siRNA (siRNA for green fluorescent protein);

FIG. 71 is a bar graph showing relative viability of untreated human embryonic stem cells and human embryonic stem cells transfected with 40 nM or 80 nM siRNA for SCD1, 80 nM siRNA for SCD1 with 100 µM oleic acid (OA), or with control siRNA (siRNA for green fluorescent protein) 72 hours after transfection (*$p<0.05$);

FIG. 72 is a graph showing the relative cell viability of normal BJ fibroblasts immortalized by expression of human telomerase reverse transcriptase (BJ+hTERT) and BJ fibroblasts transformed by expression of hTERT and H-RasV12 and inhibition of p53 and retinoblastoma protein (BJ+ hTERT–RB–P53) as a function of concentration of the exemplary compound PluriSIn #1, following exposure to PluriSIn #1 for 72 hours (relative viability without PluriSIn #1 is defined as 1); and FIG. 73 is a graph showing the relative cell viability of differentiated and undifferentiated stem-like glioma cells (SLGCs) as a function of concentration of the exemplary compound PluriSIn #1, following exposure to PluriSIn #1 for 72 hours (relative viability without PluriSIn #1 is defined as 1).

DESCRIPTION OF SPECIFIC EMBODIMENTS OF THE INVENTION

The present invention, in some embodiments thereof, relates to therapy and, more particularly, but not exclusively, to treatment of undifferentiated cells such as pluripotent cells and undifferentiated cancer cells, to novel compounds suitable therefor, and to methods of identifying compounds suitable therefor.

As discussed hereinabove, previously suggested methods for removing potentially tumorigenic residual pluripotent stem cells (PSCs) from differentiated cultures are based on either genetic manipulations or on cell sorting. Such processes are generally not suitable for cell therapy purposes. Furthermore, to date, no single antibody and no single cycle of cell sorting which completely removes all undifferentiated cells from mixed cultures are known. There is therefore a need for a more robust method for the elimination of undifferentiated pluripotent stem cells from culture, particularly a method which is suitable for cell therapy purposes.

There is also a need for compounds capable of eliminating undifferentiated cells (e.g., undifferentiated cancer cells), particularly for use in treating proliferative diseases and disorders.

The present inventors have envisioned that improved removal of pluripotent stem cells (PSCs) may be obtained by identifying small molecules that selectively perturb crucial pathways in PSCs, and thus induce cell death in these cells only. While reducing the present invention to practice, the inventors designed an unbiased high-throughput screen of small molecules. Small molecules were selected which selectively target human PSCs, and efficiently and robustly eliminate all undifferentiated cells in culture, without affecting their differentiated derivatives. Application of these small molecules to cultures of differentiated cells prior to their transplantation into patients, according to some embodiments of the invention, would therefore considerably decrease, and even eliminate, the risk of tumor formation due to residual undifferentiated cells.

The strategy underlying some embodiments of the invention has several advantages over existing strategies, for example, being more rapid, efficient, robust and scalable than any other method previously suggested. In addition, the strategy described herein does not need genetic manipulation of the cells or dissociation into single cells. Thus, embodiments of the present invention allow genetically normal PSCs to be induced to differentiate into complex structures, which need not be disassembled prior to their transplantation.

While reducing the present invention to practice, the inventors further uncovered that compounds which selectively target undifferentiated cells without affecting their differentiated derivatives, are capable of efficiently and robustly eliminating undifferentiating cancer cells.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

According to an aspect of some embodiments of the present invention there is provided a use of any of the compounds as described herein as a cytotoxic inhibitor of undifferentiated cells (e.g., pluripotent stem cells, undifferentiated cancer cells).

According to an aspect of some embodiments of the present invention there is provided a use of any of the compounds as described herein in the manufacture of a medicament for inhibiting undifferentiated cells (e.g., pluripotent stem cells, undifferentiated cancer cells).

According to an aspect of some embodiments of the present invention there is provided a method of inhibiting pluripotent stem cells, which is effected by contacting undifferentiated cells (e.g., pluripotent stem cells, undifferentiated cancer cells) with any of the compounds as described herein.

In some embodiments, contacting the undifferentiated cells (e.g., pluripotent stem cells) with the compounds as described herein is effected in vitro.

In some embodiments, contacting is effected ex vivo. For example, in some embodiments, contacting is effected ex vivo in order to inhibit pluripotent stem cells in a sample (e.g., of cells other than pluripotent stem cells) to be administered to a subject.

In some embodiments, contacting is effected in vivo, by administering the compounds to a subject in need thereof.

Contacting cells with the inhibitor can be performed by any in vitro conditions including for example, adding the inhibitor to cells derived from a subject (e.g., a primary cell culture, a cell line) or to a biological sample comprising same (e.g., a fluid, liquid which comprises the cells) such that the inhibitor is in direct contact with the cells. According to some embodiments of the invention, the cells of the subject are incubated with the inhibitor. The conditions used for incubating the cells are selected for a time period/concentration of cells/concentration of inhibitor/ratio between cells and drug and the like which enable the inhibitor to induce cellular changes in undifferentiated cells (e.g., pluripotent stem cells), such as changes in transcription and/or translation rate of specific genes, proliferation rate, differentiation, cell death, necrosis, apoptosis and the like.

Methods of monitoring cellular changes induced by the inhibitor are known in the art and include for example, the MTT test which is based on the selective ability of living cells to reduce the yellow salt MTT (3-(4,5-dimethylthiazolyl-2)-2,5-diphenyltetrazolium bromide) (Sigma, Aldrich St Louis, Mo., USA) to a purple-blue insoluble formazan precipitate; the BrdU assay [Cell Proliferation ELISA BrdU colorimetric kit (Roche, Mannheim, Germany)]; the TUNEL assay [Roche, Mannheim, Germany]; the Annexin V assay [ApoAlert® Annexin V Apoptosis Kit (Clontech Laboratories, Inc., CA, USA)]; the Senescence associated-β-galactosidase assay [Dimri et al. *Proc Natl Acad Sci USA* 92:9363-9367 (1995)]; as well as various RNA and protein detection methods (which detect level of expression and/or activity) which are further described hereinabove.

According to an aspect of some embodiments of the present invention there is provided a compound as described herein for use as a cytotoxic inhibitor of undifferentiated cells (e.g., pluripotent stem cells, undifferentiated cancer cells) or in a method of inhibiting undifferentiated cells (e.g., pluripotent stem cells, undifferentiated cancer cells).

According to an aspect of some embodiments of the present invention there is provided a method of treating a proliferative disease or disorder associated with proliferation of undifferentiated cells in a subject in need thereof, the method comprising administering a therapeutically effective amount of any of the compounds as described herein.

According to an aspect of some embodiments of the present invention there is provided a use of any of the compounds as described herein in the manufacture of a medicament for treating a proliferative disease or disorder associated with proliferation of undifferentiated cells.

According to an aspect of some embodiments of the present invention there is provided a compound as described herein, for use in treating a proliferative disease or disorder associated with proliferation of undifferentiated cells.

As used herein, the phrase "undifferentiated cells" describes cells characterized by a lack of specific morphological and functional characteristics acquired by normal cells during development (a process known in the art as "differentiation"). Differentiation of cells during development results in different tissues and cell types (characterized by different sizes, shapes, membrane potentials, metabolic activities and/or responsiveness to signals) derived from a simple undifferentiated zygote. An undifferentiated cell may be a part of a lineage which has never undergone differentiation, or derived from a differentiated cell by a process which eliminates the specific morphological and functional characteristics of the differentiated cell.

In some embodiment of any of the aspects described herein, the undifferentiated cells comprise pluripotent stem cells.

In some embodiment of any of the aspects described herein, the undifferentiated cells comprise undifferentiated cancer cells. In some embodiments, the undifferentiated cancer cells comprise cancer stem cells and/or cancer stem-like cells.

As used herein, the phrase "pluripotent stem cells" describes stem cells (i.e., cells which can divide and differentiate into various cell types) which have a potential to differentiate into any of the three germ layers: endoderm, mesoderm or ectoderm. Examples known in the art include embryonic stem cells and induced pluripotent stem cells.

As used herein and in the art, the phrase "undifferentiated cancer cells" describes cancer cells characterized as being very immature and distinct from cells in the surrounding tissue, for example, anaplastic cells. The characterization of undifferentiated cancer cells is well known in the art, for example, undifferentiated cells may be categorized as Grade 4 using the guidelines of the American Joint Committee on Cancer [*AJCC Cancer Staging Manual*. 7th ed. New York, N.Y.: Springer; 2010].

The undifferentiated cancer cells may form a large proportion of cancer cells in a subject (e.g., in a tumor). Such cancers (e.g., Grade 4 tumors according to the guidelines of the American Joint Committee on Cancer [*AJCC Cancer Staging Manual*. 7th ed. New York, N.Y.: Springer; 2010]) are referred to herein and in the art as an "undifferentiated cancer".

Alternatively, undifferentiated cancer cells may form a small proportion of cancer cells in a subject (e.g., in a tumor). However, even in small amounts, undifferentiated cancer cells may have a very high clinical importance, for example, by acting as cancer stem cells.

As used herein and in the art, the phrases "cancer stem cell" and "cancer stem-like cell" are interchangeable and refer to a subset of cancer cells (e.g., cells found within tumors or hematological cancers) that possess the ability to give rise to various cell types found in a particular cancer sample. This ability to give rise to different cancer cell types (which results in a considerable tumor-forming ability) is similar to the properties of normal stem cells, which give rise to different normal cell types.

Multiple examples of cancer stem cells and markers which characterize them are known in the art. Suitable markers for identifying cancer stem cells are described, for example, by Medema [*Nature Cell Biology* 15:338-344 (2013)] and Visvader & Lindeman [*Nature Reviews Cancer* 8:755-768 (2008)]. Examples include, without limitation, leukemia cells which express the CD34 marker but not the CD38 marker, as described by Bonnet & Dick [*Nature Medicine* 3: 730-737 (1997]; brain cancer (e.g., glioma) cells which express the CD133 marker, as described by Singh et al. [*Cancer Research* 63:5821-5828 (2003)], and/or the CD15, CD90, $\alpha_6$-integrin and/or nestin markers; breast cancer cells which express CD44, but not CD2, CD3, CD10, CD16, CD18, CD31, CD64 and CD140b ("Lineage markers"), and low amounts or no CD24 (CD44$^+$CD24$^{-/low}$ Lineage$^-$ cells), as described in Al-Hajj et al. [*PNAS* 100: 3983-3988 (2003)], and/or ALDH1, CD24, CD90, CD133, Hedgehog-Gli activity and/or $\alpha_6$-integrin; colon cancer cells which express CD133, as described by O'Brien et al. [*Nature* 445:106-110], CD44 (e.g., EpCAM$^{hi}$/CD44$^+$ cells as described by Dalerba et al. [*PNAS* 104:10158-10163 (2007)], ABCB5, ALDH1, β-catenin activity, CD24, CD26, CD29, CD166 and/or LGR5; ovarian cancer cells which express CD44 and CD117, as described by Zhang et al. [*Cancer Research* 68:4311-4320 (2008)], CD24 and/or CD133; pancreatic cancer cells which express CD44, CD24 and epithelial-specific antigen (ESA), as described by Li et al. [*Cancer Research* 67:1030-1037 (2007)], ABCG2, ALDH1, CD133, c-Met, CXCR4, nestin and/or nodal activin; prostate cancer cells expressing CD133, $\alpha_2\beta_1$ integrin and CD144 ($\alpha_2\beta_1^{hi}$/CD133$^+$/CD144$^+$), as described by Maitland & Collins [*Journal of Clinical Oncology* 26:2862-2870 (2008)] and/or Lang et al. [*Journal of Pathology* 217:299-306 (2009)], ALDH1, CD44, CD166, α₆-integrin and/or Trop2; melanoma cells expressing ABCB5, as described by Schatton et al. [*Nature* 451:345-349 (2008)], and/or CD271, as described by Boiko et al. [*Nature* 466: 133-137 (2010)] and/or Civenni et al. [*Cancer Research* 71:3098-3109 (2011)], and/or high molecular weight-melanoma-associated antigen (HMW-MAA) and CD20, as described by Schmidt et al. [*PNAS* 108:2474-2479 (2011)] and/or ALDH1 and/or CD133; liver cancer cells which express CD13, CD24, CD44, CD90 and/or CD133; lung cancer cells which express ABCG2, ALDH1, CD90, CD117 and/or CD133; head and neck cancer cells which express CD44; mesenchymal cancer cells characterized by efflux of Hoechst 33342 dye; and multiple myeloma cells which do not express CD138 (CD138⁻), as described by Matsui et al. [*Blood* 103:2332-2336 (2004)], for example, CD138⁻/CD20⁺/CD27⁺ cells, such as described by Matsui et al. [*Cancer Research* 68: 190-197 (2008)].

It is expected that during the life of a patent maturing from this application many relevant cancer stem cells and cancer stem-like cells will be identified and characterized and the scope of the terms "cancer stem cell" and "cancer stem-like cell" is intended to include all such cells a priori.

As used herein, "a cytotoxic inhibitor of undifferentiated cells" describes a compound which, when contacting undifferentiated cells (e.g., pluripotent stem cells, undifferentiated cancer cells), reduces the population of these cells, by inhibiting the growth and/or proliferation of these cells and/or by killing at least a portion of these cells.

The phrase "inhibiting undifferentiated cells" thus describes reducing a population of undifferentiated cells (e.g., pluripotent stem cells, undifferentiated cancer cells), by inhibiting the growth and/or proliferation of these cells and/or by killing at least a portion of these cells.

As used herein, the phrase "therapeutically effective amount" describes an amount of the compound being administered which will relieve to some extent one or more of the symptoms of the condition being treated.

As used herein, the term "subject" includes mammals, preferably human beings at any age afflicted by a condition (e.g., proliferative disease or disorder) described herein, including individuals who are at risk to develop the condition.

In some embodiment, the subject is an individual diagnosed as having undifferentiated cancer cells, which may be present in a degree such that the subject is diagnosed with a condition associated with the undifferentiated cells (e.g., a proliferative disease or disorder), as described herein, or the subject is at risk of developing such a condition.

As discussed herein, inhibiting pluripotent stem cells (PSCs) may prevent these cells from maturing into cancerous cells, and thus is advantageous in cases of subject undergoing stem cell therapy (or other cell therapy), in order reduce a risk of cancer in such subjects.

Accordingly, in some embodiments, any of the methods and uses described herein is utilized for reducing a risk of cancer in a subject treated by a stem cell therapy.

Subjects undergoing stem cell therapy can be, for example, subjects who suffered, prior to undergoing stem cell therapy, from diseases or disorders which are treatable by stem cell therapy. Such diseases and disorders include, but are not limited to, cancer, Type I diabetes mellitus, Parkinson's disease, Huntington's disease, Alzheimer's disease, brain damage, spinal cord injury, celiac disease, cardiac failure, heart damage, anemia, baldness, deafness, blindness, vision impairment, amyotrophic lateral sclerosis, graft vs. host disease, Crohn's disease, infertility, wounds, orthopedic diseases or disorders, muscle damage and neurological disorders.

Inhibiting PSCs is also advantageous in cases where due to proliferation of PSCs, a subject is at risk of developing, or has already developed, a proliferative disease or disorder associated with proliferation of the stem cells.

As used herein, a "proliferative disease or disorder" describes any medical condition that is associated with abnormal proliferation of undifferentiated cells (e.g., stem cells, undifferentiated cancer cells). Such conditions include, but are not limited to, benign and malignant neoplasia (e.g., cancer), carcinoma in situ and hyperplasia.

Examples of proliferative diseases or disorders associated with proliferation of undifferentiated cells include, without limitation, teratomas, undifferentiated cancers, leukemias, brain cancers (e.g., gliomas), breast cancers, colon cancers, ovarian cancers, pancreatic cancers, prostate cancers, melanomas, liver cancers, lung cancers, head and neck cancers, mesenchymal cancers and multiple myelomas.

In some embodiments, the proliferative disease or disorder is a teratoma and/or an undifferentiated cancer.

In some embodiments, the proliferative disease or disorder is a cancer such as leukemia, brain cancer (e.g., glioma), breast cancer, colon cancer, ovarian cancer, pancreatic cancer, prostate cancer, melanoma, liver cancer, lung cancer, head and neck cancer, mesenchymal cancer and/or multiple myeloma, the cancer being associated with proliferation of cancer stem cells.

Subjects at risk of developing such proliferative diseases or disorders are, for example, subjects who were administered (e.g., as part of a cell therapy) stem cells or cells derived (e.g., by differentiation) from stem cells, wherein such cells are pluripotent stem cells, are known to comprise pluripotent stem cells, or carry a risk of including one or more pluripotent stem cells.

Subjects suffering from diseases or disorders associated with proliferation of stem cells are, for example, subjects who have a benign or malignant germ cell tumor (e.g., nonseminatous germ cell tumor), for example, a teratoma.

According to some embodiments of the present invention, compounds usable in any of the methods and uses described herein are represented by Formula I:

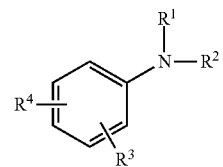

Formula I wherein:
R¹ is hydrogen, and R² is selected from the group consisting of:
  hydrogen,
  2,4-dioxo-5-fluoropyrimidin-1-ylcarbonyl,
  2-methylbenzofuran-3-ylmethyleneamino, and
  —NH—R⁵, wherein R⁵ is selected from the group consisting of:
    pyridinylcarbonyl (e.g., pyridin-4-ylcarbonyl),
    2-hydroxyl-2-phenyl-2-thiophen-2-yl-acetyl,
    (C₁₋₆)alkyl-carbonyl (e.g., a linear alkyl-carbonyl, a non-substituted alkyl carbonyl), N-(ethoxycarbonylmethyl)-2,4-dioxo-pyrrolidine-3-ylidene-methyl,
naphthylsulfonyl (e.g., 2-naphthylsulfonyl), and
N-hydroxy-acetimidoyl (—C(=NOH)CH$_3$);
or wherein:
$R^1$ is benzoyl and $R^2$ is 4-chlorobenzamido.
$R^3$ and $R^4$ are independently selected from the group consisting of hydrogen, halo, NH$_2$, biphenyloxymethyl (e.g., ([1,1'-biphenyl]-4-yloxy)methyl) and (C$_{1-4}$)alkyl (e.g., a linear alkyl, a non-substituted alkyl). In some embodiments, the halo is chloro. In some embodiments, the alkyl is methyl.

In some embodiments, at least one of $R^1$, $R^2$, $R^3$ and $R^4$ is not hydrogen, halo, NH$_2$ or (C$_{1-4}$)alkyl.

In some embodiments, $R^1$ is hydrogen, and $R^2$ is as defined hereinabove.

In some embodiments, $R^1$ is hydrogen, and $R^2$ is selected from the group consisting of:
2,4-dioxo-5-fluoropyrimidin-1-ylcarbonyl,
2-methylbenzofuran-3-ylmethyleneamino, and
—NH—$R^5$, wherein $R^5$ is selected from the group consisting of:
pyridinylcarbonyl,
2-hydroxyl-2-phenyl-2-thiophen-2-yl-acetyl,
(C$_{1-6}$)alkyl-carbonyl,
N-(ethoxycarbonylmethyl)-2,4-dioxo-pyrrolidine-3-ylidene-methyl, naphthylsulfonyl, and
N-hydroxy-acetimidoyl; and
$R^3$ and $R^4$ are independently selected from the group consisting of hydrogen, chloro, NH$_2$, and methyl.

In some embodiments, $R^1$ is benzoyl and $R^2$ is 4-chlorobenzamido; and
$R^3$ and $R^4$ are independently selected from the group consisting of hydrogen, chloro, NH$_2$, and methyl.

In some embodiments, $R^2$ is selected from the group consisting of 2-methylbenzofuran-3-ylmethyleneamino, —NH—$R^5$ (as defined herein), and 4-chlorobenzamido. In some embodiments, $R^2$ is selected from the group consisting of —NH—$R^5$ (as defined herein), and 4-chlorobenzamido. In some embodiments, $R^2$ is selected from the group consisting of 2-methylbenzofuran-3-ylmethyleneamino and —NH—$R^5$ (as defined herein). In some embodiments, $R^2$ is —NH—$R^5$.

An exemplary compound that is usable in any of the methods and uses as described herein is a compound of formula II:

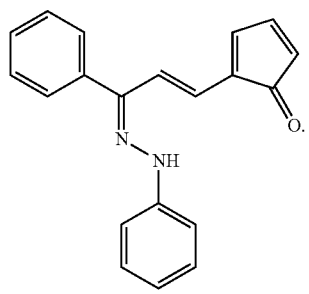

Formula II

Another exemplary compound that is usable in any of the methods and uses as described herein is a compound of formula III:

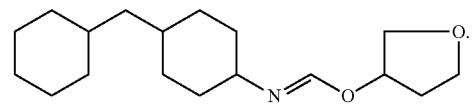

Formula III

Another exemplary compound that is usable in any of the methods and uses as described herein is a compound of formula IV:

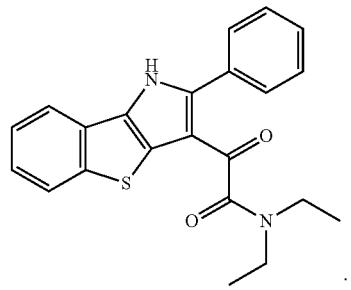

Formula IV

Another exemplary compound that is usable in any of the methods and uses as described herein is a compound of formula V:

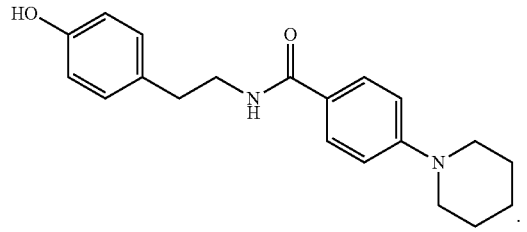

Formula V

Another exemplary compound that is usable in any of the methods and uses as described herein is a compound of formula VI:

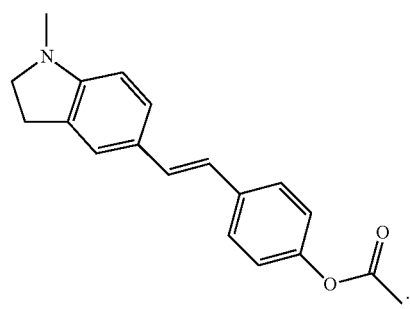

Formula VI

The term "alkyl" describes an aliphatic hydrocarbon including straight chain and branched chain groups. Herein, the number of carbon atoms in an alkyl group is indicated. The alkyl group may be substituted or unsubstituted. In some embodiments, the alkyl is non-substituted, unless explicitly stated otherwise. Substituted alkyl may have one or more substituents, whereby each substituent group can independently be, for example, amine, halo, sulfonate, sulfoxide, phosphonate, hydroxy, alkoxy, thiohydroxy, thioalkoxy, cyano, isocyanate, nitro, azo, sulfonamide, oxo, carbonyl, carboxy, thiocarbamate, urea, thiourea, carbamate, epoxide, thiirane, aziridine, amide and hydrazine.

As used herein, the term "amine" describes both a —NRxRy group and a —NRx- group, wherein Rx and Ry are each independently hydrogen, methyl ($CH_3$) or ethyl ($CH_2CH_3$).

The amine group can therefore be a primary amine, where both Rx and Ry are hydrogen, a secondary amine, where Rx is hydrogen and Ry is alkyl, or a tertiary amine, where each of Rx and Ry is alkyl.

The terms "halide" and "halo" describes fluorine, chlorine, bromine or iodine.

The term "sulfoxide" describes a —S(=O)Rx group, where Rx is as defined hereinabove.

The term "sulfonate" describes a —S(=O)$_2$—Rx group, where Rx is as defined herein.

The term "sulfonamide", as used herein, encompasses both S-sulfonamides and N-sulfonamides.

The term "S-sulfonamide" describes a —S(=O)$_2$—NRxR$_Y$ group, with Rx and R$_Y$ as defined herein.

The term "N-sulfonamide" describes an RxS(=O)$_2$—NR$_Y$— group, where Rx and R$_Y$ are as defined herein.

The term "carbonyl" or "carbonate" as used herein, describes a —C(=O)—Rx group, with Rx as defined herein.

The term "oxo", as used herein, describes an =O group.

The terms "hydroxy" and "hydroxyl" describe a —OH group.

The term "alkoxy" describes both an —O—($C_{1-2}$)alkyl group.

The term "thiohydroxy" describes a —SH group.

The term "thioalkoxy" describes both a —S—($C_{1-2}$)alkyl group.

The terms "cyano" and "nitrile" describe a —C≡N group.

The term "isocyanate" describes an —N=C=O group.

The term "nitro" describes an —NO$_2$ group.

The term "azo" describes an —N=NRx group, with Rx as defined hereinabove.

The term "carboxy", as used herein, encompasses both C-carboxy and O-carboxy groups.

The term "C-carboxy" describes a —C(=O)—ORx group, where Rx is as defined herein.

The term "O-carboxy" describes a —OC(=O)—Rx group, where Rx is as defined herein.

The term "urea" describes a —NRxC(=O)—NRyRw group, where Rx and Ry are as defined herein and Rw is as defined herein for R$_X$ and Ry.

The term "thiourea" describes a —NRx-C(=S)—NRyRw group, with Rx, Ry and Ry as defined herein.

The term "amide", as used herein, encompasses both C-amides and N-amides.

The term "C-amide" describes a —C(=O)—NRxRy group, where Rx and Ry are as defined herein.

The term "N-amide" describes an RxC(=O)—NRy- group, where Rx and Ry are as defined herein.

The term "carbamate", as used herein, encompasses both N-carbamates and O-carbamates.

The term "N-carbamate" describes a RyOC(=O)—NRx- group, with Rx and Ry as defined herein.

The term "O-carbamate" describes an —OC(=O)—NRxRy group, with Rx and Ry as defined herein.

The term "thiocarbamate", as used herein, encompasses both O-thiocarbamates and N-thiocarbamates.

The term "O-thiocarbamate" describes a —OC(=S)—NRxRy group, with Rx and Ry as defined herein.

The term "N-thiocarbamate" describes a RyOC(=S)NRx- group, with Rx and Ry as defined herein.

As used herein, the term "epoxide" describes a

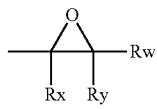

group, where Rx, Ry and Rw are as defined herein.

As used herein, the term "thiirane" describes a group that is equivalent to an epoxide, wherein the oxygen atom of the epoxide is replaced with a sulfur atom.

As used herein, the term "aziridine" describes a group that is equivalent to an epoxide, wherein the oxygen atom of the epoxide is replaced with a nitrogen atom, and the nitrogen atom binds, in addition to two adjacent carbon atoms, Rq, wherein Rq is defined according to the same definition as Rx.

The term "hydrazine", as used herein, describes a —NRx-NRyRw group, with Rx, Ry, and Rw as defined herein.

In any of the methods and uses described herein, the compounds as described herein as cytotoxic inhibitors of undifferentiated cells (e.g., PSCs, undifferentiated cancer cells) can be utilized either per se or, preferably within a pharmaceutical composition which further comprises a pharmaceutically acceptable carrier.

Thus, according to additional aspects of the present invention, there is provided pharmaceutical composition, which comprises one or more compounds described herein (e.g., cytotoxic inhibitors) and a pharmaceutically acceptable carrier.

As used herein a "pharmaceutical composition" refers to a preparation of the compounds presented herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with embodiments of the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophthalmically, vaginally, rectally, intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

Compositions of embodiments of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of a condition described herein (e.g., a proliferative disease or disorder associated with proliferation of undifferentiated cells), as is detailed herein.

Thus, according to an embodiment of the present invention, the pharmaceutical composition of the present invention is being packaged in a packaging material and identified in print, in or on the packaging material, for use in the treatment of a condition described herein (e.g., a proliferative disease or disorder associated with proliferation of undifferentiated cells).

According to further embodiments of the any of the methods, uses and compositions presented herein, the compounds of the present invention can be combined with other active ingredients which are commonly used to treat a condition described herein (e.g., a proliferative disease or disorder associated with proliferation of undifferentiated cells).

According to another aspect of embodiments of the invention, there is provided a compound described herein being identified for use in inhibiting undifferentiated cells (e.g., pluripotent stem cells and/or undifferentiated cancer cells, as described herein).

As shown in the Examples herein, the present inventors have demonstrated that inhibition of SCD (stearoyl-CoA desaturase) results in a selective cytotoxic inhibition of pluripotent stem cells.

Thus, according to an aspect of some embodiments of the present invention there is provided a use of an SCD inhibitor as a cytotoxic inhibitor of undifferentiated cells. In exemplary embodiments, the undifferentiated cells are pluripotent stem cells.

According to an aspect of some embodiments of the present invention there is provided a use of an SCD inhibitor in the manufacture of a medicament for inhibiting undifferentiated cells. In exemplary embodiments, the undifferentiated cells are pluripotent stem cells.

According to an aspect of some embodiments of the present invention there is provided a method of inhibiting undifferentiated cells, which is effected by contacting undifferentiated cells with an SCD inhibitor. In exemplary embodiments, the undifferentiated cells are pluripotent stem cells.

According to an aspect of some embodiments of the present invention there is provided a pharmaceutical composition comprising a therapeutically effective amount of an SCD inhibitor and a pharmaceutically acceptable carrier. In some embodiments, such a composition is formulated, identified for use, and/or packaged as described herein (e.g., as described herein with respect to the compounds described herein).

In some embodiments, the SCD inhibitor (as described in any of the aspects of the invention) is an SCD1 inhibitor.

Exemplary SCD1 inhibitors include A939572 (4-(2-chlorophenoxy)-N-(3-(methylcarbamoyl)-phenyl)piperidine-1-carboxamide), CAY-10566 (3-[4-(2-chloro-5-fluorophenoxy)-1-piperidinyl]-6-(5-methyl-1,3,4-oxadiazol-2-yl)-pyridazine), MF-438 (2-methyl-5-[6-[4-[2-(trifluoromethyl)phenoxy]piperidin-1-yl]pyridazin-3-yl]-1,3,4-thiadiazole), CVT-11127 (N-(2-(6-(3,4-dichlorobenzylamino)-2-(4-methoxyphenyl)-3-oxopyrido[2,3-b]pyrazin-4(3H)-yl) ethyl)acetamide), TOFA (5-(tetradecyloxy)-2-furoic acid) and GSK-993 (N-(1-(5-chloro-2-isobutoxybenzyl)-5-methyl-1H-pyrazol-3-yl)-1,2,3,4-tetrahydroisoquinoline-6-carboxamide, e.g., as described by Issandou et al. [*Eur J Pharmacol.* 618:28-36 (2009)] and Mason et al. [*PloS One* 7:e33823 (2012)]).

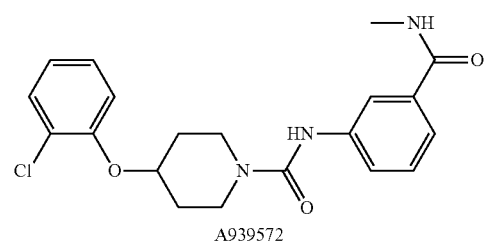

A939572

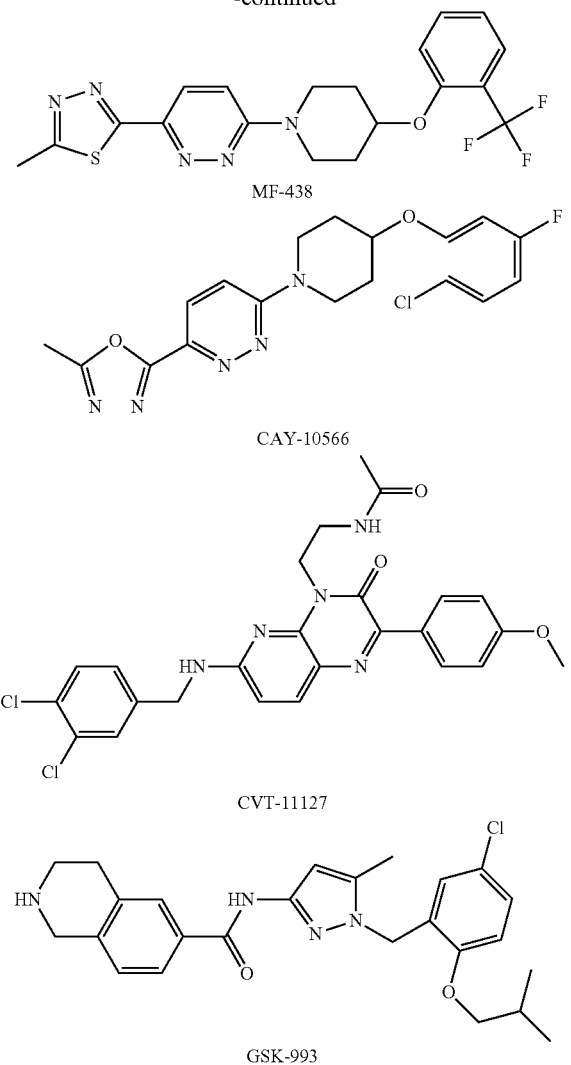

MF-438

CAY-10566

CVT-11127

GSK-993

In some embodiments, the SCD1 inhibitor is MF-438, CAY-10566, A939572, CVT-11127 and/or GSK-993.

In some embodiments, the SCD1 inhibitor is TOFA, CAY-10566, A939572, CVT-11127 and/or GSK-993.

In some embodiments, the SCD1 inhibitor is TOFA, MF-438, A939572, CVT-11127 and/or GSK-993.

In some embodiments, the SCD1 inhibitor is TOFA, MF-438, CAY-10566, CVT-11127 and/or GSK-993.

In some embodiments, the SCD1 inhibitor is TOFA, MF-438, CAY-10566, A939572, and/or CVT-11127.

In some embodiments, the SCD1 inhibitor is CAY-10566, A939572, CVT-11127 and/or GSK-993.

In some embodiments, the SCD1 inhibitor is CAY-10566, A939572, MF-438 and/or GSK-993.

In some embodiments, the SCD1 inhibitor is CAY-10566, A939572, MF-438 and/or CVT-11127.

In some embodiments, the SCD1 inhibitor is CAY-10566, MF-438, CVT-11127 and/or GSK-993.

In some embodiments, the SCD1 inhibitor is A939572, MF-438, CVT-11127 and/or GSK-993.

In some embodiments, the SCD1 inhibitor is A939572, CVT-11127 and/or GSK-993.

In some embodiments, the SCD1 inhibitor is A939572, MF-438 and/or GSK-993.

In some embodiments, the SCD1 inhibitor is A939572, MF-438 and/or CVT-11127.

In some embodiments, the SCD1 inhibitor is CAY-10566, CVT-11127 and/or GSK-993.

In some embodiments, the SCD1 inhibitor is CAY-10566, MF-438 and/or GSK-993.

In some embodiments, the SCD1 inhibitor is CAY-10566, MF-438 and/or CVT-11127.

In some embodiments, the SCD1 inhibitor is A939572, CAY-10566 and/or GSK-993.

In some embodiments, the SCD1 inhibitor is A939572, MF-438 and/or CAY-10566.

In some embodiments, the SCD1 inhibitor is A939572, CAY-10566 and/or CVT-11127.

In some embodiments, the SCD1 inhibitor is TOFA, A939572 and/or CAY-10566.

In some embodiments, the SCD1 inhibitor is TOFA, A939572 and/or MF-438.

In some embodiments, the SCD1 inhibitor is TOFA, A939572 and/or CVT-11127.

In some embodiments, the SCD1 inhibitor is TOFA, A939572 and/or GSK-993.

In some embodiments, the SCD1 inhibitor is TOFA, CAY-10566 and/or MF-438.

In some embodiments, the SCD1 inhibitor is TOFA, CAY-10566 and/or CVT-11127.

In some embodiments, the SCD1 inhibitor is TOFA, CAY-10566 and/or GSK-993.

In some embodiments, the SCD1 inhibitor is TOFA, MF-438 and/or CVT-11127.

In some embodiments, the SCD1 inhibitor is TOFA, MF-438 and/or GSK-993.

In some embodiments, the SCD1 inhibitor is TOFA, CVT-11127 and/or GSK-993.

In some embodiments, the SCD1 inhibitor is A939572 and/or CAY-10566.

In some embodiments, the SCD1 inhibitor is A939572 and/or MF-438.

In some embodiments, the SCD1 inhibitor is A939572 and/or CVT-11127.

In some embodiments, the SCD1 inhibitor is A939572 and/or GSK-993.

In some embodiments, the SCD1 inhibitor is CAY-10566 and/or MF-438.

In some embodiments, the SCD1 inhibitor is CAY-10566 and/or CVT-11127.

In some embodiments, the SCD1 inhibitor is CAY-10566 and/or GSK-993.

In some embodiments, the SCD1 inhibitor is MF-438 and/or CVT-11127.

In some embodiments, the SCD1 inhibitor is MF-438 and/or GSK-993.

In some embodiments, the SCD1 inhibitor is CVT-11127 and/or GSK-993.

In some embodiments, the SCD1 inhibitor is TOFA and/or CAY-10566.

In some embodiments, the SCD1 inhibitor is TOFA and/or MF-438.

In some embodiments, the SCD1 inhibitor is TOFA and/or CVT-11127.

In some embodiments, the SCD1 inhibitor is TOFA and/or GSK-993.

In some embodiments, the SCD1 inhibitor is TOFA and/or MF-438.

In some embodiments, the SCD1 inhibitor is TOFA and/or A939572.

In some embodiments, the SCD inhibitor is a nucleic acid silencing sequence for an SCD1 (e.g., SCD1). siRNA for SCD1 is an exemplary nucleic acid silencing sequence.

As used herein, the term "nucleic acid silencing sequence" refers to a nucleic acid (e.g., RNA) comprising a sequence which is capable of specifically inhibiting or "silencing" the expression of a target gene (e.g., SCD1). In certain embodiments, the nucleic acid silencing sequence is capable of preventing complete processing (e.g., the full translation and/or expression) of an mRNA molecule through a post-transcriptional silencing mechanism. Nucleic acid silencing sequences include noncoding RNA molecules, for example RNA duplexes comprising paired strands, as well as precursor RNAs from which such small non-coding RNAs can be generated. Exemplary RNA silencing sequences include double-stranded RNAs (dsRNAs) such as siRNAs, miRNAs and shRNAs. In one embodiment, the nucleic acid silencing sequence is capable of inducing RNA interference. In another embodiment, the nucleic acid silencing sequence is capable of mediating translational repression.

According to an embodiment of the invention, the nucleic acid silencing sequence is specific to the target RNA (e.g., SCD1) and does not cross inhibit or silence a gene or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene.

RNA interference refers to the process of sequence-specific post-transcriptional gene silencing in animals mediated by short interfering RNAs (siRNAs).

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplate use of dsRNA to downregulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects [Strat et al., *Nucleic Acids Research*, 34:3803-3810 (2006); Bhargava et al., *Brain Res. Protoc.* 13:115-125 (2004); Diallo et al., *Oligonucleotides* 13:381-392 (2003); Paddison et al., *PNAS* 99:1443-1448 (2002); Tran et al., *FEBS Lett.* 573:127-134 (2004)].

In particular, the invention according to some embodiments thereof contemplates introduction of long dsRNA (over 30 base transcripts) for gene silencing in cells where the interferon pathway is not activated (e.g. embryonic cells and oocytes)—see for example Billy et al. [*PNAS* 98:14428-14433 (2001)] and Diallo et al. *[Oligonucleotides* 13:381-392 (2003)].

The invention according to some embodiments thereof also contemplates introduction of long dsRNA specifically designed not to induce the interferon and PKR pathways for down-regulating gene expression. For example, Shinagwa and Ishii *[Genes & Dev.* 17:1340-1345 (2003)] have developed a vector, named pDECAP, to express long double-strand RNA from an RNA polymerase II (Pol II) promoter. Because the transcripts from pDECAP lack both the 5'-cap structure and the 3'-poly(A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of a siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., a siRNA) may be connected to form a hairpin or stem-loop structure (e.g., a shRNA). Thus, as mentioned, the nucleic acid silencing sequence of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' [Brummelkamp et al., *Science* 296:550 (2002)] and 5'-UUUGUGUAG-3' [Castanotto et al. *RNA* 8:1454 (2002)]. It will be recognized by one of skill in the art that the resulting single chain oligonucleotide forms a stem-loop or hairpin structure comprising a double-stranded region capable of interacting with the RNAi machinery.

Synthesis of nucleic acid silencing sequences suitable for use with some embodiments of the invention can be effected as follows. First, the target mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl, ChemBiochem. 2:239-245 (2001)]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level.

Second, potential target sites are compared to an appropriate genomic database (e.g., human, mouse, rat etc.) using any sequence alignment software, such as the BLAST software available from the NCBI server. Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

It will be appreciated that the nucleic acid silencing sequence of some embodiments of the invention need not be limited to those molecules containing only RNA, but further encompasses chemically-modified nucleotides and non-nucleotides.

In some embodiments, the nucleic acid silencing sequence provided herein can be functionally associated with a cell-penetrating peptide. As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of some embodiments of the invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of some embodiments of the invention preferably include, but are not limited to, penetratin, transportan, pIsl, TAT(48-60), pVEC, MTS, and MAP.

According to some embodiments the nucleic acid silencing sequence is a miRNA.

The term "microRNA", "miRNA", and "miR" are synonymous and refer to a collection of non-coding single-stranded RNA molecules of about 19-28 nucleotides in length, which regulate gene expression. miRNAs are found in a wide range of organisms and have been shown to play a role in development, homeostasis, and disease etiology.

According to some embodiments the nucleic acid silencing sequence is a microRNA mimic.

The term "microRNA mimic" refers to synthetic non-coding RNAs that are capable of entering the RNAi pathway and regulating gene expression. miRNA mimics imitate the function of endogenous microRNAs (miRNAs) and can be designed as mature, double stranded molecules or mimic precursors (e.g., or pre-miRNAs). miRNA mimics can be comprised of modified or unmodified RNA, DNA, RNA-DNA hybrids, or alternative nucleic acid chemistries (e.g., LNAs or 2'-O,4'-C-ethylene-bridged nucleic acids (ENA)). For mature, double stranded miRNA mimics, the length of the duplex region can vary between 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. Preparation of miRNAs mimics can be effected by chemical synthesis methods or by recombinant methods.

In some embodiments, the SCD1 inhibitor is a compound as described herein (e.g., a PluriSIn compound described herein). PluriSIns #1 (isonicotinic acid N'-phenylhydrazide) and #6 (2-hydroxy-2-(thiophen-2-yl)-2-phenylacetic acid 4-methyl-N'-phenylhydrazide) are exemplary SCD inhibitors.

In some embodiments, the SCD inhibitor is a compound of Formula II (as described herein) and/or a compound of Formula I (as described herein), wherein $R^2$ of Formula I is selected from the group consisting of 2-methylbenzofuran-3-ylmethyleneamino, —NH—$R^5$ (as defined herein), and 4-chlorobenzamido. Such compounds comprise a phenylhydrazine moiety, a structure which is associated with SCD inhibition, as exemplified in the Examples section herein.

In some of these embodiments, $R^2$ is selected from the group consisting of —NH—$R^5$ (as defined herein), and 4-chlorobenzamido. In some of these embodiments, $R^2$ is selected from the group consisting of 2-methylbenzofuran-3-ylmethyleneamino and —NH—$R^5$ (as defined herein). In some of these embodiments, $R^2$ is —NH—$R^5$.

Additional SCD inhibitors which are suitable for use according to embodiments of the invention include, for example, thia-fatty acid substrate analogs (e.g., 9-thiastearic acid) such as described by Behrouzian and Buist [Prostaglandins, Leukotrienes and Essential Fatty Acids 68:107-112 (2003)]; cyclopropenoid fatty acids (e.g., sterculic acid (8-(2-octylcyclopropenyl)octanoic acid) and malvalic acid (7-(2-octylcyclopropenyl)heptanoic acid)) such as described by Raju and Reiser [J Biol Chem 242:379-384 (1967)]; conjugated long-chain fatty acid isomers such as described by Park et al. [Biochim Biophys Acta 1486:285-292 (2000)]; small molecule SCD1 inhibitors such as described by Liu et al. [J Med Chem 50:3086-3100 (2007)], by Zhao et al. [Bioorg Med Chem Lett 17:3388-3391 (2007)], and by Xin et al. [Bioorg Med Chem Lett 18:4298-4302 (2008)]; and SCD inhibitors as described in International Patent Applications having publication nos. WO 2005/011653, WO 2005/011654, WO 2005/011655, WO 2005/011656, WO 2005/011657, WO 2006/014168, WO 2006/034279, WO 2006/034312, WO 2006/034315, WO 2006/034338, WO 2006/034341, WO 2006/034440, WO 2006/034441, WO 2006/034446, WO 2006/086445, WO 2006/086447, WO 2006/101521, WO 2006/125178, WO 2006/125179, WO 2006/125180, WO 2006/125181, WO 2006/125194, WO 2007/044085, WO 2007/046867, WO 2007/046868, WO 2007/050124, WO 2007/130075, WO 2007/136746, WO 2008/074835, WO 2008/074835, WO 2008/074824, WO 2008/036715, WO 2008/044767, WO 2008/029266, WO 2008/062276, WO 2008/127349, WO 2006/130986, WO 2007/009236, WO 2007/056846, WO 2007/071023, WO 2007/134457, WO 2007/143823, WO 2007/143824, WO 2008/017161, WO 2008/046226, WO 2008/064474, WO 2008/003753, WO 2007/143697, WO 2008/024390, WO 2008/096746 and WO 2008/056687, and in U.S. Patent Application No. 2008/0182838, and by Liu [*Expert Opinion on Therapeutic Patents* 19:1169-1191 (2009)]. In some embodiments, an SCD inhibitor is an anti-sense oligonucleotide, for example, an oligonucleotide suitable for effecting RNA interference of SCD-1, as described by Morgan-Lappe et al. [*Cancer Research* 67:4390-4398 (2007)].

The teachings of all of the above-cited documents are incorporated by reference as if fully set forth herein.

It is expected that during the life of a patent maturing from this application many relevant SCD inhibitors (e.g., SCD1 inhibitors) will be developed and the scope of the term "SCD inhibitor" is intended to include all such new technologies a priori.

In some embodiments, contacting the undifferentiated cells (e.g., pluripotent stem cells) with the SC inhibitor is effected in vitro (e.g., as described herein with respect to the compounds described herein).

In some embodiments, contacting is effected ex vivo (e.g., as described herein with respect to the compounds described herein).

In some embodiments, the SCD inhibitor (as described in any of the aspects of the invention) is a compound described herein. In some embodiments, the compound comprises a substituted or non-substituted phenylhydrazine moiety and/or is a derivative of a substituted or non-substituted phenylhydrazine.

According to an aspect of some embodiments of the present invention there is provided a use of a compound described herein (e.g, an SCD inhibitor described herein) in the treatment of a proliferative disease or disorder associated with proliferating cells characterized by a sensitivity to SCD inhibition.

According to an aspect of some embodiments of the present invention there is provided a use of a compound described herein (e.g, an SCD inhibitor described herein) in the manufacture of a medicament for in the treatment of a proliferative disease or disorder associated with proliferating cells characterized by a sensitivity to SCD inhibition.

According to an aspect of some embodiments of the present invention there is provided a method of treating a proliferative disease or disorder associated with proliferating cells characterized by a sensitivity to SCD inhibition, which is effected by contacting undifferentiated cells with a compound described herein (e.g, an SCD inhibitor described herein). In some embodiments, the undifferentiated cells are pluripotent stem cells.

According to an aspect of some embodiments of the present invention there is provided a pharmaceutical composition comprising a therapeutically effective amount of a compound described herein (e.g, an SCD inhibitor described herein) and a pharmaceutically acceptable carrier. In some embodiments, such a composition is formulated, identified for use, and/or packaged as described herein.

In some embodiments, the proliferative disease or disorder associated with proliferating cells characterized by a sensitivity to SCD inhibition is a cancer.

As further exemplified herein, the present inventors have uncovered a novel and efficient technique for identifying compounds for inhibiting undifferentiated cells, which may be used, for example, as lead candidates in a search for useful inhibitors of undifferentiated cells.

Thus, according to another aspect of embodiments of the invention, there is provided, a method of identifying a lead candidate for inhibiting undifferentiated cells, the method comprising:
  (a) providing a plurality of samples of undifferentiated cells, each of the samples comprising a different type of undifferentiated cells;
  (b) contacting the samples with a candidate compound; and
  (c) monitoring a viability of the undifferentiated cells in the samples, whereby if the viability is reduced in at least two of the samples, the candidate compound is identified as capable of inhibiting undifferentiated cells, thereby identifying the lead candidate.

In exemplary embodiments, the undifferentiated cells are pluripotent stem cells, the method being for identifying a lead candidate for inhibiting pluripotent stem cells.

In some embodiments, the plurality of samples of undifferentiated cells (e.g., pluripotent stem cells) comprises at least three samples. In some embodiments, the plurality of samples of undifferentiated cells (e.g., pluripotent stem cells) comprises at least four samples. In some embodiments, the plurality of samples of undifferentiated cells (e.g., pluripotent stem cells) comprises at least five samples.

In some embodiments, viability is reduced in at least three of the samples of undifferentiated cells (e.g., pluripotent stem cells). In some embodiments, viability is reduced in at least four of the samples. In some embodiments, viability is reduced in at least five of the samples.

In some embodiments, viability is reduced in all of the samples of undifferentiated cells (e.g., pluripotent stem cells), or in all of the samples except for one sample. In some embodiments, viability is reduced in all of the samples.

In some embodiments, the method is for identifying a lead candidate for selectively inhibiting undifferentiated cells (e.g., pluripotent stem cells), the method further comprising:
  (d) providing at least one sample of differentiated cells;
  (e) contacting the at least one sample with the compound identified as capable of reducing an undifferentiated cell population (e.g., a pluripotent stem cell population); and
  (f) monitoring a viability of the differentiated cells in the at least one sample, whereby if the viability is maintained in the at least one sample, the compound is identified as capable of selectively inhibiting undifferentiated cells (e.g., pluripotent stem cells).

In some embodiments, the compound is contacted with a plurality of samples of differentiated cells. In some embodiments, the plurality of samples of differentiated cells comprises at least three samples. In some embodiments, the plurality of samples of differentiated cells comprises at least four samples. In some embodiments, the plurality of samples of differentiated cells comprises at least five samples. In some embodiments, the plurality of samples of differentiated cells comprises at least six samples. In some embodiments, the plurality of samples of differentiated cells comprises at least seven samples. In some embodiments, the plurality of samples of differentiated cells comprises at least eight samples.

In some embodiments, viability is reduced in none of the samples of differentiated cells, except for one sample. In some embodiments, viability is reduced in none of the samples.

Suitable undifferentiated cells (e.g., pluripotent stem cells, undifferentiated cancer cells) and differentiated cells are described in the Examples below.

In some embodiments, the differentiated cells are derived from the undifferentiated cells (e.g., by differentiation of pluripotent stem cells and/or undifferentiated cancer cells), or vice versa (e.g., by induction of pluripotency and/or malignancy of differentiated cells).

In some embodiments, a plurality of candidate compounds are tested as described herein. In some embodiments, at least 5 candidate compounds are tested. In some embodiments, at least 10 candidate compounds are tested. In some embodiments, at least 20 candidate compounds are tested. In some embodiments, at least 50 candidate compounds are tested. In some embodiments, at least 100 candidate compounds are tested. In some embodiments, at least 200 candidate compounds are tested. In some embodiments, at least 500 candidate compounds are tested. In some embodiments, at least 1000 candidate compounds are tested. In some embodiments, at least 2000 candidate compounds are tested. In some embodiments, at least 5000 candidate compounds are tested. In some embodiments, at least 10000 candidate compounds are tested. In some embodiments, at least 20000 candidate compounds are tested. In some embodiments, at least 50000 candidate compounds are tested.

Monitoring of viability may be performed according to techniques known in the art, for example, an assay described herein.

In some embodiments, viability is monitored using a spectroscopic assay of cell viability. Spectroscopic assays may provide an ability to assay many samples (e.g., different cell types and/or different candidate compounds) in an efficient and non-costly manner.

The terms "comprises", "comprising", "includes", "including", "having" and their conjugates mean "including but not limited to".

The term "consisting of" means "including and limited to".

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the terms "treat", "treating", "treatment" and the like include abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

Materials

A939572 was obtained from BioFine International (Vancouver, Canada);
activin A was obtained from R&D Systems;
amsacrine hydrochloride was obtained from Sigma-Aldrich;
bovine serum albumin was obtained from Sigma-Aldrich;
CAY10566 was obtained from Cayman Chemical;
2',7'-dichlorofluorescein was obtained from Sigma-Aldrich;

chloroform was obtained from Sigma-Aldrich;
dithiothreitol (DTT) was obtained from Bio-Lab (Israel);
DMEM (Dulbecco's modified Eagle medium) was obtained from Sigma-Aldrich;
DMEM/F12 (1:1) medium was obtained from Sigma-Aldrich;
DMSO (dimethyl sulfoxide) was obtained from Sigma-Aldrich;
fetal bovine serum was obtained from Biological Industries (Beit Haemek, Israel);
FGF-2 (fibroblast growth factor 2) was obtained from PeproTech;
Folch solution was obtained from Sigma-Aldrich;
G418 geneticin sulfate was obtained from GIBCO;
glutamine was obtained from Biological Industries (Beit Haemek, Israel);
glutardialdehyde was obtained from Sigma-Aldrich;
hCG (human chorionic gonadotropin) was obtained from Sigma-Aldrich;
isopropanol was obtained from Sigma-Aldrich;
knockout DMEM medium was obtained from Invitrogen;
knockout serum replacement was obtained from Invitrogen;
leukemia inhibitory factor (LIF) was obtained from Invitrogen;
β-mercaptoethanol was obtained from Sigma-Aldrich;
M2 medium was obtained from Sigma-Aldrich;
M16 medium was obtained from Sigma-Aldrich;
Matrigel™ matrix was obtained from BD Biosciences;
methanol was obtained from Sigma-Aldrich;
methionine was obtained from Biological Industries (Beit Haemek, Israel);
methylene blue was obtained from Sigma Aldrich;
mineral oil was obtained from Sigma-Aldrich;
mTeSR1 defined medium was obtained from STEMCELL Technologies (Vancouver, Canada);
n-hexane was obtained from Sigma-Aldrich; nonessential amino acids were obtained from Invitrogen;
oleic acid ([$1$-$^{14}$C]-labeled and non-labeled, and oleic acid-albumin) was obtained from Sigma-Aldrich;
penicillin was obtained from Biological Industries (Beit Haemek, Israel);
PMSG (pregnant mare's serum gonadotropin) was obtained from Sigma-Aldrich;
puromycin was obtained from Sigma-Aldrich;
retinoic acid was obtained from Sigma-Aldrich;
RPMI-1640 medium was obtained from Invitrogen;
S$^{35}$-labeled methionine was obtained from Izotop (Hungary);
skim milk (powder) was obtained from Difco;
sodium butyrate was obtained from Sigma-Aldrich;
sodium pyruvate was obtained from Sigma-Aldrich;
stearic acid ([$1$-$^{14}$C]-labeled and non-labeled) was obtained from Sigma-Aldrich;
streptomycin was obtained from Biological Industries (Beit Haemek, Israel);
trichloroacetic acid was obtained from Merck Millipore;
Triton X-100 was obtained from Sigma-Aldrich;
trypsin-EDTA was obtained from Biological Industries (Beit Haemek, Israel);
Z-VAD-FMK was obtained from Santz Cruz Biotechnology.
Cell Lines:
BJ fibroblasts (immortalized) were obtained from Clontech Laboratories;
BJ-iPS28 induced pluripotent stem cells were derived as described in Pick et al. [*Stem Cells* 27:2686-2690 (2009)];
CSES2 human embryonic stem cells were derived as described in Lavon et al. [*Stem Cells* 26:1874-1882 (2008)];
CSES2-SO2/3 embryonic stem cells were derived as described in Kopper & Benvenisty [*Stem Cell Research* 8:335-345 (2011)];
Human embryonic stem cell-derived hepatocytes were obtained from Cellartis (Goteborg, Sweden), and handled according to the manufacturer's instructions;
Human induced pluripotent stem cell-derived cardiomyocytes were obtained from Cellular Dynamics International (Madison, Wis.), and handled according to the manufacturer's instructions;
Mel-1 human embryonic stem cells were obtained from Millipore.

Cell Culture:
The human embryonic stem (ES) cell lines H9 [Thomson et al. *Science* 282:1145-1147 (1998)], CSES2, CSES2-SO2/3 and Mel-1, and the induced pluripotent stem (iPS) cell line BJ-iPS28, were cultured without feeder cells in CELLSTAR® 10 cm tissue culture dishes (Greiner Bio-One) pre-coated with Matrigel™, using mTeSR1 defined medium supplemented with penicillin (50 U/ml) and streptomycin (50 µg/ml). Cells were passaged using Accutase™ (Millipore).

The neuroblastoma cell line Kelly was cultured in RPMI-1640 medium, supplemented with 15% fetal bovine serum (FBS), penicillin (50 U/ml) and streptomycin (50 µg/ml).

The hepatocarcinoma cell line Huh-7 was cultured in a DMEM/F12 (1:1) medium, supplemented with 10% FBS, penicillin (50 U/ml) and streptomycin (50 µg/ml).

The cervical carcinoma cell line HeLa, teratocarcinoma cell line NTERA-2, and immortalized BJ fibroblast cell line, were cultured in DMEM supplemented with 10% FBS, penicillin (50 U/ml) and streptomycin (50 µg/ml).

CSES2-SO2/3 embryonic stem cells were differentiated to endodermal progenitors using an established protocol [Duan et al. *Stem Cells* 28:674-686 (2010)]. Undifferentiated cells were seeded at a density of 10,000 cells/cm$^2$ on Matrigel™-coated plates, with mTeSR1 medium. The next day (day 1), medium was replaced to serum-free RPMI-1640, supplemented with 2 mM glutamine, 100 ng/ml Activin A 60 µg/ml of G418 geneticin sulfate and 0.3 µg/ml of puromycin. From day 3 to day 8, the same medium was also supplemented with 1×B27 supplement (Invitrogen) and 0.5 mM sodium butyrate. The cellular identity of the cells as endodermal progenitors was verified by quantifying the percentage of green SOX17+ cells, and the percentage of CXCR4+ cells, using a Guava® EasyCyte™ Plus flow cytometry system (Millipore). Further validation was obtained by fluorescence-staining of the cells with an antibody against the early endodermal surface marker CXCR4 (CXCR4-PE antibody, 1:25; BD Biosciences). The percentage of CXCR4+ cells was also quantified using the Guava® EasyCyte™ Plus flow cytometry system.

Human ES cells (SA001) were differentiated to neural stem cells (NSCs) using a dual SMAD inhibition protocol as described in Chambers et al. [*Nature Biotechnology* 27:275-280 (2009)]. Protocol for generation of neural progenitor cells from hPSCs (STEMCELL Technologies) was adjusted so that neural aggregates were comprised of up to 5,000 cells; neuroepithelial cell induction medium was N2B27 (Invitrogen), supplemented with 0.2% SB431542 10 mM (Tocris), 0.2% human Noggin 133 µg/ml (PeproTech), and 0.05% human FGF-2 10 µg/ml.

Human ES cells (SA001) were differentiated to mesenchymal stem cells (MSCs) using a protocol such as described in Lai et al. [*Methods Mol Biol* 698:141-150 (2011)]. Protocol was adjusted so that cells were grown for 10-15 days with knockout DMEM, 20% FBS, 1% nonessential amino acids, 1% Glutamax (Invitrogen), 0.1% penicillin and streptomycin, 0.1% β-mercaptoethanol, 0.1% FGF-2 10 µg/ml, and 1% ascorbic acid 2-phosphate (100 mM). Cells were passaged 3-6 times to obtain a stable phenotype.

R1 Oct4-GFP mouse embryonic stem cells [Yeom et al. Development 122:881-894 (1996)] were grown on gelatin-coated plates with DMEM, 15% FBS, 1 mM sodium pyruvate, 0.1 mM nonessential amino acids, 0.1 mM β-mercaptoethanol, and 1000 U/ml leukemia inhibitory factor (LIF).

Chemical Library Screening:

The CellTiter-Glo® luminescent cell viability assay (Promega, Madison, Wis.) was implemented as a high-throughput screening (HTS) assay for a chemical library screen in a 384-well format. After the DMSO tolerance of the assay was assessed, and the optimal cell numbers were determined for each cell type, a pilot screen was performed with the following 50 commercially available compounds:

3-acetamidophenol, 4-acetamidophenol, 6-methylcoumarin, acetaminophen, acetazolamide, actidione, amantadine hydrochloride, aminosalicylic acid, amodiaquine, amsacrine hydrochloride, aztreonam, caffeine, carboplatin, cefamandole sodium, cholic acid, ciprofloxacin, clozapine, coumarin, crotaline, diflunisal, dopamine, doxycycline, erythromycin, estradiol, famotidine, fenofibrate, fludrocortisone acetate, gentamicin, imipramine, isoniazid, isoproterenol, kanamycin, ketoconazole, L-thyroxine, mefenamic acid, nadolol, nalbuphine hydrochloride hydrate, nizatidine, norepinephrine, phenobarbital, quinine hydrochloride, salicylate, sodium 2-mercapto-ethanesulfonate, sulfasalazine, sulindac, tetracycline, tetraethylthiarum disulfide, timolol maleate, valproic acid sodium, and WY-14643.

For a primary screen, a 52,448 compound screening library assembled with Roche internal compounds (referred to as the "golden" library) was tested in a 384-well format. Compounds were distributed in 384-well plates (352 compounds per plate) as 0.5 µl of 4 mM DMSO solutions. For confirmation screens, counter-screens and compound profiling screens, compounds that were defined as "hits" were obtained from a Roche proprietary compound inventory, and distributed in a 384-well format as 8 µl of 5 mM DMSO solutions.

5,000 CSES2 cells were plated in 50 µl per well of mTeSR1 medium into black 384-well clear-bottom plates (Falcon BD) pre-coated with Matrigel™ using WellMate cell dispenser (Matrix, Hudson, N.H.). 24 hours after plating, medium was replaced with 25 µl of fresh medium and 25 µl of 40 µM compound medium solutions in 1% DMSO from the intermediate compound dilution plates. The plates were incubated at 37° C., in a 5% $CO_2$ atmosphere, for the entire duration of the screen, apart from the time required for liquid handling. Cell viability was determined 24 hours after compound treatment using CellTiter-Glo® luminescent cell viability assay kits. 50 µl of CellTiter-Glo® reagent was added to each well of the assay plates and fully mixed. After incubation at room temperature for 15 minutes, 25 µl of liquid was transferred from each well into a white opaque-bottom 384-well plate (PerkinElmer), and luminescence was measured using an EnVision® plate reader (PerkinElmer). 16 neutral control wells (0.5% DMSO) and 8 positive control wells (5 µM amsacrine hydrochloride were used to normalize the compound effect. All liquid transfer steps were handled with a Biomek® FXP Laboratory Automation Workstation (Beckman Coulter, Fullerton, Calif.) and Multidrop Combi liquid dispenser (Thermo Fisher, Waltham, Mass.). An Assay Analyzer (Genedata, Basel, Switzerland) was used for data pattern correction and calculation. The Spotfire software (Spotfire, Somerville, Mass.) was used for data illustration.

The compounds identified as hits from the primary screen were retested at a concentration of 20 µM against three pluripotent stem cell lines (CSES2, H9 and CSES2-SO2/3) for confirmation screens.

696 confirmed hits from the confirmation screen were tested for profiling in a panel of 13 different cell types, using the same screening protocol described above (except in the case of embryonic stem cell-derived neural stem cells (NSCs) and mesenchymal stem cells (MSCs), for which the protocol is described below). As discussed below, compounds were tested either in dose-dependent multiple concentration manner or in single concentration manner. CSES2 and CSES2-SO2/3 cell lines and the early endodermal progenitors derived from this cell line (CSES2-SO2/3-differentiated) were screened at 8 concentrations ranging from 50 µM to 23 nM with 1:3 serial dilution steps. BJ-iPS28 cell line and the BJ fibroblasts from which it was derived were screened at 6 concentrations ranging from 50 µM to 200 nM with 1:3 serial dilution steps. Cardiomyocytes were screened in one concentration of 20 µM. HeLa and NTERA-2 cell lines were screened in duplicates of 20 µM. Kelly and Huh-7 were screened in triplicates of 20 µM. Hepatocytes were screened in duplicates of 20 µM in the original 96-well plates in which the cells arrived (40,000 cells per well, in 160 µl medium, the volumes of all reagents involved were adjusted accordingly). MSCs and NSCs were screened in duplicates of 12.5 µM.

MSCs and NSCs were plated in white 384-well clear-bottom plates (Corning Inc.) pre-coated with poly-omithin/laminin Cells were seeded at a density of 4,000 cells per well in 38 µl medium. After incubation for 4 hours, 2 µl of pre-diluted compounds were added to the cells to a final concentration of 12.5 µM with 0.25% DMSO. Cells were incubated with the compounds for 24 hours, then 25 µl of medium were removed and 15 µl of CellTiter-Glo® reagent were added to the plate. The luminescence signal was read within one hour.

The raw intensity data for each well were background-corrected by subtraction of the median intensities across all positive control wells on the same plate, and used to calculate the inhibitory effect of each compound per cell line. A Genedata Assay Analyzer and Condoseo were used for data pattern correction, calculation and $IC_{50}$ curve fitting. A Z' factor was determined for each plate.

Alkaline Phosphatase Staining, Immunocytochemistry and Immunoblotting:

Alkaline phosphatase staining was performed according to the instructions of the Leukocyte Alkaline Phosphatase Kit (Sigma-Aldrich).

For immunocytochemistry staining, cells were washed twice with PBS (phosphate buffer saline), fixed with PBS containing 4% (w/v) paraformaldehyde for 30 minutes at room temperature, permeabilized with 0.2% Triton X-100, and blocked for 2 hours with PBS containing 3% (w/v) bovine serum albumin (BSA). Staining with primary antibodies was performed with the following antibodies (diluted in blocking buffer as indicated): mouse anti-human Oct3/4 (IgG, 1:200, SantaCruz Biotechnology), goat anti-human NANOG (IgG, 1:100, R&D Systems). Cells were incubated overnight at 4° C. with primary antibody, washed, and incubated with Alexa Fluor secondary antibodies (Invitrogen) for 2 hours.

For immunoblotting, 10% polyacrylamide gel was used for protein separation and detection. The gel was transferred to a nitrocellulose membrane and antibody hybridization and chemiluminescence were performed according to standard procedures. The primary antibodies in this analysis were rabbit anti-phosphorylated-eIF2α (1:250, Cell Signaling Technology), rabbit anti caspase-3 (1:1,000, Cell Signaling Technology), mouse anti β-catenin (1:10,000, BD Biosciences) and mouse anti-α-tubulin (1:50,000, Sigma-Aldrich). Horseradish peroxidase-conjugated anti-rabbit and anti-mouse secondary antibodies were obtained from Jackson Immunoresearch Laboratories.

RNA Isolation, Reverse Transcription and Quantitative PCR:

Total RNA was extracted using PerfectPure™ RNA Cultured Cell Kit (5 Prime). One microgram of total RNA was used for reverse transcription reaction using ImProm-II™ reverse transcriptase (Promega). Quantitative real-time PCR was performed with 1 µg of RNA reverse transcribed to cDNA and Power SYBR® Green PCR Master Mix (Applied Biosystems) and analyzed with the 7300 real-time PCR System (Applied Biosystems). Primer sequences for spliced XBP1 (sXBP1) were ctgctgagtccgcagcaggtgca (forward) and ggtccaagttgtccagaatgc (reverse); primer sequences for RPB1 were tgcgcaccatcaagagagtc (forward) and ctccgtcacagacattcgctt (control); Taqman probes for OCT4, NANOG and GAPDH were: Hs 00005111_g1, Hs 02387400_g1 and Hs 99999905_m1, respectively.

Cell Viability Assays:

For the high-throughput screens, relative cell number was determined using a CellTiter-Glo® Luminescent Cell Viability Assay as described hereinabove.

Otherwise, relative cell numbers were determined by fixating the cells with 0.5% glutardialdehyde and staining with methylene blue dissolved in 0.1 M boric acid (pH 8.5). Color extraction was performed using 0.1 M hydrochloric acid, and the staining (which is proportional to cell number) was quantified by measuring absorbance at a wavelength of 650 nm.

FACS Analysis:

For quantification of human embryonic stem cell-derived endodermal progenitor cells, cells were dissociated with Accutase™ (Millipore), filtered with a 40 µM nylon cell strainer (Falcon BD), and washed twice with PBS. Dissociated cells were suspended at a final concentration of $10^5$ cells/ml. Cells were incubated on ice with CXCR4-PE antibody (1:25 dilution, BD Biosciences) for 1 hour, washed twice with PBS, suspended in PBS with 2% FBS, and analyzed using a Guava® EasyCyte™ Plus flow cytometer system (Millipore) with Guava® Express software (Millipore).

For quantification of remaining undifferentiated cells after treatment, cells were treated with 20 µM PluriSIn #1 (isonicotinic acid N'-phenylhydrazide) for 48 hours or 72 hours, dissociated using TrypLE™ Select (Invitrogen), and washed with PBS supplemented with 10% FBS and 0.05% sodium azide. Dissociated cells were suspended to a final concentration of $10^6$ cells/ml. Cells were incubated on ice with TRA1-60-PE antibody (1:40, BD Biosciences), washed and analyzed using LSR II FACS (BD Biosciences) with FCS Express software (De Novo Software, Los Angeles, Calif.).

For quantification of apoptosis, an Annexin V-FITC Apoptosis Detection Kit (eBioscience) was used. Cells were treated with 20 µM PluriSIn #1 for 16 hours, dissociated using TrypLE® Select, and washed with PBS supplemented with 10% FBS and 0.05% sodium azide. Dissociated cells were suspended at a final concentration of 2-5×$10^5$ cells/ml, and treated according to the manufacturer's instructions. Analysis was performed using LSR II FACS with FCS Express software.

Microscopy Imaging:

High content imaging of CSES2-SO2/3 fluorescent cells (mCherry+ or EGFP+) was performed in black clear-bottom 384-well assay plates (Falcon BD), using the Opera high-content screen imaging platform (PerkinElmer). Otherwise, light and fluorescence imaging of all cells was performed in 24-well, 6-well or 10 cm CELLSTAR® plates (Greiner Bio-One), using an Olympus CellR imaging station. Light imaging of developing mouse embryos was performed in 35 mm culture dishes (Falcon BD), using an Olympus IX70 microscope.

Global Gene Expression Analysis:

Human embryonic stem cells, and early endodermal progenitors derived from human embryonic stem cells, were treated for 12 hours with the compounds PluriSIn #1 (isonicotinic acid N'-phenylhydrazide) or PluriSIn #6 (2-hydroxy-2-(thiophen-2-yl)-2-phenylacetic acid 4-methyl-N'-phenylhydrazide), or with 0.2% DMSO control. Total RNA was extracted using a PerfectPure™ RNA Cultured Cell Kit (5 Prime) according to the manufacturer's protocol, and analyzed using a Human Genome U133A 2.0 microanay platform (Affymetrix); washing and scanning were performed according to the manufacturer's protocol. Original microarray data are accessible at the NCBI Gene Expression Omnibus (GEO) database under the accession number GSE37040.

Arrays were normalized using the MASS algorithm in the Affymetrix Expression Console. Probe sets absent in both control and treatment conditions were filtered out by the MASS Absent/Present call. Probe sets with expression values lower than 50 were raised to this level. Using a 2-fold threshold, a list of differentially expressed genes was comprised for each pair of conditions: embryonic stem cells treated with PluriSIn #1 vs. control, ESCs treated with PluriSIn #6 vs. control, and endodermal progenitor cells treated with PluriSIn #1 vs. control.

To detect significantly over-represented GO (gene ontology) biological processes, the lists of differentially expressed genes were subjected to the DAVID functional annotation clustering tool (wwwdotdaviddotabccdotncifcrfdotgov).

To discover similarities between the gene expression alterations induced by PluriSIns and those induced by known drugs, the lists of differentially expressed genes were subjected to a connectivity map (cmap) analysis, according to developer's instructions (wwwdotbroadinstitutedotorg/cmap).

The lists of differentially expressed genes were used as inputs for unsupervised hierarchical clustering, performed with Partek Genomics Suite version 6.3 (Partek, St. Louis, Mo.).

Metabolic Labeling of Protein Synthesis:

H9 embryonic stem cells were seeded in Matrigel™ pre-coated 6-well tissue culture plates at a density of 2×$10^5$ cells/well, and cultured using mTeSR1 defined medium. BJ fibroblasts were seeded in 6-well tissue culture plate at the same density, and cultured with DMEM supplemented with 10% FBS, penicillin (50 U/ml) and streptomycin (50 µg/ml). Cells were treated for 12 hours with either 20 µM PluriSIn #1 (isonicotinic acid N'-phenylhydrazide) or with 0.2% DMSO. Cells were then washed with PBS, and replenished with methionine-deficient medium for 1 hour. Metabolic labeling of the cells was then performed for 1 hour with 10 µCi of $S^{35}$-labeled methionine in 1 ml/well, in the presence of 20 µM PluriSIn #1 or 0.2% DMSO. Cells were washed with PBS containing 10 mM methionine, and were then lysed in 0.4 ml of 30% ice-cold trichloroacetic acid (TCA) containing 10 mM methionine for 15 minutes. A 3 MM pre-filter and a GF/C filter on top of it were set in a filtering apparatus, and a stainless still cylinder was assembled. The filter was pre-wet with 10% TCA under vacuum. TCA precipitates were collected by passing the content of each well through the filter, and were washed three times with 5% TCA, and once with ethanol. Filters were air-dried and were then subjected to liquid scintillation spectrometry using a Tri-Carb® 2900TR Liquid Scintillation Analyzer (PerkinElmer). Total protein concentration was determined using a Bradford Protein Assay (Sigma-Aldrich), and the radioactivity measurements were normalized accordingly. Experiments were preformed in triplicates.

SCD1 Activity Measurement:

Cells were plated in 6-well plates at a density of 50,000 to 100,000 cells per well. 24 hours later, 20 µM of PluriSIn #1 (isonicotinic acid N'-phenylhydrazide) or 0.2% DMSO (control) were added to the cells. After 12 hours of incubation at 37° C., under 5% $CO_2$, the old medium was removed, cells were washed with PBS, and new medium containing 2.3 µM of 0.75 UCi of [1-$^{14}$C] stearic acid was added. The cells were then incubated for up to 4 hours at 37° C., under 5% $CO_2$.

After the incubation period, the medium was discarded and the cells were washed 3 times with 2 ml of PBS. 2 ml of an n-hexane: isopropanol mixture (3:2 v:v) were added, and the cells were then incubated for 30 minutes at a temperature of 37° C., under 5% $CO_2$. 2 ml of Folch solution (a 2:1 (v:v) chloroform: methanol mixture) were subsequently added. The liquid was transferred to tubes for phase partition by adding 1 ml water. The lower organic phase was evaporated and used for lipid saponification and TLC (thin layer chromatography) separation of the free [1-$^{14}$C] stearic acid (substrate) and [1-$^{14}$C] oleic acid (formed product). Lipids extracted from the cells were applied to TLC plates previously immersed in 10% $AgNO_3$ and activated at a temperature of 120° C. for 60 minutes. Unlabeled stearic and oleic acid were added to each application point as carriers and as internal standards for identification. The plates were then run with a solvent mixture of chloroform: methanol: acetic acid: double distilled water (DDW) (90:8:1:0.8). The free fatty acids were detected by ultraviolet illumination after spraying the TLC with a 2',7'-dichlorofluorescein solution. The spots corresponding to stearic and oleic acid were scraped and the radioactivity counted in a Packard Tri-Carb® 1600TR scintillating counter. SCD1 desaturase activity was calculated from the percent conversion of substrate to product and the conversion to picomoles per minute per $10^6$ cells. Experiments were performed in triplicates.

Oleic Acid Rescue Assay:

Human embryonic stem cells were cultured without feeder cells in CELLSTAR® 24-well tissue culture plates (Greiner Bio-One) pre-coated with Matrigel™, using mTeSR1 defined medium. Cells were treated with 20 µM of tested PluriSIn compounds, 5 µM amsacrine hydrochloride, or 0.02% DMSO, in the presence or absence of either oleic acid-albumin or albumin alone. After 24 hours, the cells were subjected to microscopy imaging and to cell viability measurements.

In-Vitro Embryonic Development Experiments:

Superovulation was induced in female mice (CB6F1/OLAHSD and ICR:HSD (CD-1)), by injection of gonadotropins: intraperitoneal injection of 5 IU PMSG (pregnant mare's serum gonadotropin) at 1:00 P.M. was followed by an intraperitoneal injection of 5 IU hCG (human chorionic gonadotropin) 47 hours later, in accordance with the procedures described by Najy et al. [*Manipulating the mouse embryo: a laboratory manual*, 3$^{rd}$ Edn., Cold Spring Harbor Laboratory Press (2003)].

Females were mated with stud males immediately after the second injection, and plugging was evident the next morning. Pregnant female mice were sacrificed at approximately 36 hours p.c. (post coitum), and two-cell embryos were collected in accordance with the procedures described by Najy et al. [*Manipulating the mouse embryo: a laboratory manual*, 3$^{rd}$ Edn., Cold Spring Harbor Laboratory Press (2003)]. The abdominal cavity was opened, and the oviduct was cut and transferred to a Petri dish containing M2 medium at room temperature. The oviduct was flushed with M2 medium, and embryos were picked up using a pipette and washed in M2 medium to rinse off debris. Embryos were then transferred to microdrops of M16 medium. A 35 mm culture dish (Falcon BD) containing drops of 40 µl M16 medium, covered with mineral oil, was prepared the day before, and incubated overnight at a temperature of 37° C. under 5% $CO_2$. Embryos were then transferred to these microdrops following their collection, and incubated at a temperature of 37° C. under 5% $CO_2$. The development of the embryos was examined twice a day using light microscopy imaging. At the morula stage (approximately 3.5 days p.c.), embryos were transferred either to microdrops of 40 µl M16 medium with 20 µM PluriSIn #1 (isonicotinic acid N'-phenylhydrazide) in 0.2% DMSO, or to control microdrops with 0.2% DMSO. Other control embryos were left at the original microdrops to control for possible effects of the transfer itself. At approximately 4 days p.c. and 4.5 days p.c., the embryos were examined using light microscopy imaging, and blastocysts were graded as described by Cortes et al. [*Stem Cells and Development* 17:255-267 (2008)].

Teratoma Formation:

Human embryonic stem cell and induced pluripotent stem cell lines were cultured without feeder cells in CELLSTAR® 6-well tissue culture plates (Greiner Bio-One) pre-coated with Matrigel™, using mTeSR1 defined medium. Cells were treated for 24 hours with either 20 µM PluriSIn #1 (isonicotinic acid N'-phenylhydrazide) in 0.2% DMSO or with 0.2% DMSO, followed by medium replacement and a second treatment for another 24 hours. 48 hours after initial exposure to the tested compound, cells were harvested with trypsin-EDTA and resuspended in a 1:1 mTeSR1:Matrigel™ mixture to a total volume of 200 µl. Cells were then injected subcutaneously to the back of NOD-SCID IL2Rγ−/− mice (Jackson Laboratory). Six weeks after injection mice were sacrificed, the formation of tumors was examined, and the resulting teratomas were photographed, dissected and cryopreserved in O.C.T. compound (Sakura Finetek, Torrance, Calif.).

Alternatively, human embryonic stem cells and induced pluripotent stem cells were spontaneously differentiated in culture for a period of 10 days, by growing them on gelatin-coated culture plates with 85% knockout DMEM medium supplemented with 15% knockout serum replacement, 1 mM glutamine, 0.1 mM β-mercaptoethanol, 1% nonessential amino acids, penicillin (50 U/ml) and streptomycin (50 µg/ml), without basic fibroblast growth factor (bFGF). Retinoic acid was added to the medium at a final concentration of 1 µM. 10 days later, the differentiated cells were harvested and plated at a 1:1 ratio with their undifferentiated parental cells in CELLSTAR® 6-well tissue culture plates (Greiner Bio-One) pre-coated with Matrigel™, with mTeSR1 defined medium. Cells were treated for 24 hours with either 20 µM PluriSIn #1 or 0.2% DMSO, followed by medium replacement and a second treatment for another 24 hours. 48 hours after initial exposure to the compound, cells were harvested with trypsin-EDTA and counted using a Countess automated cell counter (Invitrogen). 1 million viable cells from each condition were resuspended in a 1:1 mTeSR1:Matrigel™ mixture to a total volume of 200 µl. Cells were then injected subcutaneously to the back of NOD-SCID IL2Rγ−/− mice. Each mouse was injected with PluriSIn #1-treated cells into one side of its body and control-treated cells into the other side. Six weeks after injection mice were sacrificed, the formation of tumors was examined, and the resulting teratomas were photographed, dissected and cryopreserved in O.C.T. compound.

SCD1 Knockdown:

For genetic ablation of SCD1, knockdown of SCD1 was performed using ON-TARGETplus SMART pool siRNA against human SCD1 (Dharmacon RNAi Technologies, Lafayette, Colo.). Transfection of siRNAs into human ES cells was performed as previously described [Ma et al., RNA 16:2564-2569 (2010), using the transfection reagent Lipofectamine 2000 (Invitrogen). siRNA oligos were used at a final concentration of 40 nM or 80 nM. siRNA against green fluorescent protein (GFP) was used as mock-siRNA (Integrated DNA Technologies, Coralville, Iowa). Cell viability was measured 72 hours after transfection.

Statistics:

Hierarchical clustering by profiles of gene expression levels, and by profiles of reaction to compounds, was performed with Partek Genomics Suite version 6.3 (Partek, St. Louis, Mo.).

Gene expression levels of selected genes, as well as SCD and protein synthesis activities between control and treated cells, were compared using a one-tailed Student's t-test.

For DAVID functional annotation analysis, a threshold for significance was determined as p=0.05 after applying Benjamini correction.

The enrichment significance for compounds with phenylhydrazine in the list of PluriSIn compounds, and that of protein synthesis inhibitors in the cmap results, were determined using Pearson's chi-square goodness-of-fit test. The significance of in-vitro embryonic development experiments was determined using Fisher's exact test.

Z' factors were calculated according to the formula:

$$1-[3(s.d.\ of\ pos.\ con.-s.d.\ of\ neg.\ con.)/|mean\ of\ pos.\ con.-mean\ of\ neg.\ con.|]$$

wherein s.d.=standard deviation; pos.=positive; neg.=negative; con.=control.

Example 1

Screen for Cytotoxicity Towards Stem Cells

In order to identify cytotoxic inhibitors of human pluripotent stem cells (hPSCs), a high-throughput screen (HTS) of small molecules was designed and used, as described hereinabove. To facilitate screening, a protocol was developed and optimized for enabling the culture of undifferentiated hPSCs in a 384-well format, the automatic application of small molecules to these cell plates, and the accurate assessment of cell viability after exposure of cells to tested compounds.

First, human embryonic stem (ES) cells and induced pluripotent stem (iPS) cells were grown on Matrigel™-coated plates without feeders, using a serum-free defined medium (mTeSR1).

The pluripotency of the cells under these conditions was evaluated by examining their morphology, by staining for alkaline phosphatase (AP), and by immunocytochemistry staining for Oct-4, as described hereinabove.

As shown in FIGS. 1A and 1B, the cells exhibited normal morphology (FIG. 1A) and expressed Oct-4 (FIG. 1B).

As shown in FIGS. 2A and 2B, the cells exhibited positive staining for alkaline phosphatase.

These results confirm the pluripotency of the stem cells.

Cells were then harvested and seeded in 384-well plates, at a density of 5,000 cells per well. Quantitative PCR and immunofluorescence-staining for Oct-4 and NANOG were performed in order to verify that the cells remained undifferentiated for at least 5 days under these conditions.

As shown in FIGS. 3 and 4, while growing in the plates, the cells maintained their normal morphology, formed colonies and proliferated, and remained undifferentiated for at least 5 days.

An ATP-based luminescent cell viability assay (CellTiter-Glo®) was used to accurately measure of the amount of living cells in a culture of undifferentiated cells, as described hereinabove.

As shown in FIG. 5, the observed ATP-based luminescence in undifferentiated cells was strongly correlated to the number of cells seeded in a sample 24 hours prior to measurement.

As shown in FIG. 6, assaying undifferentiated cell viability via methylene blue staining provided similar results to those obtained via ATP-based luminescent cell viability assay.

These results confirm that the ATP-based luminescent cell viability assay accurately measures the viability of the undifferentiated cells in culture.

A pilot screen was then performed with 50 commercially-available compounds (as described in the Materials and Methods section hereinabove), which were randomly selected from a bank of known cytotoxic compounds. Cells were exposed to the compounds at 5 different concentrations ranging from 30 µM to 300 nM, for 4 exposure durations (6, 24, 48 or 72 hours), and were then subjected to the viability assay.

As shown in FIG. 7, all of the tested compounds which exhibited observable cytotoxicity exhibited such activity at 24 hours. A test period of 24 hours was therefore chosen for the following primary screen.

Furthermore, as shown in FIG. 7, amsacrine hydrochloride (a DNA topoisomerase inhibitor), killed almost all cells within 24 hours, and cycloheximide (a translation inhibitor, also known in the art as actidione), resulted in an approximately 50% decrease in cell viability after 24 hours, at a concentration of 1-3 µM.

Based on these results, amsacrine hydrochloride was selected as a positive control for the primary screen, and cycloheximide (actidione) was selected as an $EC_{50}$ control (i.e., a control compound that results in 50% toxicity to the cells).

In the primary screen for cytotoxic inhibitors of hPSCs, 52,448 small molecules were screened against undifferentiated human ES cells, as described in the Materials and Methods section. These molecules belong to the "golden"

compound library of Hoffman-La Roche, which is comprised of diverse chemical entities. This library is designed to represent the entire compound library of the pharmaceutical company, which includes over one million distinct molecules.

The protocol for the primary screen is depicted schematically in FIG. 8. Human ES cells (CSES2) were grown on Matrigel™-coated plates with mTeSR1 defined medium. Prior to their plating in 384-well plates, pluripotency of the cells was verified by their morphology and by alkaline phosphatase staining Cells were then harvested, counted, and automatically dispensed at a density of 5,000 cells per well. The plates were incubated overnight to allow the cells to settle down properly. 149 such assay plates were prepared, to match the 149 compound plates of the "golden" library. 24 hours after cell plating, the compounds were diluted and transferred to the assay plates, such that each of the 52,448 compounds was added to one well, at a final concentration of 20 µM (with 0.5% DMSO). In addition to 352 compounds from the library, each assay plate also included its own controls: 16 wells with 0.5% DMSO only (negative control), 8 wells with 5 µM amsacrine hydrochloride (positive control), and 8 wells with 2 µM cycloheximide ($EC_{50}$ control). 24 hours after compound addition, a CellTiter-Glo® viability assay was used to quantify the number of living cells in each well. Luminescence intensity was measured in each well using a luminescence plate reader, and data were normalized and analyzed as described in the Materials and Methods section.

As shown in FIG. 9, the assay exhibited a consistently high Z' factor (0.078+/−0.06 per 384-well assay plate), indicating that the primary screen was very robust.

Hits were determined as compounds that induced over 60% inhibition. Using this threshold, 2,031 compounds (<4% of the tested compounds) were identified as hits. The distribution of the inhibition exhibited by the tested compounds is presented in FIG. 10.

These 2,031 hits were then selected to be retested in confirmation and validation assays against four human ES and iPS cell lines. The first confirmation screen was performed with two human ES cell lines, CSES2 and H9, at a single concentration (20 µM). The confirmation screen removed false positive hits from the primary screen, as well as compounds with cell line-specific effects.

As shown in FIG. 11, the confirmation screen resulted in 696 hits that were cytotoxic to both CSES2 and to H9 cells.

These 696 confirmed hits were then tested against the human ES cell line CSES2, and its clone CSES2-SO2/3, at 8 concentrations (ranging from 50 µM to 23 nM, with serial 1:3 dilution steps).

As shown in FIGS. 12A and 12C, the potencies of the compounds in the various tested human ES cell lines were very highly correlated. In addition, the cytotoxic effect of the compounds was dose-dependent in over 98% of cases.

As further shown in FIG. 12B, the potency of the compounds in iPS cells was highly correlated to those obtained for ES cells. No compounds were found to be cytotoxic toward one cell type without having a detrimental effect on the other.

In order to verify that the inhibitory effect of the compounds persists over time, CSES2 cells were exposed to the compounds at 6 concentrations for a 48 hour duration.

As shown in FIG. 13, the cytotoxic effect of each of the tested compounds was maintained for 48 hours. No cell recovery was observed following exposure to any of the compounds.

The effect of the selected compounds on human iPS cells was then determined BJ-iPS28 cells were grown at precisely the same conditions as the ES cells, and were tested at 6 concentrations (ranging from 50 µM to 200 nM, with serial 1:3 dilution steps).

These results indicate that the 696 compounds identified as described hereinabove are potent cytotoxic inhibitors of human PSCs.

Example 2

Screen for Compounds Exhibiting Selective Cytotoxicity Towards Stem Cells (PluriSIns)

In order to identify highly-selective cytotoxic inhibitors of hPSCs, the 696 cytotoxic inhibitors of hPSCs identified as described in Example 1 were counter-screened as described in the Materials and Methods section against other cell types, representative of all germ layers and developmental stages Importantly, many of these cell types were differentiated from human ES or iPS cells. The screened cell types included ES-derived neural stem cells (NSCs), ES-derived mesenchymal stem cells (MSCs), ES-derived endodermal progenitor cells, ES-derived hepatocytes, iPS-derived cardiomyocytes, iPS-derived fibroblasts of origin (BJ fibroblasts), and three cancer cell lines: neuroblastoma (Kelly), cervical cancer (HeLa) and hepatocarcinoma (Huh7). The cell types and their relationship to stem cells are depicted schematically in FIG. 14.

Each cell type was screened in a duplicate or a triplicate at a concentration of 20 µM, against most or all of the abovementioned 696 compounds.

As shown in FIGS. 15-21, there was little correlation between cytotoxicity of the tested compounds towards hPSCs and cytotoxicity towards cardiocytes (FIG. 15), fibroblasts (FIG. 16), hepatotcytes (FIG. 17), neuroblastoma (Kelly) cells (FIG. 18), HeLa cells (FIG. 19), or Huh7 cells (FIG. 20), although there was somewhat more correlation with cytotoxicity towards endodermal progenitor cells (FIG. 21).

These results stand in sharp contrast to the abovementioned results indicating that the potency of the compounds in different types of hPSCs were highly correlated (compare FIG. 15 with FIGS. 11 and 12A-12C).

In order to further verify the selective cytotoxicity of identified compounds, multiple concentrations of the compounds were screened against differentiated cells as well as against genetically matching undifferentiated cells.

CSES2-SO2/3 is a genetically-labeled cell line that expresses mCherry under the promoter of the pluripotency hallmark gene OCT-4, and GFP under the promoter of the early endodermal marker SOX17. Therefore, these cells are red while undifferentiated, and become green upon their differentiation into the endodermal lineage [Kopper & Benvenisty, *Stem Cell Research* 8:335-345 (2011)]. Green early endodermal progenitor cells were generated from the red undifferentiated cells, using an 8-day differentiation protocol as described by Duan et al. [*Stem Cells* 28:674-686 (2010)].

As shown in FIG. 22, the cells were red prior to differentiation, but after 8 days, most of the cells were green, whereas red undifferentiated cells could be hardly detected. These results indicate that the differentiation protocol was highly efficient.

The efficiency of the differentiation protocol was confirmed by FACS analysis for the endodermal marker CXCR4.

As shown in FIG. 23, 98% of the cells expressed the early endodermal marker CXCR4, thereby confirming the efficiency of the differentiation protocol.

As shown in FIG. 24, the differentiated cells remained viable and green after being plating in 384-well plates. This result indicated that the differentiated cells could be screened against the small molecules.

The identified compounds were screened at 8 concentrations using both the undifferentiated red cells and the differentiated green cells, and reliable $EC_{50}$ values were thereby calculated for the genetically identical differentiated and undifferentiated cells.

In addition, the identified compounds were screened at 6 concentrations using the BJ-fibroblasts from which the iPS line BJ-iPS28 had been derived, and reliable $EC_{50}$ values were thereby calculated for both the iPS cells and for their somatic cells of origin.

As shown in FIGS. 25A and 25B, many of the tested compounds exhibited potent cytotoxicity towards BJ-iPS28 (FIG. 25A) and CSES2-SO2/3 (FIG. 25B) pluripotent stem cells, but considerably less cytotoxicity towards genetically identical differentiated cells (BJ-fibroblasts (FIG. 25A) and differentiated CSES2-SO2/3 cells (FIG. 25B), respectively).

In order to identify compounds exhibiting highly selective cytotoxicity towards hPSCs, a threshold was set, characterized by approximately 80% or more inhibition (at 20 µM) in each of the tested hPSC types, with less than 20% inhibition (at 20 µM) in the tested non-hPSC cell types (with the exception of ES-derived neural stem cells, which are relatively similar to ES cells). Moreover, the criteria required that the $EC_{50}$ value be approximately 5 µM or lower for CSES2, CSES2-SO2/3 and BJ-iPS28 cells, but higher than 50 µM for the 8-day differentiated CSES2-SO2/3 cells and for the BJ-fibroblasts.

As shown in Tables 1, 2 and 3 below, 15 compounds met the abovementioned criteria or were close to meeting the abovementioned criteria (e.g., exhibited a more than 10-fold difference in $EC_{50}$ between hPSCs and differentiated cells), and were thus termed Pluripotent-Specific Inhibitors (PluriSIns). The 15 identified PluriSIns are shown in Table 1. As shown in Table 1, many (9 of 15) of the PluriSIns comprise a phenylhydrazine moiety. The inhibitory effects of the PluriSIns are presented in Tables 2 and 3.

TABLE 1

PluriSIn compound structures and chemical names (emphasis on shared moieties)

| PluriSIn # | Structure | Name |
|---|---|---|
| PluriSIn #1 | | isonicotinic acid N'-phenylhydrazide |
| PluriSIn #2 | | 1-phenylcarbamoyl-5-fluorouracil |
| PluriSIn #3 | | 5-[([1,1'-biphenyl]-4-yloxy)methyl]-1,3-benzenediamine |
| PluriSIn #4 | | N-[2-(4-methoxyphenyl)ethyl]-4-(1-piperidinyl)-benzamide |

TABLE 1-continued

PluriSIn compound structures and chemical names (emphasis on shared moieties)

| PluriSIn # | Structure | Chemical name |
|---|---|---|
| PluriSIn #5 | | 2-naphthalenesulfonic acid N'-phenylhydrazide |
| PluriSIn #6 | | 2-hydroxy-2-(thiophen-2-yl)-2-phenylacetic acid 4-methyl-N'-phenylhydrazide |
| PluriSIn #7 | | (E)-4-[2-(2,3-dihydro-1-methyl-1H-indol-5-yl)ethenyl]phenyl acetate |
| PluriSIn #8 | | 2-methyl-3-benzofurancarboxaldehyde N'-phenylhydrazone |
| PluriSIn #9 | HCl | acetylhydroximic acid 4-chloro-N'-phenylhydrazide (hydrochloride) |
| PluriSIn #10 | | hexanoic acid 4-chloro-N'-phenylhydrazide |
| PluriSIn #11 | | ethyl 2-[(3E)-2,4-dioxo-3-[(N'-phenylhydrazinyl)methylidene]pyrrolidin-1-yl]acetate |

TABLE 1-continued

PluriSIn compound structures and chemical names (emphasis on shared moieties)

PluriSIn #12

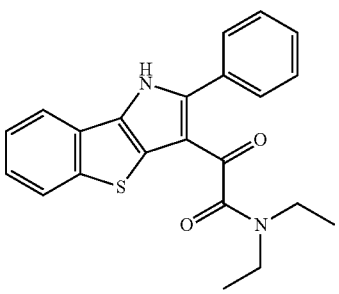 [SMILES: CCN(CC)C(=O)C(=O)c1c(-c2ccccc2)[nH]c2c1sc1ccccc12]

N,N-diethyl-α-oxo-2-phenyl-1H-[1]benzothieno[3,2-b]pyrrole-acetamide

PluriSIn #13

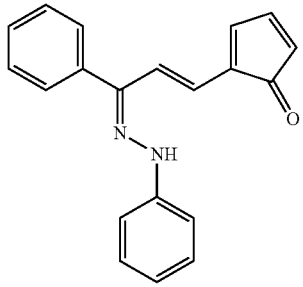 [SMILES: O=C1C=CC=C1/C=C/C(=N\Nc1ccccc1)c1ccccc1]

phenyl-3-(cyclopentadienone-2-yl)-2-propen-1-one N'-phenylhydrazone

PluriSIn #14

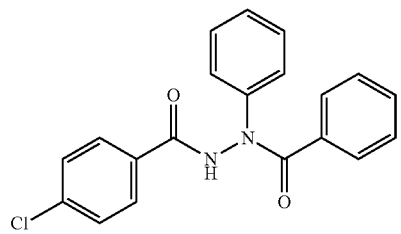 [SMILES: O=C(NN(C(=O)c1ccccc1)c1ccccc1)c1ccc(Cl)cc1]

N'-benzoyl 4-chlorobenzoic acid N'-phenylhydrazide

PluriSIn #15

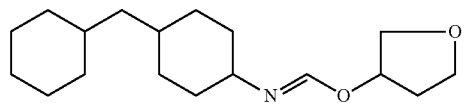

3-(4-(cyclohexylmethyl)cyclohexyl-iminomethoxy)tetrahydrofuran

TABLE 2

Inhibition (%) of various cell types by PluriSIn compounds (at 20 μM)

| | Pluripotent stem cells | | | | Stem cell-derived differentiated cells | | | | | Differentiated cells | | | |
|---|---|---|---|---|---|---|---|---|---|---|---|---|---|
| PluriSIn # | CSES2 | CSES2-H9 | BJ-SO2/3 | BJ-iPS28 | ES-derived neural stem cells | ES-derived mesenchymal stem cells | ES-derived endodermal progenitors | ES-derived hepatocytes | iPS-derived cardiomyocytes | BJ-fibroblasts | HeLa | Huh7 | Kelly |
| 1 | 92.1 | 88.6 | 90.8 | 85.4 | 18.2 | −4.9 | 6.5 | 16.2 | 15 | −8.8 | 5.7 | 5.8 | −2 |
| 2 | 84 | 65.4 | 54.3 | 56.8 | 53.6 | −1.4 | −8.3 | 13.2 | 4.4 | −8.3 | −2.1 | −0.2 | 3 |
| 3 | 98 | 109.6 | 97.4 | 81.1 | 90.4 | 3.3 | −9.2 | 2.8 | −2.9 | −25.4 | −4.2 | −5.9 | 2.3 |
| 4 | 84.7 | 74.1 | 74.5 | 74.8 | 15.5 | −8.1 | −1.1 | 10.5 | 14.1 | −22.9 | 2.2 | 12.1 | 9.4 |
| 5 | 88.2 | 82.2 | 92.3 | 87.9 | 60.9 | 6.4 | 12.9 | 0.3 | 3.1 | −7.5 | −0.6 | 3.6 | 0.2 |
| 6 | 94.8 | 90.1 | 93.2 | 83.3 | 16.5 | −19.7 | −2.5 | −5.2 | 2.6 | 15.9 | 2.6 | 4.6 | 1.8 |
| 7 | 104.3 | 109.2 | 95.4 | 89 | 92.8 | 35.8 | 24.8 | 15.3 | 6.8 | −9.7 | −3.6 | 11.2 | 26.7 |
| 8 | 98.6 | 85.5 | 92.7 | 82.2 | 15 | −33.8 | 0 | 14.6 | 8.9 | −10.3 | 14.3 | 10.9 | −1 |
| 9 | 102.1 | 100.6 | 89.2 | 92.3 | 28.9 | −12.6 | 11.9 | 6.1 | 24.7 | −22.1 | −0.7 | 10.4 | 6 |
| 10 | 95 | 88 | 95.2 | 87.4 | 23.7 | 3.9 | 33.8 | 3.6 | 12.6 | −20.1 | 3 | 9.3 | 5.7 |
| 11 | 98.8 | 94 | 92.5 | 90.6 | 17.2 | 6 | 4.3 | −4.7 | −5.8 | −19.3 | −0.7 | 7 | 3.3 |
| 12 | 93 | 95.8 | 92.9 | 83.4 | 9.9 | −7.3 | N.D. | −3.9 | −3.3 | −8.4 | 15.2 | −1 | −0.9 |
| 13 | 100.9 | 101 | 94.6 | 94.4 | 29.7 | −7.3 | 15.8 | 13.4 | 22.9 | −15.4 | 0 | 11.8 | 17.5 |

TABLE 2-continued

Inhibition (%) of various cell types by PluriSIn compounds (at 20 µM)

| | Pluripotent stem cells | | | | Differentiated cells | | | | | | | | |
|---|---|---|---|---|---|---|---|---|---|---|---|---|---|
| | | | | | Stem cell-derived differentiated cells | | | | | | | | |
| | | | | | ES-derived neural stem cells | ES-derived mesenchymal stem cells | ES-derived endodermal progenitors | ES-derived hepatocytes | iPS-derived cardiomyocytes | BJ-fibroblasts | Cancer cells | | |
| PluriSIn # | CSES2 | H9 | CSES2-SO2/3 | BJ-iPS28 | | | | | | | HeLa | Huh7 | Kelly |
| 14 | 90.1 | 79.4 | 90.1 | 81.7 | 18.4 | −1.5 | 18.8 | −4.1 | 3.9 | −18.6 | −2.3 | 11.5 | 0 |
| 15 | 77.6 | 79.5 | 72.2 | N.D. | 70.3 | 12 | 2.1 | 18.8 | 3.8 | −6.1 | 17.8 | 22.2 | 9.9 |

TABLE 3

EC50 values (µM) for inhibition of various cell types by PluriSIn compounds

| | Pluripotent stem cells | | | Differentiated cells | |
|---|---|---|---|---|---|
| | | | | CSES2-SO2/3 endodermal progenitors | BJ-fibroblasts |
| PluriSIn # | CSES2 | | CSES2-SO2/3 | BJ-iPS28 | |
| | 24 hours | 48 hours | 24 hours | 24 hours | 24 hours | 24 hours |
| 1 | 1.543 | 1.986 | 3.91 | 2.391 | >50 | >50 |
| 2 | 2.028 | 2.627 | 12.36 | 6.958 | >50 | >50 |
| 3 | 2.979 | 1.317 | 2.787 | 1.681 | >50 | >50 |
| 4 | 1.108 | 0.594 | 4.705 | 0.750 | >50 | >50 |
| 5 | 3.061 | 1.268 | 3.204 | 1.516 | >50 | >50 |
| 6 | 2.548 | 1.92 | 3.747 | 2.261 | >50 | >50 |
| 7 | 1.977 | 0.749 | 2.743 | 2.128 | >50 | >50 |
| 8 | 2.305 | 2.388 | 3.692 | 1.688 | >50 | >50 |
| 9 | 7.957 | 2.157 | 4.606 | 3.415 | >50 | >50 |
| 10 | 1.672 | 2.047 | 2.491 | 2.425 | >50 | >50 |
| 11 | 3.827 | 2.583 | 3.619 | 3.123 | >50 | >50 |
| 12 | 6.848 | 5.099 | 6.037 | 5.399 | >50 | >50 |
| 13 | 1.543 | 1.912 | 3.447 | 1.505 | >50 | >50 |
| 14 | 2.028 | 2.905 | 5.515 | 3.477 | >50 | >50 |
| 15 | 2.979 | 3.268 | 10 | 3.942 | >50 | >50 |

As shown in FIG. 26A and in Table 3, human ES cells (CSES2 cells) lost their sensitivity to PluriSIn #1 upon their differentiation to CSES2-derived endodermal progenitor cells (EPCs).

Similarly, as shown in FIG. 26B and in Table 3, human somatic cells (BJ-fibroblasts) acquired sensitivity to PluriSIn #1 upon their reprogramming to iPS cells (BJ-iPS28 cells).

Similarly, as shown in FIG. 27 and in Table 3, human ES cells (CSES2-SO2/3 cells) lost their sensitivity to each of the 15 PluriSIn compounds upon their differentiation to endodermal progenitor cells, and BJ-fibroblasts acquired sensitivity to each of the 15 PluriSIn compounds upon their reprogramming to iPS cells (BJ-iPS28 cells).

Unsupervised hierarchical clustering was performed using the compound inhibition profiles of tested cell types.

As shown in FIG. 28, hPSCs were clustered together by their response to small molecules, with a subgroup of 15 compounds exhibiting highly selective cytotoxicity towards hPSCs. These results indicate that hPSCs are in general sensitive to different compounds, as compared to other types of cells (e.g., differentiated cells).

In order to confirm the cytotoxic effect of various PluriSIns in additional assays, cells were treated with PluriSIns and subjected to an ATP-independent methylene blue viability assay and also examined by high-content microscopic imaging.

As shown in FIG. 29, PluriSIns #1 to #11 each reduced the viability of H9 ES cells considerably, as determined by a methylene blue assay.

As shown in FIG. 30, PluriSIns #1 to #11 each reduced the number of H9 ES cells considerably, as observed by microscopy.

Significantly, none of the PluriSIns was identified as cytotoxic in a previous high-resolution cytotoxicity screen preformed with HepG2 cells (data not shown), further indicating that their cytotoxicity is selective for PSCs.

In order to further verify the selectivity of the PluriSIns, and rule out any potential assay-related interference, undifferentiated and differentiated CSES2-SO2/3 cells were subjected to microscopy imaging after 24 hours of exposure to PluriSIns.

As shown in FIG. 31, PluriSIn #6 eliminated the red undifferentiated cells without exhibiting any detectable effect on the green differentiated cells. As further shown therein, the effect of the PluriSIn on the undifferentiated cells was comparable to that of 5 µM amsacrine hydrochloride, used as a cytotoxic control compound, whereas the PluriSIn-treated differentiated cells were comparable to untreated differentiated cells.

Similarly, as shown in FIGS. 32A-32C, PluriSIn #1 eliminated undifferentiated cells (FIG. 32A) without exhibiting any detectable effect on the differentiated cells (FIG. 32B), and also eliminated undifferentiated cells in a mixture of differentiated and undifferentiated cells (FIG. 32C).

In order to ascertain that the selectivity of PluriSIn cytotoxicity is cell type-dependent rather than cell medium-dependent, four non-pluripotent cell types (BJ-fibroblasts, HeLa, HepG2 and Kelly cells) were cultured in human embryonic stem cell medium and exposed to PluriSIn #1 for 72 hours. Cell viability was then determined by a methylene blue assay, as described hereinabove.

As shown in FIGS. 33 and 34, the PluriSIn #1 had no effect on the viability of non-pluripotent cells cultured in embryonic stem cell medium, thereby confirming that PluriSIn #1 cytotoxicity is cell type-dependent rather than cell medium-dependent.

The above results indicate that PluriSIns exhibit a significant, robust, rapid and selective cytotoxic effect toward hPSCs.

Example 3

Mechanism of Action of PluriSIns

As described hereinabove, 9 of the 15 identified PluriSIns comprise a phenylhydrazine moiety (see Table 1). Specifically, PluriSIns #1, #5, #6, #9, #10 and #14 comprise an N'-phenylhydrazide moiety (an acid derivative of a phenylhydrazine), PluriSIns #8 and #13 comprise an N'-phenylhydrazone moiety (a ketone or aldehyde derivative of a phenylhydrazine), and PluriSIn #11 comprises an N'-phenylhydrazine moiety which may tautomerize to an N'-phenylhydrazone moiety.

This presence of a common phenylhydrazine moiety in 9 of 15 of the PluriSIns is approximately a 60-fold over-representation of this moiety compared to the entire "golden" library ($p<10^{-16}$), suggesting this moiety may be linked to the mechanism of action or to the specificity of the PluriSIns.

In an attempt to further elucidate the mechanism of action of the PluriSIns, the activity of the most potent and selective compound, PluriSIn #1 (isonicotinic acid N'-phenylhydrazide), as well as that of PluriSIn #6 (2-hydroxy-2-(thiophen-2-yl)-2-phenylacetic acid 4-methyl-N'-phenylhydrazide), were further studied.

In a toxicogenomic study, various types of human ES cells were exposed to PluriSIns #1 or #6, or to control DMSO, for 12 hours, a time point at which no cell death was yet observed. For comparison, early endodermal progenitors derived from human ES cells (as described hereinabove) were treated likewise. RNA was then derived from the cells, and gene expression microarrays (Affymetrix U133A) were used to analyze gene expression, as described in the Materials and Methods section. Several bioinformatic tools were then applied to analyze the gene expression changes, in order to identify perturbed pathways, as described in the Materials and Methods section.

As shown in FIG. 35, unsupervised hierarchical clustering revealed marked gene expression changes in the PluriSIn-treated undifferentiated cells compared to their untreated controls, whereas no such gene expression changes occurred in treated differentiated cells.

As shown in FIG. 36, PluriSIn treatment resulted in multiple gene expression changes (>2-fold change) associated with apoptosis.

Functional analysis of deregulated genes (>2-fold change) was conducted using DAVID Functional Annotation tool, as described by Huang et al. [*Nature Protocols* 4:44-57 (2009)], and revealed significant enrichment for apoptosis (2.7-fold enrichment, p=0.007 after Benjamini correction).

The finding of gene expression associated with apoptosis is consistent with previous reports that pluripotent cells are prone to apoptosis [Qin et al., *Journal of Biological Chemistry* 282:5842-5852 (2007); Momcilovic et al., *PloS One* 5:e13410 (2010)]. However, pluripotent cells have also been reported to be susceptible to other types of cell death, such as oncosis [Tan et al., *Stem Cells* 27:1792-1801 (2009)] and autophagy [Alexander et al., *PNAS* 108:15828-15833 (2011)]. An Annexin V-FITC detection assay and immunoblotting for caspase-3 (a hallmark executioner of apoptosis) were therefore used in order to confirm that the massive hPSC death induced by PluriSIn #1 is indeed apoptosis.

As shown in FIGS. 37A and 37B, PluriSIn #1 treatment increases the number of apoptotic cells approximately 7-fold 16 hours post-treatment.

As shown in FIG. 38, PluriSIn #1 treatment enhanced activation of caspase-3.

The effect of the pancaspase inhibitor Z-VAD-FMK on PluriSIn #1-induced cell death was also examined. Cells were treated with 25 µM or 100 µM of Z-VAD-FMK, and 1 hour later PluriSIn #1 (20 µM) was added to the medium. After 24 hours, the cultures were subjected to cell viability measurements, as described hereinabove.

As shown in FIG. 39, Z-VAD-FMK significant suppressed PluriSIn #1-induced cell death, in a dose-dependent manner.

These results confirm that apoptosis is the primary mechanism of cell death induced by PluriSIn #1.

Furthermore, as shown in FIG. 40, PluriSIn #1 and #6 treatment resulted in considerable gene expression changes associated with endoplasmic reticulum (ER) stress and unfolded protein response (UPR). Gene expression change conferred by dithiothreitol (1 µM), a general ER stress inducer, was used as a positive control.

DAVID functional analysis revealed enrichment for ER stress response (12-fold enrichment).

The most upregulated gene following PluriSIn treatment was CHOP (also known as DDIT3), a hallmark of UPR (9-fold upregulation, p=0.01).

To further study the significance of UPR, XBP1 mRNA splicing and eIF2α phosphorylation, hallmarks of UPR, were further examined. Human ES cells and ES-derived differentiated cells were treated with PluriSIn #1 for 12 hours, and expression of the spliced isoform sXBP1 was determined by quantitative PCR and by immunoblotting, as described in the Materials and Methods section. Gene expression change conferred by dithiothreitol (1 µM) was used as a positive control.

As shown in FIG. 41, PluriSIn #1 increased expression of the spliced isoform sXBP1 by approximately 3.5-fold, as determined by quantitative PCR.

As shown in FIG. 42, PluriSIn #1 increased levels of phosphorylated eIF2α in hPSCs, as determined by immunoblotting.

These results confirm that PluriSIn #1 induces UPR in hPSCs.

As further shown in FIGS. 41 and 42, respectively, PluriSIn #1 did not increase expression of the spliced isoform sXBP1 or phosphorylation of eIF2α in 8-day differentiated cells.

The gene expression data was then analyzed using the Connectivity Map (cmap), a database of genome-wide transcriptional expression data from cultured human cells treated with bioactive small molecules. Cmap was developed to facilitate the discovery of pathways perturbed by small molecules of unknown activity, based on the common gene expression changes that similar small molecules confer [Lamb et al., *Science* 313:1929-1935 (2006)]. Cmap includes over 7,000 expression profiles representing 1,309 distinct molecules, including cytotoxic compounds that work through varied mechanisms (such as cell cycle blockers, CDK inhibitors, topoisomerase inhibitors, alkaloids, etc.). The analysis lists all compounds by their similarity to the tested compound, and provides "connectivity values" between −1 to 1 that represent the degree of similarity.

The cmap database was queried with a list of genes that were at least 2-fold upregulated or downregulated in hPSCs following 12 hours treatment with PluriSIn #1. A list describing the 10 compounds exhibiting the most similar activity to that of PluriSIn #1 is presented in Table 4. A similar query was performed for PluriSIn #6, and a list describing the 10 compounds exhibiting the most similar activity to that of PluriSIn #6 is presented in Table 5.

TABLE 4

Top 10 compounds exhibiting high cmap connectivity scores with respect to PluriSIn #1 (p = 0.00000 for each compound)

| Rank | Cmap name | Cmap score |
|---|---|---|
| 1 | Cephaeline** | 0.897 |
| 2 | Cycloheximide** | 0.881 |
| 3 | Emetine** | 0.876 |
| 4 | Anisomycin** | 0.849 |
| 5 | Helveticoside | 0.766 |
| 6 | Gossypol | 0.735 |
| 7 | Lanatoside C | 0.733 |
| 8 | Digitoxigenin | 0.687 |
| 9 | Valinomycin* | 0.680 |
| 10 | 8-Azaguanine* | 0.671 |

**Protein synthesis inhibitor (as defined in cmap)
*Compounds not defined in cmap as protein synthesis inhibitors, but known to attenuate protein translation

TABLE 5

Top 10 compounds exhibiting high cmap connectivity scores with respect to PluriSIn #6 (p = 0.00000 for each compound)

| Rank | Cmap name | Cmap score |
|---|---|---|
| 1 | Thapsigargin | 0.887 |
| 2 | Puromycin* | 0.772 |
| 3 | Niclosamide | 0.770 |
| 4 | Valinomycin* | 0.723 |
| 5 | Gossypol | 0.702 |
| 6 | Emetine** | 0.681 |
| 7 | Alexidine | 0.673 |
| 8 | Cephaeline** | 0.667 |
| 9 | Phenoxybenzamine | 0.648 |
| 10 | 5707885* | 0.627 |

**Protein synthesis inhibitor (as defined in cmap)
*Compounds not defined in cmap as protein synthesis inhibitors, but known to attenuate protein translation As shown in Table 4, PluriSIn #1 activity is highly similar to that of protein synthesis inhibitors (PSIs), as PSIs were ranked highest in the list, with very high connectivity scores. Indeed, only 4 compounds (cephaeline, emetine, anisomycin, cycloheximide) are classified as bona fide PSIs in the cmap database [Iorio et al., *PNAS* 107: 14621-14626 (2010)], and all of them appeared among the 10 most similar compounds to PluriSIn #1 (65-fold enrichment, p<0.0001).

For comparison, the cmap database was also queried with a list of genes that were at least 2-fold upregulated or downregulated in 8-day differentiated cells following 12 hours treatment with PluriSIn #1. The analysis did not detect similarity to any small molecule, further confirming that PluriSIn #1 does not alter global gene expression in these cells.

Similarly, as shown in Table 5, PluriSIn #6 activity is quite similar to that of protein synthesis inhibitors (PSIs).

The similarity between PSIs and PluriSIn #1 and #6 is consistent with the fact that UPR can lead to translational attenuation. In order to confirm this link, the effect of PluriSIn #1 treatment on protein synthesis was determined A pulse-chase radioactive labeling assay was used to measure incorporation of $^{35}$S-Met into ES cells and differentiated cells (fibroblasts) in the presence or absence of PluriSIn #1. Cycloheximide (10 μM), a general protein synthesis inhibitor, was used as a positive control.

As shown in FIG. 43, PluriSIn #1 decreased protein synthesis in hPSCs by approximately 30% (p=0.005), but exhibited no effect in differentiated cells (fibroblasts).

The above results indicate that PluriSIn #1 exerts its cytotoxic effect by leading to UPR and PSI in undifferentiated cells, thereby resulting in their apoptosis. Furthermore, no global gene expression changes were identified in the differentiated cells and no apoptotic/UPR genes were deregulated. As PluriSIn #1 does not induce UPR and PSI in differentiated cells, PluriSIn #1 selectively targets undifferentiated cells, whereas differentiated cells remain intact.

Example 4

Inhibition of SCD1 by PluriSIns

Previous studies have shown that none of the PluriSIns exhibits a cytotoxic effect (data not shown). However, three of these compounds, including PluriSIn #1 and PluriSIn #6, have been identified, in an in vitro biochemical screen, as possible direct inhibitors of SCD1, a key enzyme in the biosynthesis of mono-unsaturated fatty acids (MUFA) Inhibition of SCD1 has been reported to induce ER stress and UPR in some human cancer cell lines, leading to apoptosis of these cells [Roongta et al., *Molecular Cancer Research* 9:1551-1561 (2011); Minville-Walz et al., *PloS One* 5:e14363 (2010); Scaglia et al., *PloS One* 4:e6812 (2009); Hess et al., *PloS One* 5:e11394 (2010); Morgan-Lappe et al., *Cancer Research* 67:4390-4398 (2007); Mason et al., *PloS One* 7:e33823 (2012)].

In order to ascertain whether PluriSIns exert a significant effect via SCD inhibition, gene expression changes that we observed in hPSCs after their treatment with PluriSIn #1 were compared with those previously reported in a human cancer cell line (H19299) following the pharmacological inhibition of SCD1 by the specific inhibitor A939572 [Roongta et al., *Molecular Cancer Research* 9:1551-1561 (2011)].

As shown in FIG. 44, 12 of the 18 genes that exhibited the most significant expression changes (p<0.05, >2 fold-change) following SCD1 inhibition (as reported by Roongta et al. [*Molecular Cancer Research* 9:1551-1561 (2011)]), were also significantly deregulated after treatment with PluriSIns #1 or #6. In addition, many of the aforementioned genes related to the ER stress pathway.

These results suggest that the selective cytotoxicity (and ER stress) induced by PluriSIns is effected via SCD inhibition.

The results presented herein are consistent with a report that SCD1 inhibition induced a peculiar UPR activation in human cancer cell lines, characterized by a sharp increase in CHOP expression without affecting the expression of the ER chaperone GRP78 [Minville-Walz et al., *PloS One* 5:e14363 (2010)]. As described in Example 3, PluriSIn treatment induced an unfolded protein response (UPR), with CHOP being the most upregulated gene. In contrast, GRP78 expression was not significantly altered by PluriSIn treatment (1.2-fold, p=0.13).

In order to directly examine whether PluriSIn #1 inhibits SCD activity, and whether this inhibition is restricted to pluripotent cells, SCD1 activity was measured by a pulse-chase labeling assay, as described in the Materials and Methods section. Human ES and differentiated cells (H9 and BJ-fibroblasts, respectively) were treated with PluriSIn #1 for 12 hours, and were than labeled with [1-$^{14}$C] stearic acid, the substrate of SCD1. Following up to 4 hours of incubation, lipids were purified, and enzymatic activity was then evaluated by direct measurement of the radioactive intensities of SCD1 substrate and product, [1-$^{14}$C] oleic acid.

As shown in FIG. 45, PluriSIn #1 decreased SCD1 activity by approximately 65% decrease in ES cells (p=2.1×10$^{-6}$).

In order to determine whether hPSC viability indeed depends on functional SCD1 activity, hPSCs were exposed to 75 nM of the specific SCD1 inhibitors A939572 and CAY-10566 for 48 hours. Some samples were supplemented with 100 μM oleic acid in order to evaluate the effect of exogenous supplementation of oleic acid (a product of SCD1 activity) on cell death.

As shown in FIG. 46, the SCD1 inhibitors A939572 and CAY-10566 each caused a considerable decrease in viability of hPSCs (>80% decrease, p=6.4×10$^{-6}$ for A939572, p=2×10$^{-5}$ for CAY-10566). As further shown therein, oleic completely rescued the cells from SCD-1 inhibitor-induced cell death (p=3×10$^{-4}$ for oleic acid with A939572, p=10$^{-4}$ for oleic acid with CAY-10566).

These results confirm that hPSCs require SCD activity for survival.

In order to further investigate the effect of SCD activity on hPSC viability, the ability of exogenous supplementation of oleic acid (the direct product of SCD1) to rescue cells from PluriSIn-induced apoptosis was further studied, using procedures described in the Materials and Methods section. Cells were exposed to PluriSIn #1 in the presence of increasing concentrations of BSA-conjugated oleic acid (BSA-OA).

As shown in FIGS. 47 and 48, BSA-OA protected cells against PluriSIn #1-induced apoptosis in a dose-dependent manner, with full rescue occurring in the presence of high concentrations, whereas BSA alone did not afford any protection against apoptosis. As further shown therein, this protection was specific, as BSA-OA did not affect proliferation in the control cells, and did not protect cells against the cytotoxicity of a DNA-topoisomerase inhibitor (amsacrine, FIG. 47).

For comparison, cells were exposed to 20 μM of PluriSIn #1, #2, #3 and #6 in the presence of 100 μM BSA-OA.

As shown in FIG. 49, BSA-OA protected cells against cell death induced by PluriSIn #1 (p=0.0004), PluriSIn #5 (p=0.0006), or PluriSIn #6 (p=0.006), but not cell death induced by PluriSIn #2 or PluriSIn #3.

As PluriSIn #1, PluriSIn #5 and PluriSIn #6 each comprise a phenylhydrazine moiety, and PluriSIn #2 or PluriSIn #3 do not comprise such a moiety, the above results suggest that PluriSIns comprising a phenylhydrazine moiety share a cytotoxic mechanism.

In order to confirm that SCD1 inhibition underlies the cellular perturbations observed following the exposure of hPSCs to PluriSIn #1, it was ascertained that the SCD1 inhibitor A939572 recapitulates the cellular response induced by PluriSIn #1. ER stress, protein synthesis inhibition and apoptosis were evaluated as described hereinabove, after both treatment with PluriSIn #1 and with A939572.

As shown in FIG. 50, PluriSIn #1 and A939572 both enhanced apoptosis of undifferentiated cells in a similar manner.

As shown in FIG. 51, A939572 increased expression of the spliced isoform sXBP1 by approximately 2-fold in undifferentiated ES cells, as determined by quantitative PCR, and did not increase expression in differentiated cells.

As shown in FIG. 52, PluriSIn #1 and A939572 both increased levels of phosphorylated eIF2α in ES cells in a similar manner, as determined by immunoblotting, and did not increase levels in differentiated cells.

As shown in FIG. 53, A939572 decreased protein synthesis in ES cells by approximately 50%.

As shown in FIG. 54, the ER stress inducer dithiothreitol and the protein synthesis inhibitor cycloheximide are cytotoxic towards both embryonic stem cells and differentiated cells (human fibroblasts), and oleic acid does not protect cells against their cytotoxicity.

The above results indicate that survival of hPSCs depends on the normal activity of SCD1, and that hPSCs are highly sensitive to perturbances in the monounsaturated fatty acid (MUFA) biosynthesis pathway, and that the selective cytotoxicity of at least some PluriSIns (e.g., PluriSIns comprising a phenylhydrazine moiety) toward hPSCs is associated with its interference with SCD1 activity and the sensitivity of these cells to interference with SCD1 activity. Similarly to some cancer cell lines, inhibition of SCD1 activity in hPSCs induces ER stress and UPR, followed by translational attenuation, and ultimately may result in apoptosis of the cells. FIG. 55 describes such a mechanism schematically.

Example 5

Effect of PluriSIn Cytotoxicity on Mouse Pluripotent Stem Cells and Blastocysts

Mouse pluripotent stem cells (mPSCs) are widely used in pluripotency-related research, and generating pure cultures of mPSC-differentiated cells is therefore of great importance. It was therefore determined whether mPSCs are also sensitive to PluriSIns. R1 Oct4-GFP mouse ES cells were plated in 96-well plates and exposed to PluriSIns #1, #2, #4 or #6 at a concentration of 20 μM, and the viability of the cells was then assessed after 24 hours, 48 hours and 72 hours, using a luminescent viability assay and fluorescent microscopy imaging, as described in the Materials and Methods section.

As shown in FIG. 56, each of the four tested PluriSIns induced a considerable degree of cell death in mPSCs. A representative sample showing Cell death induced by PluriSIn #6 is shown in FIG. 57. These results indicate that PluriSIn sensitivity is shared by mouse and human PSCs Inhibition of mPSCs by PluriSIns was not as efficient as inhibition of hPSCs, and required a longer exposure to the compounds. This may be the consequence of inherent differences between mouse and human PSCs, but may also be attributed to the different medium and factors used in the culturing these cell types.

A mouse system was then utilized in order to ascertain whether PluriSIn #1 is cytotoxic to the inner cell mass (ICM) cells, from which ES cells are derived. It was hypothesized that if SCD1 activity is crucial to pluripotent cells in vivo, then PluriSIn #1 will be cytotoxic to the ICM cells and thus be detrimental to normal embryonic development.

As described in the Materials and Methods section, a series of independent experiments were performed with two strains of mice, in which two-cell embryos were collected from the oviducts of pregnant mice at approximately 1.5 days post coitum, and these embryos were then let to develop in vitro. The embryos reached the morula stage at approximately 3.5 days post coitum, and were then transferred either to drops with 20 µM PluriSIn #1 (17 embryos in total), drops with 20 µM PluriSIn #1 and 100 µM oleic acid (7 embryos in total), or to control drops with 0.2% DMSO (8 embryos in total), while other control embryos were left to develop without transfer at all (10 embryos in total). Using light microscopy imaging, the development of the embryos was followed until they became mature blastocysts (at approximately 4.5 days post coitum, after which all embryos disintegrated in culture). The blastocysts were then classified into three distinct categories: (A) good quality mouse blastocysts with large and distinct ICM; (B) mouse blastocysts with distinct, but smaller, ICM; and (C) bad quality mouse blastocysts with indistinguishable ICM, as described by Cortes et al. [*Stem Cells and Development* 17:255-267 (2008)].

All 8 control blastocysts that had been transferred to drops with 0.2% DMSO, and all 10 control blastocysts that had not been transferred to new drops, developed into blastocysts with a distinct ICM (category A/B).

In contrast, less than one half (7/17) of the embryos exposed to PluriSIn #1 developed into good quality (category A/B) blastocysts, whereas other embryos (6/17) developed into blastocysts with no distinguished ICM (category C), or were stuck at the morula stage (4/17). This marked difference in the embryonic fate after exposure to PluriSIn #1 was highly significant (p=0.0001).

Representative examples of blastocysts are shown in FIG. 58, showing good quality control blastocysts and PluriSIn-treated blastocysts, bad quality PluriSIn-treated blastocysts, and PluriSIn-treated embryos stuck at the morula stage.

As shown in FIGS. 59 and 60, oleic acid supplementation rescued most embryos from the effects of PluriSIn #1, with 5 of 7 oleic acid-supplemented embryos (71%) developing into high-quality blastocysts, as opposed to 7 of 17 (41%) in the absence of oleic acid.

The above experiments with mouse embryos were then repeated using the SCD1 inhibitor A939572 instead of PluriSIn #1, and compared with the results obtained with PluriSIn #1, in order to confirm that the effects of PluriSIn #1 are associated with inhibition of SCD1 activity.

As further shown in FIGS. 60 and 61, A939572 significantly inhibited development of blastocysts, with only 5 of 9 embryos (56%) exposed to A939572 developing into high quality blastocysts, as opposed to 18 of 18 control embryos (p=0.007). As further shown therein, oleic acid supplementation increased the proportion of high quality blastocysts to 5 of 7 (71%).

These results indicate that PluriSIn #1 is cytotoxic to ICM cells and thus precludes normal development of the blastocyst. These results further indicate that the dependence of PSCs on SCD1 (e.g., as described in Example 4) is inherent to the pluripotent state, both in vitro and in vivo, and that the cytotoxicity of PluriSIn #1 towards ICM cells is associated with inhibition of SCD1 activity.

Example 6

Effect of PluriSIn Cytotoxicity on Teratomas

One particularly desirable goal of selective hPSC inhibition is prevention of teratoma formation by the efficient removal of residual undifferentiated cells from culture. The usefulness of PluriSIns for such an application was therefore tested using in vitro and in vivo assays, as described in the Materials and Methods section.

The PluriSIns were first tested in various culture conditions and exposure durations. Interestingly, PluriSIns were more potent in smaller (384- or 96-well) plates than in larger (6-well or 10 cm) plates, and more potent in low cell densities than in high cell densities, suggesting a possible protective effect conferred by large colonies.

Thus, for example, as shown in FIG. 62, a 48 hour exposure of the cells to 20 µM PluriSIn #1 was required for complete elimination of undifferentiated cells cultured in 6-well plates.

In addition, as shown in FIGS. 63A and 63B, hPSCs cultured on MEFs (mouse embryonic fibroblasts) with regular ES cell medium were less sensitive to PluriSIns. This result may be due to the different media compositions, or due to a protective effect of the MEFs.

Among the conditions tested, PluriSIns were found to eliminate hPSCs most potently when cultured on Matrigel™-coated plates, without feeder cells, using mTeSR1 defined medium.

The number of residual undifferentiated cells that remained in culture after PluriSIn #1 application in vitro was then evaluated, and the in vivo tumorigenicity of such cells was determined.

Mixed cell populations were cultured in 6-well plates and exposed to PluriSIn #1 for 48 hours. The cells were then analyzed by FACS analysis, using staining for the pluripotent marker TRA-1-60, and by fluorescence microscopy imaging of OCT4, as described in the Materials and Methods section.

As shown in FIG. 64, exposure to PluriSIn #1 for 48 hours eliminated over 99% of the pluripotent cells from culture, as determined by FACS analysis.

As shown in FIG. 65, exposure to PluriSIn #1 for 48 hours eliminated almost all OCT4-expressing cells, as determined by fluorescence microscopy imaging of CSES2-SO2/3 cells.

These results indicate that PluriSIn #1 is highly effective at eliminating pluripotent cells from mixed cell populations.

To evaluate in vivo tumorigenicity, hPSCs were cultured under the abovementioned conditions in the presence or absence of PluriSIn #1, and the cultures were then injected subcutaneously into immuno-compromised NOD-SCID IL2Rγ-/- mice, which have been previously reported to be especially susceptible to human-derived tumors [Quintana et al., *Nature* 456:593-598 (2008)]. Mice were Sacrificed after 4-6 weeks, and teratoma formation was then assessed.

All mice (3/3) injected with control H9 ES cells developed teratomas, whereas none of the mice (0/3) injected with PluriSIn #1-treated H9 ES cells developed teratomas.

Similarly, CSES2-502 and BJ-iPS28 cell lines were injected into immune-compromised mice (2 mice for each cell line), with control cells and treated cells being injected into the two body sides of the same animal.

All of the injected mice (4/4) developed teratomas only in the side injected with control hPSCs. FIGS. 66A and 66B show representative examples of teratoma development only on the side injected with untreated cells.

The effect of PluriSIns was on teratoma formation was then evaluated in a model designed to simulate a clinical setting. Human ES and iPS cells were spontaneously differentiated in culture for a period of 10 days, and the differentiated cells were then harvested and plated together with undifferentiated cells, in a 1:1 mixture of undifferentiated and differentiated cells, as described in the Materials and Methods section. Following a 48 hour exposure to PluriSIn #1, cells were harvested and injected subcutaneously into NOD-SCID IL2Rγ–/– mice, with each mouse being injected with PluriSIn #1-treated cells into one side of its body and with control cells into the other side. The same total number of cells was injected into both sides.

All of the injected mice (4/4) developed teratomas only in the side injected with control hPSCs. FIGS. 67A and 67B show representative examples of teratoma development only on the side injected with untreated cells. As shown in FIG. 68, teratoma development was confirmed by histological examination.

As shown in Table 6 below, taken together, no teratomas (0/11) were generated in mice upon transplantation with PluriSIn #1-treated hPSCs, whereas untreated cells always generated teratomas (10/10) in mice upon transplantation. Similarly, no teratomas (0/4) were generated in mice upon transplantation with PluriSIn #1-treated 1:1 mixtures of differentiated and undifferentiated hPSCs, whereas untreated mixtures always generated teratomas (4/4) in mice upon transplantation.

TABLE 6

Incidence of teratoma formation following injection of PluriSIn #1-treated or untreated hPSCs

| | Control (untreated hPSCs) | PluriSIn #1-treated hPSCs |
|---|---|---|
| Undifferentiated cells only | 10/10 | 11/11 |
| 1:1 mixture of undifferentiated and differentiated cells | 4/4 | 0/4 |

The above results indicate that PluriSIns can be efficiently used to remove tumorigenic undifferentiated cells from cultures of hPSC-derived cells.

Example 7

Effects of SCD1 Inhibitors on Pluripotent Stem Cell Inhibition

As described hereinabove, the SCD1 inhibitors A939572 and CAY-10566 caused a considerable decrease in viability of pluripotent stem cells, and PluriSIns, which exhibit an SCD inhibitory effect, are effective at eliminating pluripotent cells from mixed cell populations, and removing tumorigenic undifferentiated cells from cultures of hPSC-derived cells.

In order to ascertain the efficacy of SCD1 inhibitors against tumorigenic undifferentiated cells, the specific SCD inhibitor A939572 was tested for prevention of teratoma formation following transplantation of embryonic stem cells, using procedures such as described in Example 6.

As shown in FIG. 69, treatment with A939572 exhibited a protective effect against teratoma formation upon transplantation of embryonic stem cells in mice.

The above results indicate that inhibition of SCD1 activity can be efficiently used to remove tumorigenic undifferentiated cells from cultures of hPSC-derived cells.

In order to further ascertain the efficacy of SCD1 inhibitors against tumorigenic undifferentiated cells, an additional specific SCD inhibitor (e.g., CAY-10566) is tested for prevention of teratoma formation following transplantation of embryonic stem cells, as described hereinabove.

Example 8

Effect of siRNA Knockdown of SCD1 Expression on Pluripotent Stem Cell Inhibition As described hereinabove, the SCD1 inhibitors A939572 and CAY-10566 caused a considerable decrease in viability of pluripotent stem cells, which is consistent with the SCD inhibitory effect of PluriSIns.

In order to further demonstrate that SCD1 inhibition in general can inhibit pluripotent stem cells, SCD1 expression was inhibited using siRNA knockdown of the SCD1 gene, using procedures described in the Materials and Methods section. Untreated cells and cells treated with mock siRNA were used as a control. The viability of the pluripotent stem cells was then determined.

As shown in FIGS. 70 and 71, siRNA knockdown of the SCD1 gene resulted in a considerable decrease in viability of stem cells (p=0.002).

As further shown in FIG. 71, the decrease in viability was dependent on the dose of siRNA.

As further shown in FIG. 71, exogenous supplementation of oleic acid rescued the cells from siRNA knockdown of the SCD1 gene (p=0.006)

These results further confirm that SCD1 inhibition in general can inhibit pluripotent stem cells, and that the SCD1 inhibition can be effected via a nucleic acid silencing sequence.

Example 9

Effect of PluriSIn Cytotoxicity on Undifferentiated Cancer Cells

A selective inhibition of undifferentiated cells allows for the possibility of selective inhibition of cancer cells, e.g., cancer treatment. The effect of PluriSIn #1 on undifferentiated cancer cells was therefore tested and compared to the effect on related differentiated cells.

In one experiment, immortalized BJ fibroblasts served as differentiated cells and were compared with BJ fibroblasts induced to undergo cellular transformation, which served as their undifferentiated cancerous counterparts. Fibroblasts were immortalized by expression of human telomerase reverse transcriptase (hTERT), and transformed by a combination of expression of hTERT and the oncogenic mutant H-RasV12, concomitantly with inhibition of p53 and retinoblastoma protein (RB) by simian virus 40 (SV40) Large-T (LT) and Small-T (ST) antigens, according to procedures described in Scaffidi & Misteli [*Nature Cell Biology* 13:1051-1061 (2011)].

In a second experiment, undifferentiated stem-like glioma cells (SLGCs) were compared with SLGCs differentiated by monolayer adhesion and exposure to 1 µM retinoic acid for one week, in accordance with procedures described by Campos et al. [*Clinical Cancer Research* 16:2715-2728 (2010)]. Differentiation of SLGCs is associated with a reduction in tumorigenicity [Campos et al., *Clinical Cancer Research* 16:2715-2728 (2010)].

The differentiated and undifferentiated cells were exposed to PluriSIn #1 at concentrations of up to 100 µM for 72 hours under low (2%) fetal bovine serum conditions. Their viability was then measured using a methylene blue viability assay, as described hereinabove.

As shown in FIG. 72, PluriSIn #1 was highly cytotoxic towards transformed BJ fibroblasts, while having little effect on normal (immortalized) BJ fibroblasts.

This result indicates that cellular transformation, resulting in cancer cells, significantly increases cellular sensitivity to PluriSIn #1.

As shown in FIG. 73, PluriSIn #1 was highly cytotoxic towards undifferentiated SLGC, but had no apparent effect on differentiated SLGCs.

This result indicates that cancer cells lose their sensitivity to PluriSIn #1 upon differentiation to non-tumorigenic cells, even after only one week of differentiation.

The above results suggest that PluriSIns are selectively cytotoxic to undifferentiated cancer cells (e.g., cancer stem-like cells), in the same manner that PluriSIns are selectively cytotoxic to pluripotent stem cells.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of inhibiting undifferentiated cells, the method being effected by contacting undifferentiated cells with the following compound:

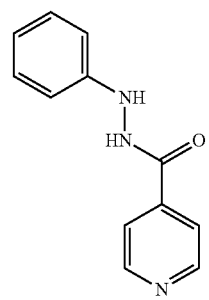 [SMILES: O=C(NNc1ccccc1)c1ccncc1]

said undifferentiated cells being selected from the group consisting of pluripotent stem cells, cancer stem cells and Grade 4 undifferentiated cancer cells.

2. The method of claim 1, wherein said undifferentiated cells comprise pluripotent stem cells.

3. The method of claim 1, wherein said undifferentiated cells comprise cancer stem cells and/or Grade 4 undifferentiated cancer cells.

* * * * *